US011169150B2

(12) United States Patent
Chilkoti et al.

(10) Patent No.: US 11,169,150 B2
(45) Date of Patent: Nov. 9, 2021

(54) CHIPS, DETECTORS, AND METHODS OF MAKING AND USING THE SAME

(71) Applicant: Sentilus Holdco LLC, Norcross, GA (US)

(72) Inventors: Ashutosh Chilkoti, Durham, NC (US); Angus Hucknall, Durham, NC (US)

(73) Assignee: Sentilus Holdco LLC, Norcross, GA (US)

( * ) Notice: Subject to any disclaimer, the term of this patent is extended or adjusted under 35 U.S.C. 154(b) by 872 days.

(21) Appl. No.: 15/746,081

(22) PCT Filed: Jul. 15, 2016

(86) PCT No.: PCT/US2016/042551
§ 371 (c)(1),
(2) Date: Jan. 19, 2018

(87) PCT Pub. No.: WO2017/015132
PCT Pub. Date: Jan. 26, 2017

(65) Prior Publication Data
US 2018/0217136 A1    Aug. 2, 2018

Related U.S. Application Data

(60) Provisional application No. 62/194,505, filed on Jul. 20, 2015.

(51) Int. Cl.
*G01N 1/00* (2006.01)
*G01N 33/543* (2006.01)
*G01N 33/574* (2006.01)

(52) U.S. Cl.
CPC ..... *G01N 33/54366* (2013.01); *G01N 33/543* (2013.01); *G01N 33/574* (2013.01)

(58) Field of Classification Search
None
See application file for complete search history.

(56) References Cited

U.S. PATENT DOCUMENTS

| 5,485,277 A | 1/1996 | Foster |
| 2012/0315191 A1 | 12/2012 | Maekawa et al. |
| 2013/0157889 A1* | 6/2013 | Chilkoti ........... A61B 5/150022 506/9 |
| 2013/0217063 A1 | 8/2013 | Metzger et al. |

(Continued)

FOREIGN PATENT DOCUMENTS

| JP | H07506430 A | 7/1995 |
| JP | 2011220996 A | 11/2011 |
| WO | 9322053 A1 | 11/1993 |

(Continued)

OTHER PUBLICATIONS

Hyun et al. (Mar. 2006) "Patterning Cells in Highly Deformable Microstructures: Effect of Plastic Deformation of Substrate on Cellular Phenotype and Gene Expression", Biomaterials, 27(8):1444-1451.

*Primary Examiner* — Jyoti Nagpaul
(74) *Attorney, Agent, or Firm* — Cozen O'Connor

(57) ABSTRACT

Disclosed herein are chips, devices, methods of making the same, and methods of detecting a target analyte, and methods of diagnosing an individual with a disease or condition when a target analyte associated with the disease or condition is detected.

20 Claims, 31 Drawing Sheets
Specification includes a Sequence Listing.

(56) References Cited

U.S. PATENT DOCUMENTS

2014/0180220 A1 6/2014 Chilkoti et al.
2015/0253321 A1 9/2015 Chou et al.

FOREIGN PATENT DOCUMENTS

| WO | 9322058 A1 | 11/1993 |
| WO | 2007035527 A2 | 3/2007 |
| WO | 2013003624 A2 | 1/2013 |
| WO | 2014055559 A1 | 4/2014 |
| WO | 2017015132 A1 | 1/2017 |

* cited by examiner

EXPOSED TO A+ BLOOD

EXPOSED TO B+ BLOOD

EXPOSED TO O+ BLOOD

SEQUENCE LISTING

```
<160> NUMBER OF SEQ ID NOS: 11

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(17)
```

-continued

```
<223> OTHER INFORMATION: peptide nucleic acid (PNA) linkages

<400> SEQUENCE: 1
gtccaccacc ctgttgc                                                    17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(17)
<223> OTHER INFORMATION: peptide nucleic acid (PNA) linkages

<400> SEQUENCE: 2
accttgtcat gtaccat                                                    17

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)

<400> SEQUENCE: 3
gcaacagggu gguggaccuc a                                               21

<210> SEQ ID NO 4
<211> LENGTH: 23
<212> TYPE: RNA
<213> ORGANISM: Unknown
<220> FEATURE:
<223> OTHER INFORMATION: Description of Unknown: mir-155 target sequence
<220> FEATURE:
<221> NAME/KEY: misc_feature
<222> LOCATION: (1)..(23)

<400> SEQUENCE: 4
uuaaugcuaa ucgugauagg ggu                                             23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(20)
<223> OTHER INFORMATION: locked nucleic acid (LNA) linkages

<400> SEQUENCE: 5
cctatcacga ttagcattaa                                                 20

<210> SEQ ID NO 6
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(23)

<400> SEQUENCE: 6
uucaugcuaa ucgugauagg ggu                                              23

<210> SEQ ID NO 7
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)

<400> SEQUENCE: 7
uuccugcuaa ucgugauagg ggu                                              23

<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)

<400> SEQUENCE: 8
uuccugcuca ucgugauagg ggu                                              23

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)

<400> SEQUENCE: 9
uuccugcucc ucgugauagg ggu                                              23

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)

<400> SEQUENCE: 10
uuccugcucc ucgugcuagg ggu                                              23

<210> SEQ ID NO 11
<211> LENGTH: 23
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: misc_feature
<222> LOCATION: (1)..(23)

<400> SEQUENCE: 11
uuccugcucc ucgugcucgg ggu                                              23
```

CHIPS, DETECTORS, AND METHODS OF MAKING AND USING THE SAME

CROSS-REFERENCE TO RELATED APPLICATIONS

This application is a U.S. National Stage entry filed under 35 U.S.C. § 371 of International Application PCT/US2016/042551 filed on Jul. 15, 2016, and claims the benefit of and priority to U.S. Provisional Application for Patent Ser. No. 62/194,505 filed Jul. 20, 2015, the entire contents of each of which are incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 6, 2021, is named 048469-504N01US_ST25.txt and is 3,578 bytes in size.

BACKGROUND

The increasing technological push towards ultra-sensitive detection in biomolecular arrays—DNA, protein and carbohydrate—similarly requires extremely low background signals so that a high SNR can be attained. However, most commercially available chemical surface modifications usually have high auto-fluorescence or non-specific binding of reagents and analytes. This issue is increasingly crucial when the spot size of commonly used microarrays becomes smaller and smaller, even down to the sub-micron length scale. Although some of the current surface modification techniques work well for microarrays, the routine use of micro- and nano-arrays for biomolecules still poses substantial challenges in engineering a detection system that is capable of resisting non-specific adsorption of biomolecules down to the $pg/cm^2$ level and allows for direct detection of analytes without elaborate and expensive amplification techniques.

Current methods of screening for infectious diseases (IDs) suffer from several shortcomings including high cost, complexity of the assay, time required to perform the assay, and sensitivity of the assay.

Cost

The most accurate immunoassay-based test for a single infectious disease marker is known as the enzyme-linked immunosorbent assay (ELISA) that costs approximately $16 USD and requires on average 6 hours of technician time per marker tested. Recent improvements that enable multiplexing are now capable of testing for an array of four infectious agents at a cost of about $14 USD and requires on average about 4.5 hours of technician time. However, these tests require the use of approximately $110,000-$160,000 USD worth of laboratory equipment. Also, each test required the use of approximately 200 μL of serum or plasma, which can be separated from a sample of whole blood taken from a patient by a venous blood draw. This blood draw is generally taken at the point-of-care (POC) and then transported to a centralized laboratory for the actual test.

There remains a need in the art for a device that significantly reduces cost by streamlining the key aspects of sample collection, processing and testing. Ideally, such a device should provide: (1) elimination of all preprocessing by directly testing undiluted whole blood obtained from a finger stick; (2) test miniaturization to decrease the amount of reagents—the protein antigens that are spotted as capture agents and the detection antibodies; and (3) one-step, on-site processing. In addition, the test should be capable of being multiplexed and capable of targeting a panel of IDs without significantly increasing cost over that of a test for a single ID. These improvements should be accomplished without the use of sample preprocessing or the use of microfluidics to separate cells from the analyte solutions.

A multiplexed test would have further advantages. Much has been focused on the IDs that receive the greatest media attention, such as HIV, resulting in a general lack of desire or urgency for the general populace to be tested for other IDs. A suitable resolution to this issue is to provide a test for an entire panel of IDs whenever a single ID test is requested, which can result in only incremental cost relative to a test directed to a single ID. Miniaturization of the devices can reduce costs due to the use of picoliter quantities of the capture reagents and detection antibodies in the devices. Multiplexing could also help with the discomfort that some people experience when requesting a specific test for a stigmatized disease such as HIV, since it would be one of several IDs found on the chip. Having a multiplexed test that covers many IDs, including food and airborne IDs would allow individuals to feel less apprehensive about requesting testing. In addition, miniaturization of the device to reduce the amounts of capture agent needed, effectively eliminates one of the most significant costs in standard laboratory ID screening tests, such as plate-based ELISAs. Furthermore, by employing recently developed techniques of inkjet printing, disposable, multiplexed sensor chips can be manufactured at a cost on the order of several cents per chip.

Additional cost reductions may be achieved by reducing the dependence on a highly developed health care infrastructure. For example, traveling clinics in developing nations have limited time and personnel, and a multiplexed test with single-step, on-site processing significantly increases patient throughput and the number of infections detected. In addition, creating a miniaturized, multiplexed assay eliminates vast amounts of materials and significantly reduces the burden of transportation and storage.

Assay Simplicity and Time-to-Readout

People who have experienced an ID test note the anxious waiting period (often days to weeks) leading up to result notification as uncomfortable and a reason for avoiding future tests. More than 50% of patients do not return if a second visit is required to receive test results. Studies have also shown that up to 50% of patients will leave before receiving test results if wait time is 100 minutes, and approximately 20% of patients will leave if wait time is 50 minutes. A rapid test is needed to ensure that both the test and the result are provided during a single visit, thereby eliminating the need for patients to provide contact information for result notification (providing this information can lead to patient privacy concerns, another reason for test avoidance).

Tests requiring whole blood samples drawn by venipuncture require significant effort, time and the availability of highly skilled workers. In addition to the actual drawing of the blood sample, many diagnostics require that the blood be separated into cells and plasma. This requires additional equipment and expertise, increased assay cost and time-to-readout, and limits the ability to provide point-of-care diagnosis. Additionally, the process of venipuncture itself can lead to medical complications in the patients, and the strong aversion to that many individuals feel toward needles and venipuncture. All of these concerns can be reduced by creating a test that is capable of detecting a panel of IDs in only a few microliters of blood, which can be easily obtained via a finger-stick. In addition, by creating a test with the ability to detect multiple targets in only a few microliters of blood, increased access for the testing of neonates is possible, where drawing larger quantities of blood is problematic and often requires a blood transfusion at the time of the blood draw due to the quantity of blood required.

A device is needed that eliminates the need for expensive or complex microfluidics, which thereby reduces pre-chip cost and eliminates a major cause of failure so common to most contemporary "lab-on-a-chip" designs when they are actually field tested with clinical samples.

Higher throughput of ID testing can be achieved by reducing required materials (e.g., the elimination of needles and blood collection vials, as well as the concern of their proper disposal). In addition, the only disposable item created in the devices and methods of the present disclosure, other than the finger stick lancet, is a small piece of glass or plastic, which serves as the assay's blood contacting surface. Thousands of these could be disinfected with a single liter of bleach solution, and disposal of these surfaces could be in the regular trash. Additionally, testing in low resource settings often occurs in isolated regions. While bringing testing to these areas increases access, it is often the case that any type of follow up is non-existent or occurs only after long periods of time. In addition, face-to-face communication is often the only option, as other methods such as mail, telephone, or email are unavailable or unreliable. For these reasons, rapid results are essential. As mentioned above, options such as lateral flow strip-based tests are available for these situations, but their sensitivity is limited and the potential for multiplexed tests in this format is also limited.

Sensitivity

A novel device that addresses the issues described above should also provide the sensitivity found in standard laboratory tests, such as plate-based ELISA assays, with the advantages of inexpensive, handheld and rapid result lateral flow strip assays. Preferably such novel devices should achieve previously unattainable levels of sensitivity due to the elimination of the background noise in bioassays that arise from the adventitious adsorption of proteins.

Typically, the most sensitive assays require the support of a technologically sophisticated and capital-intensive healthcare infrastructure. Under current methods, patient samples taken at the point-of-care can be transported to a laboratory that maintains the equipment and personnel required to perform the actual test. Low resource settings simply do not have access to such facilities, which precludes these areas from having access to the most sensitive diagnostics. A novel device should offers on-site analysis, which allows the highly sensitive diagnostic to be utilized in settings where the healthcare infrastructure is less developed.

Even in countries where the infrastructure is not well developed, cell phones are becoming increasingly ubiquitous. This presents an opportunity to make use of cell phone technology to provide a novel diagnostic device. A cell phone based diagnostic device would be useful in a POC setting for two reasons: first it allows the cell phone to be repurposed as a fluorescence imaging detector and second, it allows the data to be communicated by the cell phone to a health care specialist at a remote site such as a clinic or hospital. If sufficient expertise exists at the POC, then the cell phone can simply be used to obtain an image of the data produced by the diagnostic device and to process the data to arrive at an analyte concentration that can be interpreted by the provider to arrive at a diagnosis. However, in instances where the test is self-administered by a patient or where the person administering the test is not a health care provider, the data can be sent via the cell phone to a health care provider located elsewhere who can then arrive at a diagnosis and prescribe treatment. This is especially useful for military personnel who are in remote locations.

These needs and others are met by the present invention. The present invention provides a chip that utilizes a unique protein and cell-resistant polymer brush that allows fluoro-immunoassays to be carried out with up to femtomolar limit-of-detection from whole blood. The polymer brush provides an inexpensive surface coating capable of eliminating the non-specific adsorption of biomolecules and cells. In addition, the protein-stabilizing property of the current disclosure enables transportation and storage of the chips in ambient temperatures, avoiding the need for costly climate-controlled storage and transport. The small volumes of sample required result in rapid performance of the assays described herein enabling results within a 5 minute period. Further, the devices and methods described herein also have the potential to make a significant impact on the ID screening of newborns, which is often required when either the mother's medical history is unavailable (e.g., in areas of war, famine, and strife), or the potential transmission of a known ID from mother to newborn can be investigated. Lastly, by relying on diffusion to bring together two spatially separated sets of reagents to generate a signal, the devices and methods described herein eliminate the need for washing or liquid transfer steps.

BRIEF SUMMARY

The inventive embodiments provided in this Brief Summary are meant to be illustrative only and to provide an overview of selective embodiments disclosed herein. The Brief Summary, being illustrative and selective, does not limit the scope of any claim, does not provide the entire scope of inventive embodiments disclosed or contemplated herein, and should not be construed as limiting or constraining the scope of this disclosure or any claimed inventive embodiment.

Provided herein is a chip comprising a channel therethrough and a non-fouling polymer layer contained in the channel, the channel being substantially enclosed within the chip. In some of the embodiments described herein, the chip can comprise a first substrate and a second substrate connected to the first substrate, with the channel displaced between the first substrate and the second substrate. In some of the embodiments described herein, the chip can fluffier comprise a means for adhering the first substrate to the second substrate. In some of the embodiments described herein, the first substrate or the second substrate can be comprised substantially of glass. In some of the embodiments described herein, the first substrate or the second substrate can be comprised substantially of plastic. In some of the embodiments described herein, the chip can further comprise a linking polymer layer positioned adjacent to and covalently attached to the non-fouling polymer layer. In some of the embodiments described herein, the linking polymer layer can link the non-fouling polymer layer to a substrate. In some of the embodiments described herein, the chip can be substantially transparent. In some of the embodiments described herein, the chip does not comprise an electronic component built into the chip. In some of the embodiments described herein, the chip does not comprise an individual, segregated well. In some of the embodiments described herein, the chip does not comprise a plasma extraction component. In some of the embodiments described herein, the chip can have only one channel. In some of the embodiments described herein, the chip can have two or more channels. In some of the embodiments described herein, the channel can be linear. In some of the embodiments described herein, the chip can be configured such that a sample can be introduced at either end of the channel. In some of the embodiments described herein, the chip does not contain a means for actively moving a sample through the channel. In some of the embodiments described herein, the chip does not contain a device for actively moving a sample through the channel. In some of the embodiments described herein, the chip can be barcoded. In some of the embodiments described herein, the chip is not barcoded. In some of the embodiments described herein, the non-fouling polymer layer can comprise a bottle brush polymer. In some of the embodiments described herein, the bottle brush polymer can comprise a kosmotrope head group. In some of the embodiments described herein, the bottle brush polymer can comprise a homopolymer of hydroxy terminated polymerized oligoethylene glycol methyl methacrylate (OEGMA), or a copolymer of methoxy-terminated OEGMA and hydroxy-terminated OEGMA. In some of the embodiments described herein, the non-fouling polymer layer can be about 10 to about 150 nm thick.

In some of the embodiments described herein, the non-fouling polymer layer can comprise at least one capture region comprising a capture agent that is directly, non-covalently bound to the non-fouling polymer layer. In some of the embodiments described herein, the position of the at least one capture region can be defined. In some of the embodiments described herein, the capture agent can preferentially bind to an analyte. In some of the embodiments described herein, the analyte can be or can comprise a surface antigen, a solution borne antigen, or a bound antigen. In some of the embodiments described herein, the analyte can be or can comprise a human B blood type antigen, a human A blood type antigen, a human Rh factor antigen, or any combination thereof. In some of the embodiments described herein, the capture agent can be a macromolecule. In some of the embodiments described herein, the capture agent can be an antibody or a fragment thereof. In some of the embodiments described herein, the capture agent can be or can comprise a polynucleotide antigen, a RNA antigen, a DNA antigen, a protein antigen, a peptide antigen, a carbohydrate antigen, an aptamer antigen an antibody antigen, a fragment thereof, or any combination thereof. In some of the embodiments described herein, the chip can comprise directly, non-covalently bound to the non-fouling polymer layer, a first capture agent that binds to an A blood type antigen, a second capture agent that binds a B blood type antigen and a third capture agent that binds a Rh factor antigen. In some of the embodiments described herein, first, second, and third capture agents can occupy separate, defined positions of the non-fouling polymer layer. In some of the embodiments described herein, first, second, and third capture agents can be individually, an antibody or a fragment thereof. In some of the embodiments described herein, at least one of the first, second, and third capture agents can be individually, an IgM antibody, an IgA antibody, or an IgG antibody. In some of the embodiments described herein, the chip can further comprise an anti-coagulant on the non-fouling polymer layer. In some of the embodiments described herein, the non-fouling polymer layer can comprise an anti-coagulant. In some of the embodiments described herein, the anti-coagulant can be directly, non-covalently bound to the non-fouling polymer layer. In some of the embodiments described herein, the anti-coagulant can occupy one or more separate, defined positions in the non-fouling polymer layer. In some of the embodiments described herein, the anti-coagulant can be heparin, a low molecular weight heparin, or a combination thereof. In some of the embodiments described herein, the chip can have a limit of detection (LOD) of an analyte of about 100 fg/ml. In some of the embodiments described herein, the non-fouling polymer layer can further comprise at least one labile region comprising a detection agent. In some of the embodiments described herein, the position of the at least one labile region can be defined. In some of the embodiments described herein, the detection agent can be not directly, non-covalently bound to the non-fouling polymer layer. In some of the embodiments described herein, the at least one detection agent can at least partially dissolve or disperse into a sample after contact with the sample. In some of the embodiments described herein, the sample can be a liquid containing at least one analyte. In some of the embodiments described herein, the liquid can be blood. In some of the embodiments described herein, the liquid can be plasma, serum, urine, sweat, or saliva. In some of the embodiments described herein, the detection agent can be a macromolecule. In some of the embodiments described herein, the detection agent can be a polynucleotide, RNA, DNA, a protein, a peptide, an aptamer, an antibody, a fragment thereof, or any combination thereof. In some of the embodiments described herein, the detection agent can be labeled. In some of the embodiments described herein, the detection agent can be a labeled antibody or fragment thereof. In some of the embodiments described herein, the detection agent can be labeled with a fluorophore, a chromophore, a radiolabel, a polynucleotide, a small molecule, an enzyme, a nanoparticle, a microparticle, or a quantum dot. In some of the embodiments described herein, the nanoparticle can be a noble metal nanoparticle. In some of the embodiments described herein, the non-fouling polymer layer can comprise an excipient. In some of the embodiments described herein, the excipient can be a water soluble salt, a carbohydrate, an emulsifier, a water-soluble polymer, or any combination thereof. In some of the embodiments described herein, the carbohydrate can be glucose, fructose, xylose, mannose, trehalose, galactose, sucrose, or lactose. In some of the embodiments described herein, the water-soluble polymer can be polyethylene glycol (PEG). In some of the embodiments described herein, the chip can comprise a first detection agent that binds to an A blood type antigen, a second detection agent that binds a B blood type antigen and a third capture agent that binds a Rh factor antigen. In some of the embodiments described herein, the first, second, and third detection agents can occupy separate, defined positions of the non-fouling polymer layer. In some of the embodiments described herein, the channel can be centrally located within the chip. In some of the embodiments described herein, the channel can have a volume of about 0.01 to about 500 µL. In some of the embodiments described herein, a detection agent can be located at downstream from a capture agent relative to the point of entry of an analyte into the chip. In some of the embodiments described herein, a capture agent and a detection agent can bind to the same analyte. In some of the embodiments described herein, a capture agent and/or detection agent can retain at least about 50% binding activity for at least about 2 months at a temperature of about 25° C., when the chip is stored such that the non-fouling polymer layer can comprise waters of hydration, but not bulk water. In some of the embodiments described herein, the chip can have a cylindrical shape. In some of the embodiments described herein, capillary action is capable of drawing a sample through the channel. In some of the embodiments described herein, the chip can be configured to be contained in and fully surrounded by a detector. In some of the embodiments described herein, the non-fouling polymer layer can run a length of the channel. In some of the embodiments described herein, the chip can further comprise a dam. Also provided herein is a detector. Also provided herein is a detector comprising a chip. Also provided herein is a method of making a chip. Also provided herein is a method of detecting the presence or absence of an analyte.

In some embodiments, the present invention provides a system for detecting an analyte. Typically, the system will comprise a chip, a detector, and a cell phone. Chips for use in the systems of the invention comprise a non-fouling polymer layer. Chips further comprise at least one of a capture agent and a detection agent disposed on the non-fouling polymer layer. In some embodiments, the capture agent is non-covalently attached to the non-fouling polymer layer. A system invention mat be used to detect any analyte. Examples of a suitable analyte include, but are not limited to, an analyte is or comprises: a human A blood type antigen; a human B blood type antigen; a human AB blood type antigen; a human O blood type antigen; a human Rh factor antigen; a glycophorin; a bio-threat agent; an antigen from an infectious agent; a cancer antigen; an antigen associated with cardiovascular disease; an antigen associated with a metabolic disease; any combination of the antigens listed above; or an antibody that recognizes any of the antigens listed above. In some embodiments, the detection agent comprises a flurophore and the detector comprises a light sources that emits a wavelength of light that excites the fluorophore. Systems of the invention may include any of the chips described herein in combination with any of the detectors described herein.

Also provided herein is a method of screening for a disease or a disorder in a subject. Also provided herein is a diagnostic assay for determining a disease, a disorder, or a biological state in a subject. In some of the embodiments described herein, an assay can be a point-of-care assay. Also provided herein is a kit.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls. The patents and patent applications incorporated herein by reference include at least U.S. Pat. Nos. 7,713,689, 8,367,314, US 20060057180, US 20090247424, US 20130157889, and US 20130143771.

BRIEF DESCRIPTION OF THE DRAWINGS

FIG. 25 provides schematics of one embodiment of a detector of the invention.

DETAILED DESCRIPTION

Figure 1:
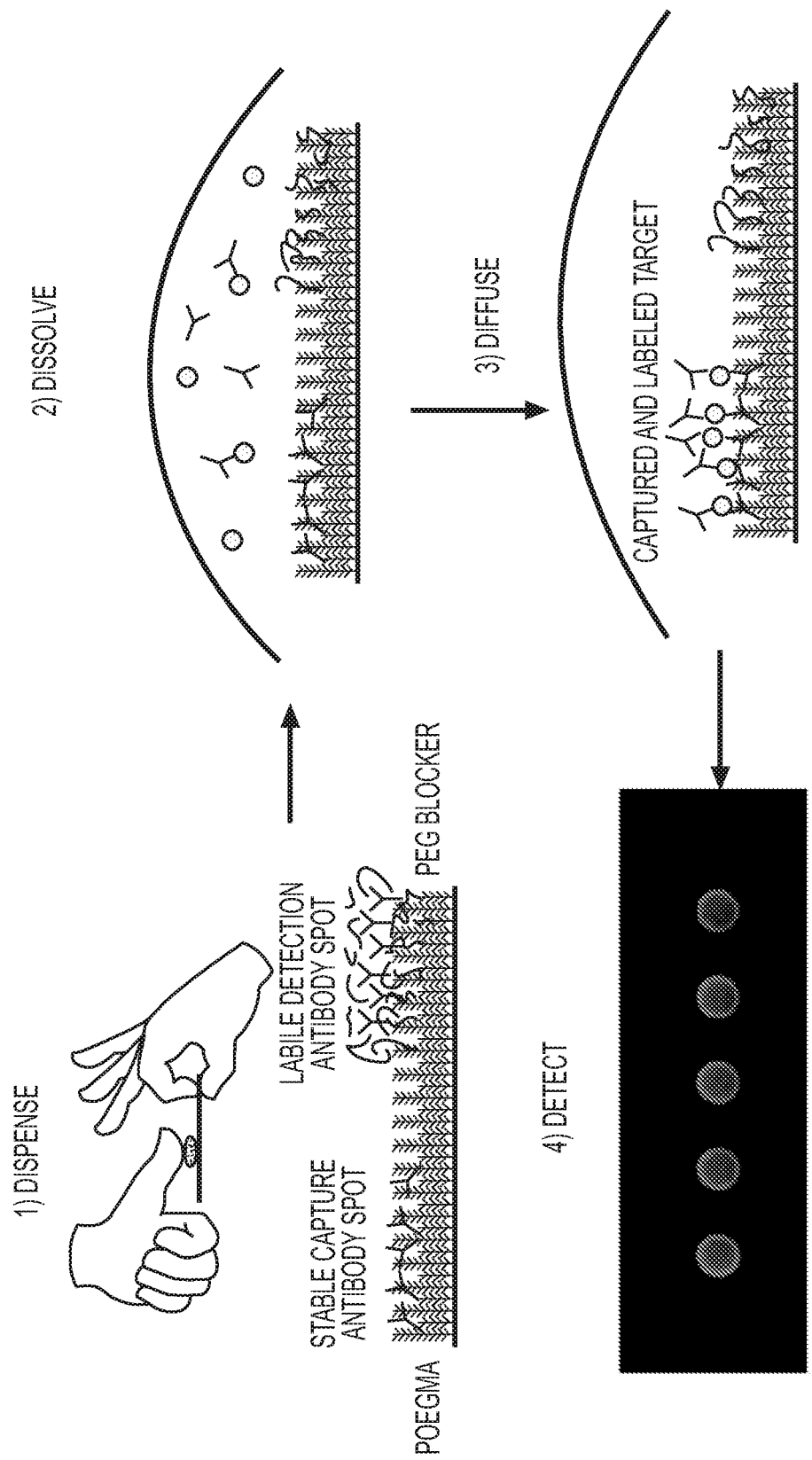
FIG. 1 illustrates design of a 2-D diffusion point of care (POC) assay on a poly oligo(ethylene glycol)methyl methacrylate (POEGMA) brush. Two types of spots are printed on the POEGMA brush coated chip: (1) "Stable" spots of capture antibody, which capture the analyte from blood and form the bottom half of the detection complex, and (2) "Soluble" spots of the detection antibody which diffuse from their printed spots upon contact with blood and form the labeled half of the detection complex.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

As used herein, unless otherwise indicated, open terms such as "contain," "containing," "include," "including," and the like mean "comprising."

As used herein, unless otherwise indicated, some embodiments herein contemplate numerical ranges. When a numerical range is provided, the range includes the range endpoints. Numerical ranges include all values and subranges therein as if explicitly written out.

The term "about" can refer to plus or minus 10-15% of a referenced numeric indication.

Articles "a," "an," and "the" are used herein to refer to one or to more than one (i.e. at least one) of the grammatical object of the article.

The term "and/or" as used herein should be understood to include any single element recited within the relevant phrase, as well as any combination of two or more elements, including all elements.

Unless otherwise defined, all technical terms used herein have the same meaning as commonly understood by one of ordinary skill in the art to which this disclosure belongs.

In some of the embodiments described herein, an analyte is or comprises a human A blood type antigen, a human B blood type antigen, a human AB blood type antigen, a human O blood type antigen, a human Rh factor antigen, a human MNS blood type antigen, a human P blood type antigen, a human PlPK blood type antigen, a human Lutheran blood type antigen, a human Kell blood type antigen, a human Lewis blood type antigen, a human Duffy blood type antigen, a human Kidd blood type antigen, a human Diego blood type antigen, a human Yt or Cartwright blood type antigen, a human Xg blood type antigen, a human Scianna blood type antigen, a human Dombrock blood type antigen, a human Colton blood type antigen, a human Landsteiner-Wiener blood type antigen, a human Chido/Rodgers blood type antigen, a human H blood type antigen, a human Hh/Bombay blood type antigen, a human Kx blood type antigen, a human Gerbich blood type antigen, a human Cromer blood type antigen, a human Knops blood type antigen, a human Indian blood type antigen, a human Ok blood type antigen, a human Raph blood type antigen, a human John Milton Hagen blood type antigen, a human I blood type antigen, a human 1i blood type antigen, a human Globoside blood type antigen, a human Gill blood type antigen, a human Rh-associated glycoprotein blood type antigen, a human Forssman blood type antigen, a human Langereis blood type antigen, a human Junior blood type antigen, or any combination thereof.

As used herein, the term "sample" or "biological sample" relates to any material that is taken from its native or natural state, so as to facilitate any desirable manipulation or further processing and/or modification. A sample or a biological sample can comprise a cell, a tissue, a fluid (e.g., a biological fluid), a protein (e.g., antibody, enzyme, soluble protein, insoluble protein), a polynucleotide (e.g., RNA, DNA), a membrane preparation, and the like, that can optionally be further isolated and/or purified from its native or natural state. A "biological fluid" refers to any a fluid originating from a biological organism. Exemplary biological fluids can include, but are not limited to, blood, serum, plasma, lymph fluid, bile fluid, urine, saliva, mucus, sputum, tears, cerebrospinal fluid (CSF), bronchioalveolar lavage, nasopharyngeal lavage, rectal lavage, vaginal lavage, colonic lavage, nasal lavage, throat lavage, synovial fluid, semen, ascites fluid, pus, maternal milk, ear fluid, sweat, and amniotic fluid. A biological fluid can be in its natural state or in a modified state by the addition of components such as reagents, or removal of one or more natural constituents (e.g., blood plasma). A sample or biological sample can be, for example, blood, plasma, lymph, viral, bacterial, a human sample, a diseased human sample, an animal sample, a disease animal sample, saliva, mucus, cerebral spinal fluid, synovial fluid, stomach fluid, intestinal fluid, cytoplasmic fluid, or other type of sample.

As used herein, the term "biomarker" refers to a substance that is associated with a biological state or a biological process, such as a disease state or a diagnostic or prognostic indicator of a disease or disorder (e.g., an indicator identifying the likelihood of the existence or later development of a disease or disorder). The presence or absence of a biomarker, or the increase or decrease in the concentration of a biomarker, can be associated with and/or be indicative of a particular state or process. Biomarkers can include, but are not limited to, cells or cellular components (e.g., a viral cell, a bacterial cell, a fungal cell, a cancer cell, etc.), small molecules, lipids, carbohydrates, nucleic acids, peptides, proteins, enzymes, antigens and antibodies. A biomarker can be derived from an infectious agent, such as a bacterium, fungus or virus, or can be an endogenous molecule that is found in greater or lesser abundance in a subject suffering from a disease or disorder as compared to a healthy individual (e.g., an increase or decrease in expression of a gene or gene product).

As used herein, the term "detection moiety" is any moiety or compound that is detectable by methods including, but not limited to, spectroscopic, photochemical, biochemical, immunochemical, chemical, electrochemical, radioactivity, and other physical means. A detection moiety can be detectable indirectly; for example, the detection moiety can be a moiety or compound that is a member of a specific binding pair, wherein the second member of the binding pair can include a detection moiety that can be detected directly. A non-limiting and known example of such a detection moiety is biotin, which can bind to avidin or streptavidin comprising a detection moiety such as a fluorophore. Exemplary detection moieties can include, but are not limited to, fluorophores, chromophores, radiolabels, polynucleotides, small molecules, enzymes, nanoparticles, and upconverters.

As used herein, the term "infectious disease" (herein abbreviated as ID) refers to those diseases that are caused by infectious agents including, but not limited to, microbes such as, for example, viruses, bacteria, archaea, planaria, amoeba, and fungi.

The term "polymer," as used herein, is given its ordinary meaning as used in the art, i.e., a molecular structure featuring one or more repeat units (monomers), connected by covalent bonds. The repeat units can all be identical, or in some cases, there can be more than one type of repeat unit present within the polymer. The term polymer is intended to encompass any type of polymer, including homopolymers, copolymers (e.g., random copolymers, block copolymers, graft copolymers, etc.), and blends, combinations and mixtures thereof. Polymers can be linear, branched, star-shaped, etc.

As used herein, the term "region" refers to a defined area on the surface of a material. A region can be identified and bounded by a distinct interface between two materials having different compositions.

"Specific binding pair" as used herein refers to two molecules that exhibit specific binding to one another, or increased binding to one another relative to other molecules. A specific binding pair can exhibit functional binding activity such as, for example, a receptor and a ligand (such as a drug, protein, or carbohydrate), an antibody and an antigen, etc.; or structural binding activity such as, for example, protein/peptide and protein/peptide; protein/peptide and nucleic acid; and nucleotide and nucleotide etc. Typically, one member of the binding pair can serve as a capture agent in the devices described herein, and the capture agent can bind to the second member of the binding pair, which can be present as an analyte in a sample such as a biological fluid. "Analyte" as used herein can be any second member of a specific binding pair, as described above. Typically the analyte is a constituent of, or found in, a sample such as a biological fluid. The analyte can be a biomarker as described above.

As used herein, the term "subject" and "patient" are used interchangeably and refer to both human and nonhuman animals. The term "nonhuman animals" can include all vertebrates, e.g., mammals and non-mammals, including but not limited to nonhuman primates, sheep, dog, cat, horse, cow, chickens, amphibians, reptiles, and the like. In certain embodiments, the subject is a human patient.

As used herein, tRNA means transfer RNA.
As used herein, rRNA means ribosomal RNA.
As used herein mRNA means messenger RNA.
As used herein siRNA means small interfering RNA.
As used herein miRNA means micro RNA.
As used herein, a DNA-RNA hybrid is a single stranded polynucleotide that contains both DNA and RNA. The DNA-RNA hybrid can be annealed e.g., to a polynucleotide probe.

As used herein, a selective probe may bind to more than one target RNA, but does not bind the target RNAs equally.

As used herein, a specific polynucleotide probe binds to only one target RNA.

Disclosed herein is a method of detecting a target RNA, comprising:
 a) annealing a target RNA to a polynucleotide probe;
 b) extending the annealed target RNA with at least one deoxyribonucelotide triphosphate to form an RNA-DNA hybrid;
 c) extending the RNA-DNA hybrid with at least one deoxyribonucelotide triphosphate to form an extended RNA-DNA hybrid; and
 d) detecting the presence of the target RNA by detecting the presence of the extended RNA-DNA hybrid.

The method can be conducted on a support, which can be a solid support. The method can be conducted on a layer or portion of the solid support that is associated with a polynucleotide probe.

The method can be used to diagnose a disease or condition when the presence of a target RNA associated with the disease or condition is detected. Without being limiting, the disease or condition can be, for example, human immunodeficiency virus (HIV), herpes simplex virus (HSV), herpes simplex virus-1 (HSV-1), herpes simplex virus-2 (HSV-2), human papillomavirus (HPV), human papillomavirus-16 (HPV-16), human papillomavirus-18 (HPV-18), hepatitis C virus (HCV), hepatitis B virus (HBV), hepatitis A virus (HVA), cytomegalovirus, tuberculosis, *Chlamydia*, gonorrhea, syphilis, Methicillin-resistant *Staphylococcus aureus* (MRSA), mumps, measles, cholera, typhoid fever, rheumatic fever, cancer, stroke, ischemic disease, cardiovascular disease, Lyme disease, rabies, influenza, Ebola, pregnancy, a fungal infection, a bacterial infection, polio, small pox, diabetes, diabetes type I, diabetes type II, a viral infection, an autoimmune disease, a neurodegenerative disease, and any combination thereof The amount of target RNA can be quantified.

The method can be conducted on an array or a microarray.

The method can be conducted on a medical device, which can comprise an array or a microarray.

Multiple target RNAs can be detected simultaneously. Controls can be included in the array or microarray. Two or more of the polynucleotide probes can be different when detecting multiple target RNAs. The solid support or medical device or array or microarray can contain, for example, about 5, about 10, about 50, about 100, about 500, about 1000, about 5000, about 10,000, about 20,000, about 50,000, or from about 1 to about 100,000, or at least 10, at least 100, at least 1000, at least 10,000, at least 100,000 polynucleotide probes. The polynucleotide probes can be, for example, printed on to the microarray so that the polynucleotide probes occupy defined positions on the array or microarray.

In some of the embodiments described herein, support, solid support, and medical devices can comprise a substrate layer and a non-fouling layer (e.g., comprising bottle brush polymer(s)), wherein the polynucleotide probe is associated with the non-fouling layer. The polynucleotide probe can be covalently or non-covalently associated. In some of the embodiments described herein, the non-fouling layer can be non-covalently or covalently associated with an anchor which is covalently or non-covalently associated with a tether which is covalently bonded to the polynucleotide probe. A spacer can be inserted between the tether and the polynucleotide probe. The spacer can be, for example, an amino acid. The amino acid can be, for example, covalently bound to both the tether and the polynucleotide probe. In this way, the polynucleotide probe, with and without the presence of a spacer, can be anchored to the non-fouling polymer layer but not covalently associated with the non-fouling layer and not directly-non-covalently associated with it as well. Such an association can be, for example, an indirect, non-covalent association.

The results of the detection of an analyte can be captured as data, for example, an image can be captured, and the data can be transmitted via a communication medium, for example, a telephone line, the internet, an intranet, a fax, a text, an email, or a letter.

The data can be, for example, a digital image that can be captured, for example, with a digital camera that can be, for example, incorporated into a cell phone e.g., a smart phone.

The inventors have surprisingly found that a target RNA, annealed to a polynucleotide probe, can be enzymatically elongated (e.g., can have DNA bases (deoxyribonucleotides) added) and that the resulting DNA-RNA hybrid, can be detected. The detection can occur, for example, without the use of reverse transcription of RNA to DNA, without amplification of DNA, and without sequencing of the DNA or target RNA.

The deoxyribonucleotides can be added, for example, to an overhanging (e.g., non-annealed) 3'end of a target RNA, where a portion of the target RNA can be annealed to a polynucleotide probe.

The target RNA can be derived or obtained from a biological sample. The biological sample can be lysed.

The target RNA can be synthetic and can be a sequence that is found in nature or a sequence that is not found in nature, or a fragment thereof.

A label can be a fluorescent dye. Fluorescent dyes can be detected in droplets in real time with high resolution, and the availability of many fluorescent dyes with distinct excitation and emission wavelengths allow monitoring many labels in one experiment. Sets of fluorescent dyes can be selected so as to allow for a simultaneous detection of more than one dye in the same reaction. A set of dyes that can be detected at the same time can include, but are not limited to, Cy3, Cy5, FAM, JOE, TAMRA, ROX, dR110, dR6G, dTAMRA, dROX, or any mixture thereof. Any of those dyes can be used individually or in any combination to practice an embodiment herein. A dye can allow for single molecule detection. A large number of fluorescent dyes have been synthesized, and are commercially available in different formats. This can include fluorescent dyes having a linker region and a hydrazine group that allows for coupling to RNA in a reaction with dialdehyde groups. For examples on such compounds refer to the catalog of Invitrogen. The present disclosure is not limited to the use of a specific fluorescent dye, but different dyes can be applied to the same effect. The linker region can consist of a carbon backbone, can contain sulfur atoms, ketone groups, or diethylene glycol groups, or dodecaethylene glycol groups. The length of the linker can vary where the backbone is a linear molecule of 1 to 20 atoms. A linker can contain groups of atoms that allow for selective removal of the label in a chemical reaction as, for example, disclosed in PCT Patent Publication No. WO2003/048387.

Non-limiting examples of labels can include, but are not limited to, 5-FAM (also called 5-carboxyfluorescein; also called Spiro(isobenzofuran-1(3H), 9'-(9H)xanthene)-5-carboxylic acid,3',6'-dihydroxy-3-oxo-6-carboxyfluorescein); 5-Hexachloro-Fluorescein; ([4,7,2',4',5',7'-hexachloro-(3',6'-dipivaloyl-fluresceinyl)-6-carboxylic acid]); 6-Hexachloro-Fluorescein; ([4,7,2',4',5',7'-hexachloro-(3',6'-dipivaloylfluresceinyl)-5-carboxylic acid]); 5-Tetrachloro-Fluorescein; ([4,7,2',7'-tetra-chloro-(3',6'-dipivaloylfluoresceinyl)-5-carboxylic acid]); 6-Tetrachloro-Fluorescein; ([4,7,2',7'-tetrachloro-(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-proprionic acid); Quasar®-670 dye (Biosearch Technologies); Cal Fluor® Orange dye (Biosearch Technologies); Rox dyes; Max dyes (Integrated DNA Technologies), tetrachlorofluorescein (TET), 4,7,2-trichloro-7'-phenyl-6-carboxyfluorescein (VIC), HEX, Cy3, Cy 3.5, Cy 5, Cy 5.5, Cy 7, tetramethylrhodamine, ROX, and JOE as well as suitable derivatives thereof. The label can be an Alexa Fluor dye, such as Alexa Fluor 350, 405, 430, 488, 532, 546, 555, 568, 594, 633, 647, 660, 680, 700, and 750. The label can be Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X. The label can be at the 5' end of a probe, 3' end of the probe, at both the 5' and 3' end of a probe, or internal to the probe. A unique label can be used to detect each different locus in an experiment, for example two termini of a target polynucleotide, such as mRNA.

Non-limiting examples of dye-hydrazides that can be used for labeling include Alexa Fluor®-hydrazides and salts thereof, 1-pyrenebutanoic acid-hydrazide, 7-diethylaminocoumarin-3-carboxylic acid-hydrazide (DCCH) Cascade Blue® hydrazides and salts thereof, biocytin-hydrazide, 2-acetamido-4-mercaptobutanoic acid-hydrazide (AMBH), BODIPY® FL-hydrazide, biotin-hydrazide, Texas Red®-hydrazide, biocytin-hydrazide, luminol (3-aminophthalhydrazide), and Marina Blue® hydrazide. Non-limiting examples of dye-ethylenediamines that can be used for labeling include 5-dimethylaminonaphthalene-1-(N-(2-aminoethyl))sulfonamide (dansyl ethylenediamine), Cascade Blue® ethylenediamine and salts thereof, N-(2-aminoethyl)-4-amino-3,6-disulfo-1,8-naphthalimide (*lucifer* yellow ethylenediamine) and salts thereof, N-(biotinoyl)-N'-(iodoacetyl) ethylenediamine, N-(2-aminoethyl)biotinamide, hydrobromide (biotin ethylenediamine), 4,4-difluoro-5,7-dimethyl-4-bora-3a,4a-diaza-s-indacene-3-propionyl ethylenediamine and salts thereof (BODIPY® FL EDA), Lissamine™ rhodamine B ethylenediamine, and DSB-X™ biotin ethylenediamine (desthiobiotin-X ethylenediamine, hydrochloride).

Non-limiting examples of dye-cadaverines that can be used for labeling include 5-dimethylaminonaphthalene-1-(N-(5-aminopentyl))sulfonamide (dansyl cadaverine), 5-(and-6)-((N-(5 aminopentyl) amino) carbonyl) tetramethylrhodamine (tetramethylrhodamine cadaverine), N-(5-aminopentyl)-4-amino-3,6-disulfo-1,8-naphthalimide and salts thereof (*lucifer* yellow cadaverine), N-(5-aminopentyl)biotinamide and salts thereof (biotin cadaverine), biotin-X cadaverine (5-(((N-(biotinoyl) amino) hexanoyl) amino) pentylamine and salts thereof, Texas Red® cadaverine (Texas Red® C5), 5-(((4-(4,4-difluoro-5-(2-thienyl)-4-bora-3a, 4a-diaza-s-indacene-3-yl) phenoxy) acetyl) amino) pentylamine and salts thereof (BODIPY® TR cadaverine), Oregon Green® cadaverine, Alexa Fluor® cadaverine, and 5-((5-aminopentyl) thioureidyl) fluorescein and salts thereof (fluorescein cadaverine).

Also disclosed herein is a use of surface initiated enzymatic polymerization (SIEP) for detection of RNA in a microarray format. This method can incorporate multiple fluorophores into a RNA strand using the sequential and complementary reactions catalyzed by e.g. yeast poly(A) polymerase (PaP) to incorporate deoxyadenosine triphosphate (dATP) at the 3'-OH of a target RNA molecule, followed by e.g., terminal deoxynucleotidyl transferase (TdT) to catalyze the sequential addition of a mixture of natural and fluorescent deoxynucleotides (dNTPs) at the 3'-OH of a RNA-DNA hybrid (e.g., an extended RNA-DNA hybrid). The 3'-end of RNA can be efficiently converted into DNA (~50% conversion) by polymerization of dATP using yeast PaP, and the short DNA strand appended to the end of the RNA by PaP acts as the initiator for the TdT catalyzed polymerization of longer DNA strands from a mixture of natural and fluorescently dNTPs that contains up to ~45 Cy3 fluorophores per 1 Kb DNA. Obtained is a ~2 pM limit of detection (LOD) and a 3-log linear dynamic range for hybridization of a short 21 base long RNA target to an immobilized peptide nucleic acid probe, while fragmented mRNA targets from four different full length mRNA transcripts yielded a ~10 pM LOD with a similar dynamic range in a microarray format.

Deoxyribonucleotide triphosphates contain a nitrogenous base which can be, for example, adenine, thymine, guanine, or cytosine.

Also disclosed herein is a device comprising a substrate comprising a surface; a non-fouling polymer layer on the surface; at least one capture region on the polymer layer, comprising at least one capture agent; and at least one labile region on the polymer layer, comprising at least one detection agent and an excipient; wherein the capture region and the labile region are spatially separated. The disclosure also provides for methods, assays, and kits that comprise the device. The non-fouling polymer layer can provide for the reduction of non-specific binding between sample components and the substrate and/or the polymer layer. The labile region on the polymer layer can allow for simplified methods and assays by reducing the necessary steps involved in a typical assay such as, for example, merely contacting the surface of the device with a sample and subsequently detecting any signal from the capture region, while still providing for highly sensitive detection limits. The devices and associated methods are highly adaptable to a number of settings, including research and clinical laboratories as well as large-scale point of care assays.

Substrates

A variety of different types of substrates can be used in accordance with the disclosure.

In some of the embodiments described herein, the substrate can comprise a surface that allows for the application of a polymer layer. In some of the embodiments described herein, the substrate can be a label-free optical or mass detector (e.g., a surface plasmon resonance energy detector, an optical wave guide, an ellipsometry detector, etc.) and the surface of the substrate is a sensing surface (e.g., a surface portion that would be in contact with a biological fluid). Examples of such devices can include but are not limited to those described in U.S. Pat. Nos. 6,579,721; 6,573,107; 6,570,657; 6,423,055; 5,991,048; 5,822,073; 5,815,278; 5,625,455; 5,485,277; 5,415,842; 4,844,613; and 4,822,135.

In some of the embodiments described herein, the substrate can be a biosensor, an assay plate, or the like. For example, the substrate can be an optical biosensor, such as those described in U.S. Pat. Nos. 5,313,264, 5,846,842, 5,496,701, etc. The substrate can also be a potentiometric or electrochemical biosensor, such as described in U.S. Pat. No. 5,413,690, or PCT Application WO98/35232. The substrate can be a diamond film biosensor, such as described in U.S. Pat. No. 5,777,372. Accordingly, the substrate can be organic or inorganic; can be metal (e.g., copper or silver) or non-metal; can be a polymer or nonpolymer; can be conducting, semiconducting or nonconducting (insulating); can be reflecting or nonreflecting; can be porous or nonporous; etc. For example, the substrate can comprise polyethylene, polytetrafluoroethylene, polystyrene, polyethylene terephthalate, polycarbonate, gold, silicon, silicon oxide, silicon oxynitride, indium, tantalum oxide, niobium oxide, titanium, titanium oxide, platinum, iridium, indium tin oxide, diamond or diamond-like film, etc.

The substrate can be a substrate suitable for "chip-based" and "pin-based" combinatorial chemistry techniques. All can be prepared in accordance with known techniques. See, e.g., U.S. Pat. Nos. 5,445,934, 5,288,514 and 5,624,711.

Substrates as described above can be formed of any suitable material, including but not limited to a material selected from the group consisting of metals, metal oxides, alloys, semiconductors, polymers (such as organic polymers in any suitable form including woven, nonwoven, molded, extruded, cast, etc.), silicon, silicon oxide, ceramics, glass, and composites thereof.

Polymers used to form substrates as described herein can be any suitable polymer, including but not limited to: poly(ethylene) (PE), poly(propylene) (PP), cis and trans isomers of poly(butadiene) (PB), cis and trans isomers of poly(isoprene), poly(ethylene terephthalate) (PET), polystyrene (PS), polycarbonate (PC), poly(epsilon-caprolactone) (PECL or PCL), poly(methyl methacrylate) (PMMA) and its homologs, poly(methyl acrylate) and its homologs, poly (lactic acid) (PLA), poly(glycolic acid), polyorthoesters, poly(anhydrides), nylon, polyimides, polydimethylsiloxane (PDMS), polybutadiene (PB), polyvinylalcohol (PVA), polyacrylamide and its homologs such as poly(N-isopropyl acrylamide), fluorinated polyacrylate (PFOA), poly(ethylene-butylene) (PEB), polystyrene-acrylonitrile) (SAN), polytetrafluoroethylene (PTFE) and its derivatives, polyolefin plastomers, and combinations and copolymers thereof, etc.

The substrate can optionally have an additional layer such as gold or an oxide layer formed on the surface of the substrate, for example, to facilitate the deposition of a polymer layer or a linking layer, as discussed further below.

Chips

Substrates for use in the present invention can be in the form of a chip. Typically, a chip of the invention will define a channel that extends at least partially into the interior of the chip. The channel may have one or more non-fouling polymer layers disposed on one or more of the channel surfaces. The channel may be open at one or both ends and is generally covered so as to form a tube that extends through the chip. In some embodiments, a chip of the invention may rely upon capillary action to draw a sample (e.g., a biological fluid such as blood) into the channel. Thus, a channel may have dimensions that support capillary action. In other embodiments, a chip of the invention may define an open well. In one embodiment, the chip is designed with a channel to accept blood from a fingerstick via capillary action. In such embodiments, the channel may be designed to hold volumes of a few microliters, for example, from about 0.5 microliter to about 100 microliters, from about 0.5 microliter to about 75 microliters, from about 0.5 microliter to about 50 microliters, from about 0.5 microliter to about 25 microliters, from about 0.5 microliter to about 10 microliter, from about 0.5 microliter to about 5 microliters, from about 1 microliter to about 100 microliters, from about 1 microliter to about 75 microliters, from about 1 microliter to about 50 microliters, from about 1 microliter to about 25 microliters, from about 1 microliter to about 10 microliter, from about 1 microliter to about 5 microliters, from about 2.5 microliters to about 100 microliters, from about 2.5 microliters to about 75 microliters, from about 2.5 microliters to about 50 microliters, from about 2.5 microliters to about 25 microliters, from about 2.5 microliters to about 10 microliter, or from about 2.5 microliters to about 5 microliters. In one embodiment, a chip of the invention may define a channel that has dimensions of approximately 4 mm wide, by 9 mm long, by 0.1 mm high (3.6 microliters). Typically, one or more surface of the channel will comprise one or more micro- or nano-spots. The spots may comprise one or more reagents that will be used in performance of assays of the invention. In one embodiment, spots may be used that are about 100 microns in diameter.

In one embodiment, a chip of the invention defines a channel having the dimensions recited above. On the bottom surface of the channel 100 micron diameter spots are disposed. The spots may have a center to center spacing of 200 microns. In embodiments of this type, a 4 mm×9 mm channel could hold roughly 900 of the 100 micron diameter spots. The channel dimensions, spot size, and/or spot spacing can be adjusted so as to accommodate a desired number of spots. A suitable number of spots may be from about 100 to about 10000 spots, from about 100 to about 7500 spots, from about 100 to about 5000 spots, from about 100 to about 2500 spots, from about 100 to about 1000 spots, 500 to about 10000 spots, from about 500 to about 7500 spots, from about 500 to about 5000 spots, from about 500 to about 2500 spots, or from about 500 to about 1000 spots. Each spot may be a different material, although duplicate spots are generally desirable for reproducibility.

In some embodiments, a chip of the invention may comprise one or more dams. Dams may be provided to separate one or more spots from one or more other spots. Dams may be water soluble and made out of any material known to those skilled in the art. Dams may be disposed on the chip between the capture agent and a detection agent. Dams may comprises a water-soluble salt, water-soluble sugar, a water-soluble polymer, or any combination thereof. Suitable examples of materials from which a dam may be constructed include, but are not limited to, a phosphate salt, a citrate salt, trehalose, polyvinyl alcohol, polyethylene glycol, or any combination thereof.

A dam may be disposed at any position on the channel of a chip. For example, a dam may be placed at the fluid entrance of the channel, at a point within the channel or at the end of the channel opposite the fluid entrance of the channel. A dam may be disposed across all or a portion of the width of the channel. In some embodiments, a chip may define a channel comprising a plurality of spots and also comprising a dam across the width of the channel.

A chip of the invention may be made using two glass coverslips separated by double sided tape to make a space between the chips thereby defining a channel. In assays of the invention that employ optical detection methods, e.g., fluorescence detection, any optically clear material could be used as substrate, including plastics.

Linking Layer

Depending on the choice of substrate and polymer, a linking layer can optionally be included between the substrate and the polymer layer. For example, a linking layer can be formed from a compound comprising an anchor group coupled (e.g., covalently coupled) to an initiator (e.g., directly coupled or coupled through an intermediate linking group). The choice of anchor group can depend upon the substrate on which the linking layer is formed, and the choice of initiator can depend upon the particular reaction used to form the non-fouling polymer as discussed in greater detail below.

The anchoring group can covalently or non-covalently couple the compound or linking layer to the surface of the substrate. Non-covalent coupling can be by any suitable secondary interaction, including but not limited to hydrophobic interactions, hydrogen bonding, van der Waals forces, ionic bonds, metal-ligand interactions, etc.

Examples of substrate materials and corresponding anchoring groups can include, for example, gold, silver, copper, cadmium, zinc, palladium, platinum, mercury, lead, iron, chromium, manganese, tungsten, and any alloys thereof with sulfur-containing functional groups such as thiols, sulfides, disulfides (e.g., —SR or —SSR where R is H, alkyl such as lower alkyl, or aryl), and the like; doped or undoped silicon with silanes and chlorosilanes (e.g., —SiR2Cl wherein R is H, alkyl such as lower alkyl, or aryl);

metal oxides such as silica, alumina, quartz, glass, and the like with carboxylic acids as anchoring groups; platinum and palladium with nitrites and isonitriles; and copper with hydroxamic acids. Additional suitable functional groups suitable as the anchoring group can include benzophenones, acid chlorides, anhydrides, epoxides, sulfonyl groups, phosphoryl groups, hydroxyl groups, phosphonates, phosphonic acids, amino acid groups, amides, and the like. See, e.g., U.S. Pat. No. 6,413,587.

Any suitable initiator can be incorporated into the anchoring group by introduction of a covalent bond at a location non-critical for the activity of the initiator. Examples of such initiators can include, but are not limited to, bromoisobutyrate, polymethyl methacrylate-Cl, polystyrene-Cl, AIBN, 2-bromoisobutyrate, chlorobenzene, hexabromomethyl benzene, hexachloromethyl benzene, dibromoxylene, methyl bromoproprionate. Additional examples of initiators can include those initiators described in U.S. Pat. No. 6,413,587 (e.g., at columns 10-11 thereof) and those initiators described in U.S. Pat. No. 6,541,580.

As noted above, a linking group or "spacer" can be inserted between the anchoring group and initiator. The linker can be polar, nonpolar, positively charged, negatively charged or uncharged, and can be, for example, saturated or unsaturated, linear or branched alkylene, heteroalkylene, aralkylene, alkarylene, or other hydrocarbylene, such as halogenated hydrocarbylene, particularly fluorinated hydrocarbylene. Suitable linkers can be saturated alkylene groups of 3 to 20 carbon atoms, i.e., $-(CH_2)_n-$, where n is an integer of 3 to 20 inclusive. See, e.g., U.S. Pat. No. 6,413,587. Another suitable embodiment of the linker is an oligoethyleneglycol of 3 to 20 units, i.e., $-(CH_2CH_2O)-$ where n is an integer of 3 to 20 inclusive.

The anchoring layer can be deposited by any suitable technique. It can be deposited as a self-assembled monolayer. It can be created by modification of the substrate by chemical reaction (see, e.g., U.S. Pat. No. 6,444,254) or by reactive plasma etching or corona discharge treatment. It can be deposited by a plasma deposition process. It can be deposited by spin coating or dip coating. It can be deposited by spray painting. It can also be deposited by deposition, printing, stamping, etc. It can be deposited as a continuous layer or as a discontinuous (e.g., patterned) layer.

In some of the embodiments described herein, the substrate can be glass, silicon oxide or other inorganic or semiconductor material (e.g., silicon oxide, silicon nitride) or compound semiconductors (e.g., gallium arsenide, and indium gallium arsenide) commonly used for microarray production. In some of the embodiments described herein, the substrate can be a microtiter (microwell) plate.

In some of the embodiments described herein, the anchoring group can be a silane or chlorosilane (e.g., $-SiR_2Cl$ wherein R is H, alkyl such as lower alkyl, or aryl).

In some of the embodiments described herein, the linking layer is formed on the substrate in two separate steps. For example, in a first step, an anchoring layer of alkylsilane or alkanethiol can be deposited on a surface such as silicon dioxide or glass or gold, and presents a terminal reactive functional group (e.g., amine) Subsequently, a bifunctional molecule, which comprises a first functional group reactive towards the terminal group presented by the first linking layer can be reacted with the first linking layer deposited in the first step. The second functional group of the bifunctional molecule contains a moiety group that acts as an initiator for the polymerization of the polymer layer, such as an ATRP initiator.

Polymer Layer

The polymer layers of the devices described herein exhibit non-fouling properties. Non-fouling, as used herein with respect to the polymer layer, relates to the inhibition (e.g., reduction or prevention) of growth of an organism as well as to non-specific or adventitious binding interactions between the polymer and an organism or biomolecule (e.g., cell, protein, nucleotide, etc.). The non-fouling property of the polymer can be introduced by any suitable method such as, for example, incorporation of a non-fouling (or alternatively, antifouling) agent or by the structure/architecture of the polymer itself Non-fouling agents are known in the art and can be selected by one of skill depending on the particular use of device, or on the availability of the non-fouling agent. Non-limiting examples can include organic and inorganic compounds having biocidal activity, as well as compounds that can be incorporated with or bound to the polymer layer that reduce or inhibit non-specific binding interaction of a biomolecule (e.g., cell, protein, nucleotide, carbohydrate/lipid) with the polymer upon contact.

Some embodiments provide a polymer layer having a structure or architecture that provides a non-fouling property. In some of the embodiments described herein, the polymer can suitably include brush polymers, which are, in general, formed by the polymerization of monomeric core groups having one or more groups that function to inhibit binding of a biomolecule (e.g., cell, protein, nucleotide, carbohydrate/lipid) coupled thereto. Suitably, the monomeric core group can be coupled to a protein-resistant head group.

Polymer layers can suitably be formed using radical polymerization techniques, such as catalytic chain transfer polymerization, iniferter mediated polymerization (e.g., photoiniferter mediated polymerization), free radical polymerization, stable free radical mediated polymerization (SFRP), atom transfer radical polymerization (ATRP), and reversible addition-fragmentation chain transfer (RAFT) polymerization.

For example, free radical polymerization of monomers to form brush polymers can be carried out in accordance with known techniques, such as described in U.S. Pat. Nos. 6,423,465, 6,413,587 and 6,649,138, U.S. Patent Application No. 2003/0108879, and variations thereof which will be apparent to those skilled in the art.

Atom transfer radical polymerization of monomers to form brush polymers can also be carried out in accordance with known techniques, such as described in U.S. Pat. Nos. 6,541,580 and 6,512,060, U.S. Patent Application No. 2003/0185741, and variations thereof which will be apparent to those skilled in the art.

Any suitable core vinyl monomer polymerizable by the processes discussed above can be used, including but not limited to styrenes, acrylonitriles, acetates, acrylates, methacrylates, acrylamides, methacrylamides, vinyl alcohols, vinyl acids, and combinations thereof.

In some of the embodiments described herein, the polymer layer can be formed by surface-initiated ATRP (SI-ATRP) of oligo(ethylene glycol)methyl methacrylate (OEGMA) to form a poly(OEGMA) (POEGMA) film. In an embodiment, the polymer layer is a functionalized POEGMA film prepared by copolymerization of a methacrylate and methoxy terminated OEGMA. Suitably, the POEGMA polymer can be formed in a single step.

In general, the brush molecules formed by the processes described herein (or other processes either known in the art or which will be apparent to those skilled in the art), can be from 2 or 5 up to 100 or 200 nanometers in length, or more, and can be deposited on the surface portion at a density of from 10, 20 or 40 to up to 100, 200 or 500 milligrams per meter, or more.

Protein resistant groups can be hydrophilic head groups or kosmotropes. Examples can include but are not limited to oligosaccharides, tri(propyl sulfoxide), hydroxyl, glycerol, phosphorylcholine, tri(sarcosine) (Sarc), N-acetylpiperazine, betaine, carboxybetaine, sulfobetaine, permethylated sorbitol, hexamethylphosphoramide, an intramolecular zwitterion (for example, $—CH_2N^+(CH_3)_2CH_2CH_2CH_2SO_3$) (ZW), and mannitol.

Additional examples of kosmotrope protein resistant head groups can include, but are not limited to:
—$(OCH_2CH_2)_6OH$;
—O(Mannitol);
—$C(O)N(CH_3)CH_2(CH(OCH_3))_4CH_2OCH_3$;
—$N(CH_3)_3{}^+Cl^-/$—$SO_3{}^-Na^+(1:1)$;
—$N(CH_3)_2{}^+CH_2CH_2SO_3{}^-$;
—C(O)Pip(NAc) (Pip=piperazinyl)
—$N(CH_3)_2{}^+CH_2CO_2—$;
—O([Glc-$\alpha$(1,4)-Glc-$\beta$(1)$^-$]);
—$C(O)(N(CH_3)CH_2C(O))_3N(CH_3)_2$;
—$N(CH_3)_2{}^+CH_2CH_2CH_2SO_3{}^-$;
—$C(O)N(CH_3)CH_2CH_2N(CH_3)P(O)(N(CH_3)_2)_2{}^-$; and
—$S(O)CH_2CH_2)_3S(O)CH_3$.

In some of the embodiments described herein, a suitable protein resistant head group can comprise poly(ethylene glycol) (PEG), for example PEG of from 3 to 20 monomeric units.

Prior to deposition of further components onto the polymer layer, the substrate with the optional linking layer and polymer layer can be dry or at least macroscopically dry (that is, dry to the touch or dry to visual inspection, but retaining bound water or water of hydration in the polymer layer). For example, to enhance immobilization of a capture agent, the polymer layer can suitably retain bound water or water of hydration, but not bulk surface water. If the substrate with the linking layer and polymer layer has been stored in desiccated form, bound water or water of hydration can be reintroduced by quickly exposing the polymer layer to water (e.g., by dipping in to water) and subsequently blow-drying the surface (e.g., with a nitrogen or argon jet). Alternatively, bound water or water of hydration can be reintroduced by exposing the polymer layer to ambient air for a time sufficient for atmospheric water to bind to the polymer layer.

Capture Region

The device comprises at least one capture region comprising at least one capture agent, which can be non-covalently bound to the polymer layer. The number of capture regions can vary widely and can depend on several factors including the size and shape of the substrate, the intended use of the device (e.g., a point-of-care diagnostic, a panel array (e.g., microarrays for screening DNA, MMChips (microRNAs), protein, tissue, cellular, chemical compounds, antibody, carbohydrate, etc.), and the like. The capture agent comprising a capture region is generally one member of a specific binding pair. Examples of suitable capture agents can include, but are not limited to, antigens, antibodies, peptides, proteins, nucleic acids, nucleic acid or peptide aptamers, ligands, receptors, and the like. Embodiments relate to a device comprising a plurality of capture regions that can comprise a plurality of different capture agents such as, for example, a diagnostic panel array.

In some embodiments, the capture agent can comprise a biomarker associated with any disease, disorder, or biological state of interest. Accordingly, the selection of the capture agent can be driven by the intended use or application of the device and methods described herein and can include any molecule known to be associated with a disease, disorder, or biological state of interest, or any molecule suspected of being associated with a disease, disorder, or biological state of interest. Thus, the selection of a capture agent is within the ability of one skilled in the art, based on the available knowledge in the art.

In some of the embodiments described herein, the capture agent can comprise a biomarker associated with any microbial infection of interest, examples of which can include but are not limited to: Anthrax, Avian influenza, Botulism, Buffalopox, Chikungunya, Cholera, Coccidioidomycosis, Creutzfeldt-Jakob disease, Crimean-Congo haemorrhagic fever, Dengue fever, Dengue haemorrhagic fever, Diphtheria, Ebola haemorrhagic fever, Ehec (*E. Coli* 0157), Encephalitis, Saint-Louis, Enterohaemorrhagic *Escherichia coli* infection Enterovirus, Foodborne disease, Haemorrhagic fever with renal syndrome, Hantavirus pulmonary syndrome, Hepatitis, Human Immunodeficiency Virus (HIV), Influenza, Japanese encephalitis, Lassa fever, Legionellosis, Leishmaniasis, Leptospirosis, Listeriosis, Louseborne typhus, Malaria, Marburg haemorrhagic fever, Measles, Meningococcal disease, Monkeypox, Myocarditis Nipah virus, O'Nyong-Nyong fever, Pertussis, Plague, Poliomyelitis, Rabies, Relapsing fever, Rift Valley fever, Severe acute respiratory syndrome (SARS), Shigellosis, Smallpox vaccine—accidental exposure, Staphylococcal food intoxication, Syphilis, Tularaemia, Typhoid fever, West Nile virus, Yellow fever, etc.

The capture agent can be deposited on the polymer layer by any suitable technique such as microprinting or microstamping, including piezoelectric or other forms of non-contact printing and direct contact quill printing. When the capture agent is printed on to the polymer layer, it can suitably be absorbed into the polymer layer such that it remains bound when the device is exposed to a fluid, such as a biological fluid. The brush polymer can also provide a protective environment, such that the capture agent remains stable when the device is stored. For example, in embodiments in which the capture agent is a peptide or protein, such as an antigenic protein or an antibody, a brush polymer layer can protect the capture agent against degradation, allowing the device to be stored under ambient conditions.

When an array is formed by the deposition of multiple capture agents at discrete locations on the polymer layer, probe densities of 1, 3, 5, 10, 100 or up to 1000 probe locations per $cm^2$ can be made. Modern non-contact arrayers can be used in the deposition step to produce arrays having up to 1,000,000 probe locations per $cm^2$. For example, using dip-pen nanolithography, arrays with up to 1 billion discrete probe locations per $cm^2$ can be prepared. It will be appreciated that the specific molecular species at each capture spot can be different, or some can be the same (e.g., to provide some redundancy or control), depending upon the particular application, as described herein.

The capture agent can be printed onto the polymer layer to form the capture region. The capture region(s) can be arranged in any particular manner and can comprise any desirable shape or pattern such as, for example, spots (e.g., of any general geometric shape), lines, or other suitable patterns that allow for identification of the capture region on the surface of the polymer and substrate. In embodiments, a plurality of capture agents can be arranged in a predetermined pattern such that the identity of the capture agent is associated with a specific location on the substrate.

Labile Region

The device additionally comprises at least one labile region comprising at least one detection agent and an excipient. In some of the embodiments described herein, a capture agent can remain non-covalently bound to the polymer layer (e.g., polymer brush) upon contact with a fluid such as a biological fluid, buffer, or aqueous solvent, while the excipient present in the labile region can absorb in to the polymer brush and block absorption of the detection agent. Accordingly, when exposed to an aqueous fluid such as, for example, a sample comprising a biological fluid, the detection agent can be solubilized and release in to the fluid, and can bind to an analyte of interest. The excipient can also further stabilize the detection agent during storage.

In some of the embodiments described herein, the detection agent can comprise a compound capable of binding to a second member of a specific binding pair. When solubilized and released in to the sample (e.g., a biological fluid), if the second member of the specific binding pair is present in the fluid, it can bind to the detection agent. The second member can then bind to the capture agent in the capture region of the device. Alternatively, the detection agent can encounter the second member of a specific binding pair when already bound to the capture agent. For example, if the capture agent is an antigenic protein and the analyte is a patient-generated antibody that can specifically bind the antigenic protein, the detection agent can comprise an anti-human antibody.

In some of the embodiments described herein, the labile region can comprise two different agents to form a "sandwich" type assay. In such embodiments, a first agent can bind to the analyte while the other agent binds to the first agent to form a "sandwich" which can then bind to the capture agent. For example, the detection agent can comprise biotin, which can bind avidin or streptavidin that is functionalized with a detection moiety.

The detection agent further comprises a detectable moiety that, directly or indirectly, provides a detectable signal. Exemplary detection moieties can include, but are not limited to, fluorophores, chromophores, radiolabels, polynucleotides, small molecules, enzymes, nanoparticles, and upconverters. In some of the embodiments described herein, the detection moiety can be a fluorophore such as a cyanine (e.g., CyDyes such as Cy3 or Cy5), a fluorescein, a rhodamine, a coumarin, a fluorescent protein or functional fragment thereof, or it can comprise a small molecule such as biotin, or it can comprise gold, silver, or latex particles.

In some of the embodiments described herein, the excipient can be a molecule or a combination of molecules that is selected as to allow for a stable, but non-permanent, association between the detection agent and the polymer. In embodiments the excipient can be partially soluble, substantially soluble or soluble in an aqueous solution (e.g., buffer, water, sample, biological fluid, etc.). In such embodiments, the excipient can be selected from the non-limiting examples of salts, carbohydrates (e.g., sugars, such as glucose, fucose, fructose, maltose and trehalose), polyols (e.g., mannitol, glycerol, ethylene glycol), emulsifiers, water-soluble polymers, and any combination thereof. Such excipients are well known in the art and can be selected based on the interaction between the excipient and detection agent, the excipient and the polymer, the solubility of the excipient in a particular medium, and any combination of such factors. In some of the embodiments described herein, the excipient can comprise PEG.

The detection agent and the excipient can be deposited on the polymer layer by any suitable technique such as microprinting or microstamping, including piezoelectric or other forms of non-contact printing and direct contact quill printing. A mixture of the detection agent and the excipient can be deposited simultaneously, or the excipient can be deposited prior to the detection agent.

When an array is formed by the deposition of multiple detection agents at discrete locations on the polymer layer, probe densities of 1, 3, 5, 10, 100 or up to 1000 probe locations per cm2 can be made. Modern non-contact arrayers can be used in the deposition step to produce arrays having up to 1,000,000 probe locations per cm2. For example, using dip-pen nanolithography, arrays with up to 1 billion discrete probe locations per cm2 can be prepared. It will be appreciated that the specific molecular species at each capture spot can be different, or some can be the same (e.g., to provide some redundancy or control), depending upon the particular application.

Other Elements

In some of the embodiments described herein, the device can further comprise an agent to demarcate a patterned region on the polymer layer, such that a fluid (e.g., a biological fluid) will remain confined to a specified region on the polymer layer such that it contacts the capture region and the labile region. Such an agent can be, for example, a hydrophobic ink printed on the polymer layer prior to the deposition of the capture agent and the components of the labile region. Alternatively, the agent can be a wax. In other embodiments, the sample can be contained or directed on the device through selection of an appropriate geometry and/or architecture for the substrate, for example, a geometry that allows the sample to diffuse to the regions comprising the capture agent and the components of the labile spot. In some of the embodiments described herein, the substrate can comprise a well, or a series of interconnected wells.

In some of the embodiments described herein, for example when the biological fluid is a blood sample, the labile region can comprise an anticoagulant to prevent the blood from clotting. Exemplary anticoagulants can include but are not limited to vitamin K antagonists such as coumadin, heparins, and low molecular weight heparins.

In some of the embodiments described herein, the device can further comprise regions printed with control agents. For example, when the detection agent comprises an anti-human antibody, control capture regions of human IgG can be printed alongside the capture regions to verify the activity of the anti-human detection antibody and to normalize the signal from the detection moiety, such as fluorescence intensities.

Device Storage

After deposition of the capture agent, detection agent, excipient and other optional components, the device is optionally dried, e.g., by mild desiccation, blow drying, lyophilization, or exposure to ambient air at ambient temperature, for a time sufficient for the article to be dry or at least macroscopically dry as described above. Once the device is dry or at least macroscopically dry, it can be sealed in a container (e.g., such as an impermeable or semipermeable polymeric container) in which it can be stored and shipped to a user. Once sealed in a container, the device can have, In some of the embodiments described herein, a shelf life of at least 2 to 4 months, or up to 6 months or more, when stored at a temperature of 25° C. (e.g., without loss of more than 20, 30 or 50 percent of binding activity).

Detection

Following exposure of a device described herein to a biological sample (e.g., a biological fluid), a signal from the detection agent can be detected using any suitable method known in the art. Exemplary methods can include, but are not limited to, visual detection, fluorescence detection (e.g., fluorescence microscopy), scintillation counting, surface plasmon resonance, ellipsometry, atomic force microscopy, surface acoustic wave device detection, autoradiography, and chemiluminescence. As one of skill in the art will appreciate, the choice of detection method will depend on the specific detection agent employed.

Detector

In some embodiments, the present invention provides a detector for use in the methods of the invention. A detector is typically configured to hold a chip and is equipped with one or more light sources. The light sources are configured to illuminate the chip. The light soured may illuminate the chip such that light passes through the chip. The light source may illuminate the chip such that light contacts a surface of the chip at an angle from about 0 degrees to about 90 degrees. In one embodiment, a light source may be positioned such that the light illuminates one surface of the chip and a non-fouling polymer layer disposed in a channel on the other side of the surface. In embodiments of this type the light may pass through on surface of the chip but not through the entire chip.

The light sources may be of any type, for example, may be LED lights. One suitable example of a light source for use in the present invention is a LED370F produced by Thor Laboratories. In some embodiments, a detector may comprise more than one light source, for example, may comprise 2, 3, 4, 5, 6, 7, 8, 9, 10, or more light sources. The light sources may be the same or different. Each light source may produce light of the same or different wavelength as light produced by another light source. Each light source may produce light of the same power. In one embodiment, 4 light sources are used each with a forward optical power of 2 mW. A detector of the invention will also typically comprise a lens. The lens is configured to collect light, e.g. light emitted by a fluorophone, and direct it to a camera of a smart phone.

Figure 25A:
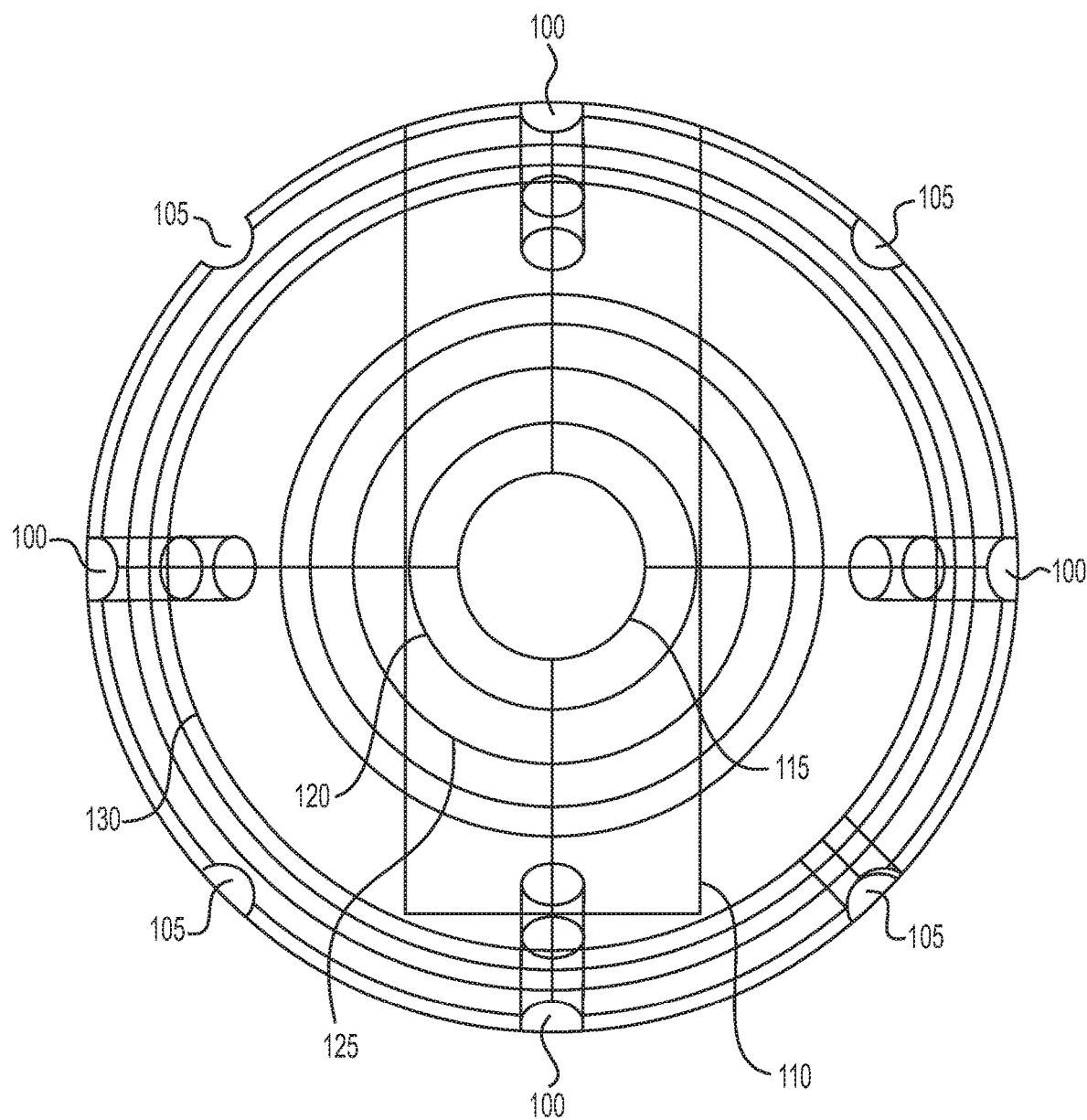
FIG. 25A is a schematic showing a top down view of the detector.
Figure 25B:
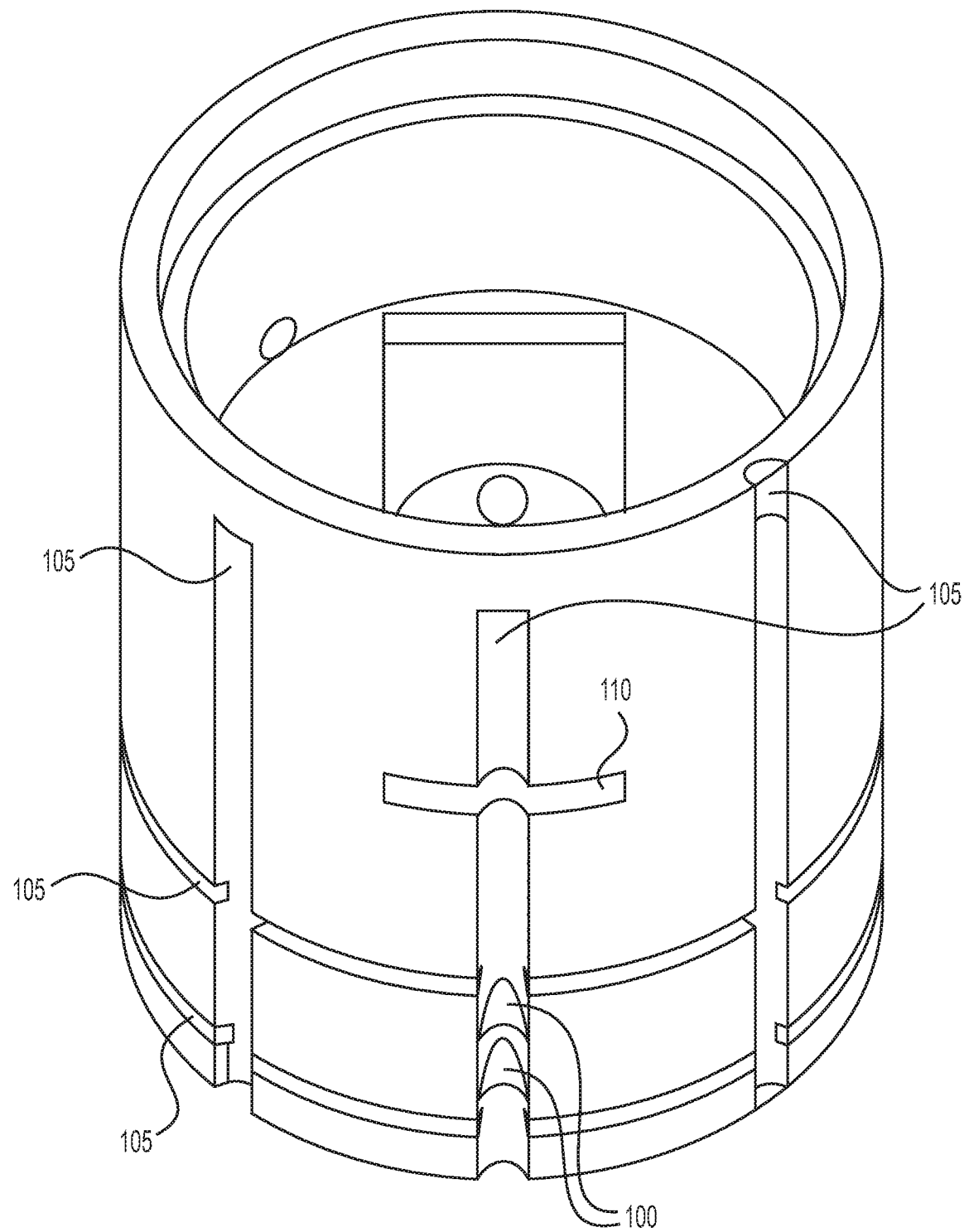
FIG. 25B is a top perspective view.
Figure 25C:
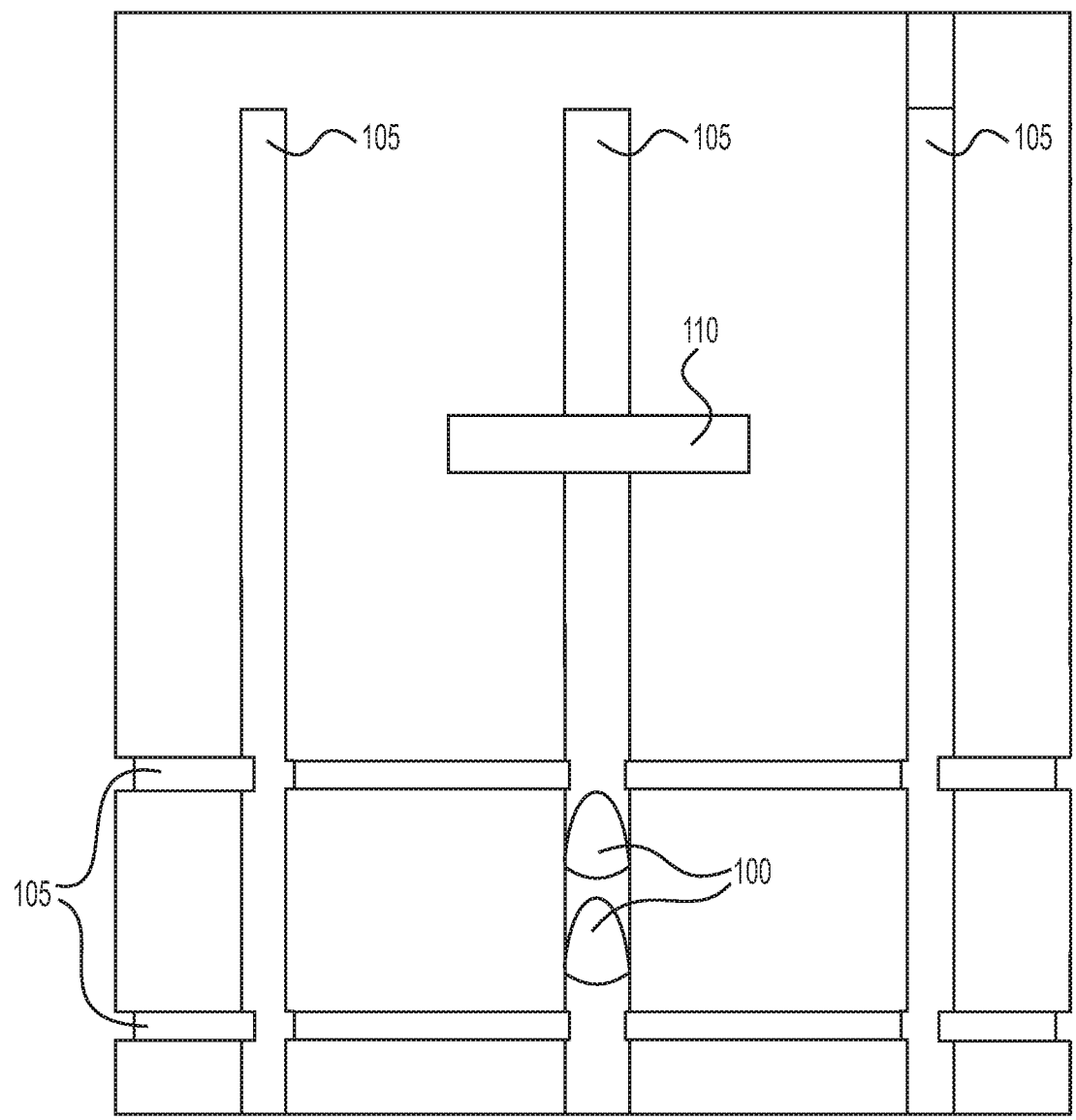
FIG. 25C is a side view.
Figure 25D:
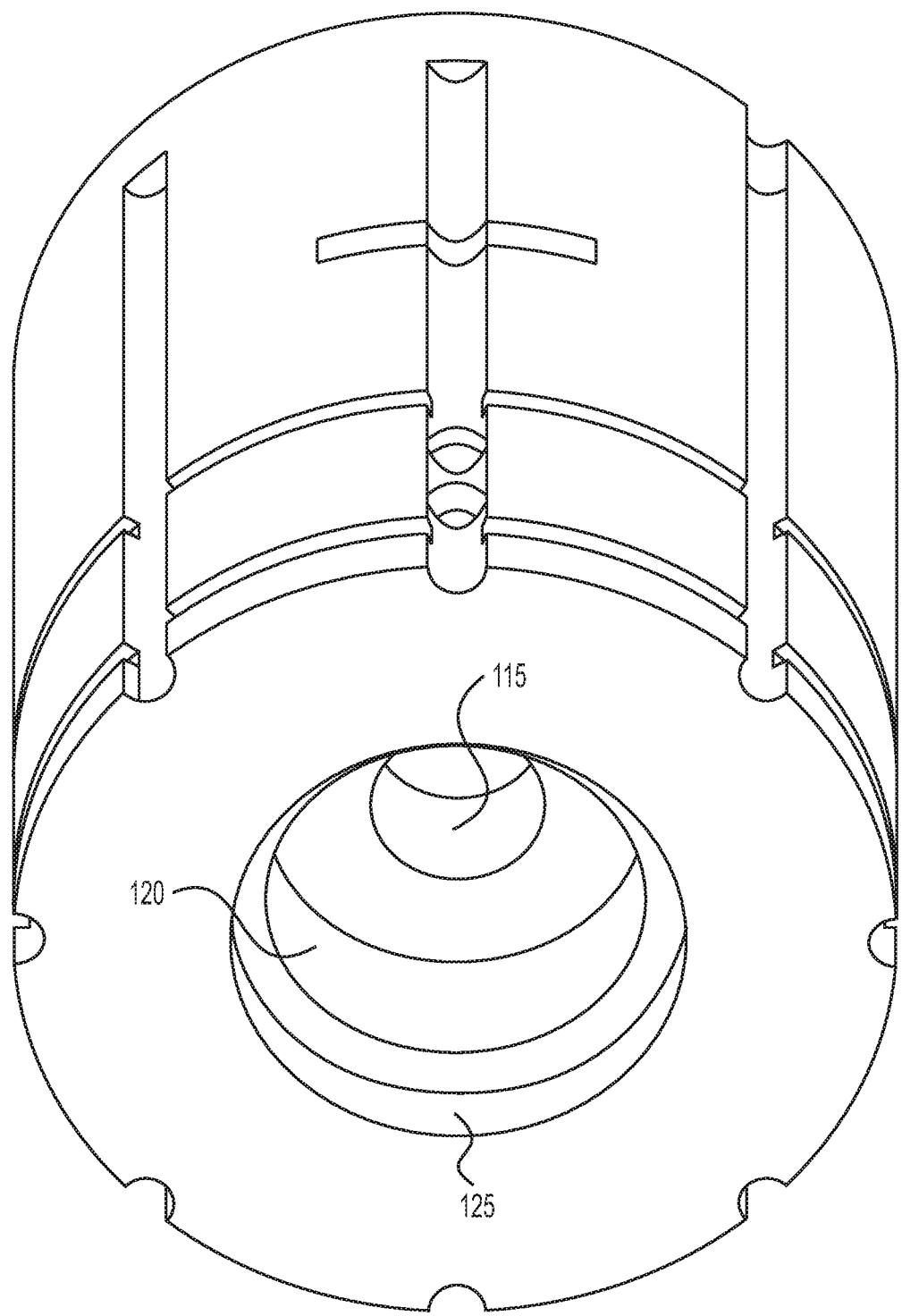
FIG. 25D is a bottom perspective view.
Figure 25E:
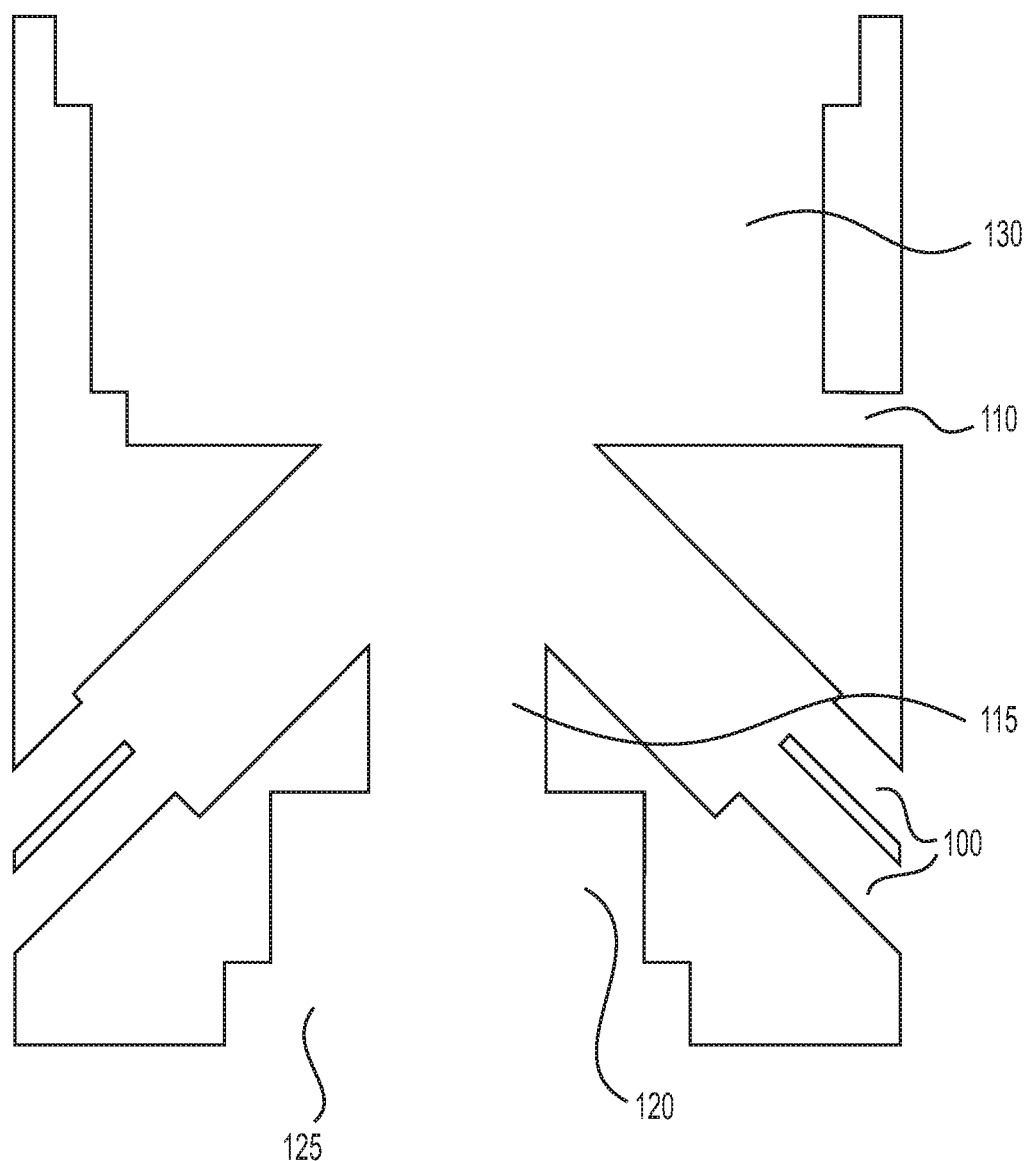
FIG. 25E is a cross sectional view along a plane through the long axis of the detector.

With reference to FIGS. 25A-25E, a detector of the invention may be generally cylindrical in shape and may comprise a central cavity that may extend through the detector along the central axis. A detector of the invention may alternatively be shaped so as to have a square or a rectangular cross section when bisected perpendicular to the long axis of the detector. The cavity may be shaped with various steps of varying shape and size to accommodate the chip, filter and lens. A detector of the invention have one or more LED channels 100. Such LED channels are sized so as to accommodate the LED lights referred to above. A detector of the invention may also comprise one or more wiring channels 105 that may be used to connect one or more power sources to the one or more LED lights. A detector of the invention may comprise one or more chip slots 110 configured to accommodate one or more chips of the invention. A chip slot may extend from the side of the detector into the interior and may or may not extend completely through the detector. In FIG. 25A, chip slot 110 extends from one side into the interior but not all the way through the detector. As discussed above, a detector of the invention may comprise a central cavity that extends along the central axis of the detector. As depicted in FIG. 25A, the cavity may provide a light path 115 such that light emitted from the chip may travel down the light path to a cell phone camera to be recorded by the camera. FIG. 25A also depicts a filter cavity 120. The filter cavity 120 is sized to accommodate a light filter designed to filter out one wavelength of light and allow another wavelength of light to pass through. For example, a filter may filter out light of a wavelength emitted by the LED lights referred to above and let pass a wavelength of light emitted by a detection agent. The filter will typically be disposed in the central light path. FIG. 25A also depicts a lens cavity 125. The lens cavity is sized to accommodate a lens for use in the present invention. A lens for use in the present invention will concentrate the light emitted from a detection agent and direct the concentrated light to a cell phone camera where the light may be recorded. FIG. 25A also depicts battery cavity 130. Battery cavity 130 is sized so as to accommodate a battery that is capable of powering the one or more LED lights referred to above. Typically, the battery cavity will be on the side of chip slot opposite that of the filter and the lens. The battery may be attached to or may be an integral part of the lid of the detector and, in such embodiments, the battery cavity may serve to accommodate the lid. A detector of the invention typically comprises a battery electrically connected to the light sources so as to provide the light sources with power. FIGS. 25B, 25C, and 25D show CAD views of a top perspective view, side view, and bottom perspective view, respectively, of a detector of the invention. FIG. 25E shows a cross sectional view of the a detector of the invention taken along a plane through the vertical axis of the detector.

A detector of the invention may comprise a magnetic portion designed to magnetically attach the detector to a cell phone.

Kits

Inventive embodiments herein can include kits.

Kits can comprise the supports, solid supports, and medical devices herein. Kits can include instructions, for example written instructions, on how to use the material(s) therein. Material(s) can be, for example, any substance, composition, polynucleotide, solution, etc., herein or in any patent, patent application publication, reference, or article that is incorporated by reference.

A kit can include a device as described herein, and optionally additional components such as buffers, reagents, and instructions for carrying out the methods described herein. The choice of buffers and reagents will depend on the particular application, e.g., setting of the assay (point-of-care, research, clinical), analyte(s) to be assayed, the detection moiety used, etc. For example, if the capture agent is a polynucleotide and the analyte of interest is a complementary polynucleotide, the kit can include a lysis buffer to be added to the sample of biological fluid, to make the polynucleotide from the sample available for binding.

The kit can also include informational material, which can be descriptive, instructional, marketing or other material that relates to the methods described herein and/or the use of the devices for the methods described herein. In embodiments, the informational material can include information about production of the device, physical properties of the device, date of expiration, batch or production site information, and so forth.

Exemplary Assay Design

The following paragraphs describe one non-limiting embodiment of the disclosure in more detail.

The disclosure provides a disposable chip that allows for miniaturized, multiplexed assays that can test a biological fluid for one or more IDs of interest. In some of the embodiments described herein, the assays can be conducted in one step. In certain embodiments, the assays can be conducted without the need for preprocessing or microfluidics. In addition to stable capture spots to bind biomarkers of interest, the devices can also include labile microspots that allow secondary detection agents to be printed alongside capture agents. Upon contact with a droplet of a biological fluid, these secondary reagents in the labile spots can dissolve into solution and label a target present in the sample.

In one embodiment of this technology, developed herein is a D4 point-of-care-test (POCT) that works from a single drop of whole blood (FIG. 2). The D4 POCT consists of a 30 nm thick "nonfouling"—protein and cell resistant—poly(oligoethylene glycol methacrylate) (POEGMA) brush coated glass chip (FIG. 2A) that contains two types of inkjet printed microspots contained within a central channel: "stable" spots of capture antibodies and "soluble" spots of detection antibodies that are printed with excipients so that they dissolve upon contact with blood. Capillary action is used to draw blood from a finger-stick into the central channel of the chip (FIG. 2B-E), and the protein analytes in the blood diffuse across the nonfouling POEGMA brush and bind to stable spots of capture antibodies on the surface (see FIG. 1).

Figure 2A:
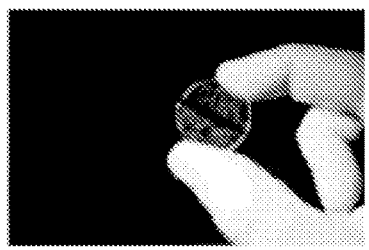
FIG. 2 illustrates D4 POC Test (D4=dispense, dissolve, diffuse, detect) workflow. (A) Microarray chip prior to blood introduction. (B-E) Introduction of blood from fingerstick via capillary action. (F) Connecting device to phone. (G) Inserting chip into device. (H) Placing cap on device. (I) Device ready for imaging with phone camera. (J) Phone image of microarray after addition of blood-backside imaging and illumination eliminates optical interference from blood. (K) Cutout schematic of detector design.
Figure 2F:
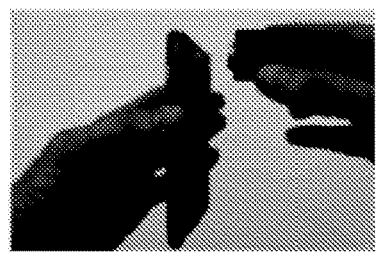
Figure 2B:
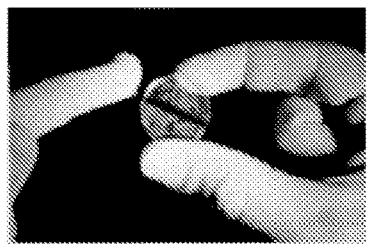
Figure 2G:
Figure 2C:
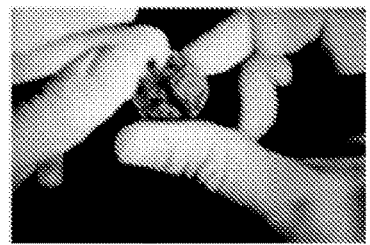
Figure 2H:
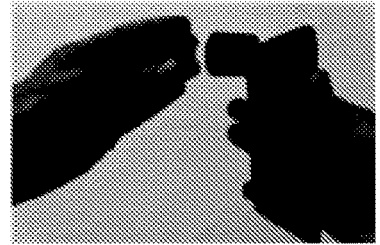
Figure 2D:
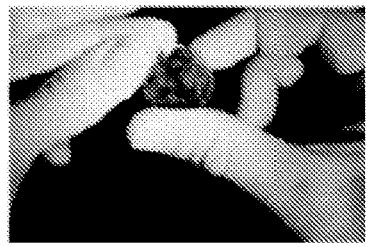
Figure 2I:
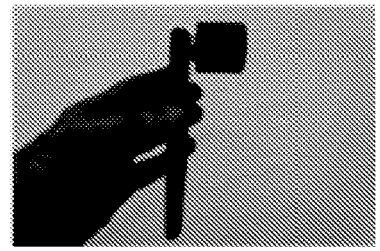
Figure 2E:
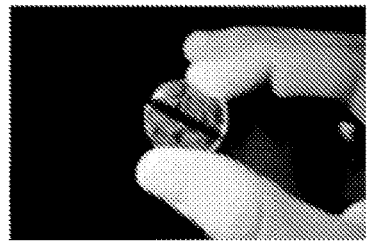
Figure 2J:
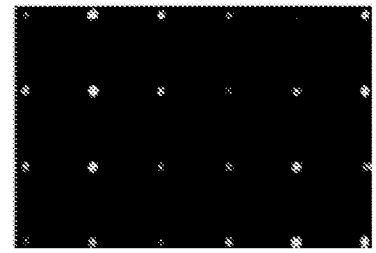
Figure 2K:
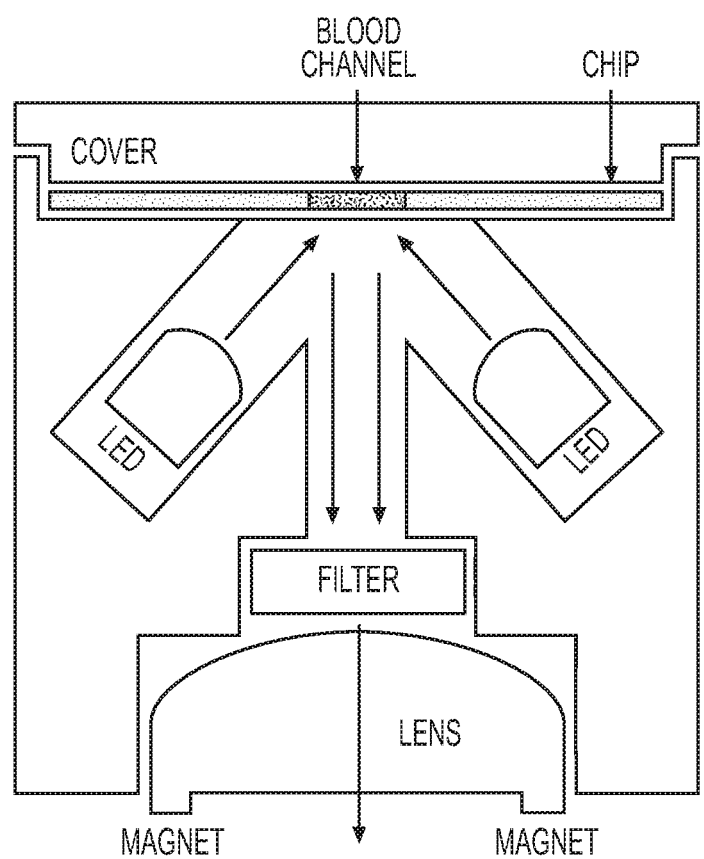

Simultaneously, the blood dissolves the fluorescently labeled detection antibodies from the soluble microspots, which diffuse and bind to their respective analyte-capture antibody spots, thereby completing the detection complex and generating a quantifiable fluorescence signal from the capture antibody spots (FIG. 1). This optical signal is imaged with a smart phone camera by placing the chip in a small device (FIG. 2K), which magnetically attaches to a smart phone (FIG. 2F-I). FIG. 2J is the resulting smart phone camera image of a test microarray printed within the chip's central channel in the presence of whole blood (image acquired after addition of whole blood to the channel). Backside optical illumination and detection eliminates optical interference from the blood, such that the drop of blood does not need to be removed for analysis, nor is any type of washing required for analysis (FIG. 2K).

In one embodiment of this technology, an assay according to the disclosure comprises, consists of, or consists essentially of a disposable chip which has been coated with POEGMA and then printed with a hydrophobic ink that demarcates a patterned region of POEGMA. The pattern region contains spots of individual capture agents. The hydrophilic nature of the POEGMA brush allows a droplet of blood to diffuse across the entire POEGMA surface while the hydrophobic ink creates a "corral" that can confine the blood droplet to the analysis region. The patterned region of POEGMA also contains "labile spots" which can include fluorescently-labeled detection antibodies, and soluble polyethylene glycol.

In some of the embodiments described herein, the capture agents in the capture spots can be antigens that are diagnostic for an ID of interest. When a sample of fluid (e.g., blood) from a patient is applied to the chip, patient-generated antibodies in the sample can bind to the antigen. In such embodiments, the labile spots can include fluorescently-labeled anti-human antibodies that can bind to the immobilized patient-generated antibodies.

In other embodiments, the capture agents in the capture spots can be antibodies to antigens that are diagnostic for an ID of interest. When a sample of fluid (e.g., blood) from a patient is applied to the chip, patient-generated antigens in the sample can bind to the antibody. In such embodiments, the labile spots can include fluorescently-labeled antibodies that are specific for a different epitope on the same antigen, which can bind to the immobilized patient-generated antigen.

In certain embodiments, the antigenic proteins or antibodies to be used as capture agents are spotted on the POEGMA surface as a row of individual spots of each antigen, in order to provide independent replicates and thereby improve robustness of the assay. For example, a microarray containing microspots of varying capture antibody density can allow a much broader range of analyte concentrations to fall within the dynamic range of a given detector, and can thereby eliminate the dilution series of tests usually run of a single sample. Low analyte concentrations can be detected in regions of high capture antibody density, while high analyte concentrations can be detected in regions of low capture antibody density.

In some of the embodiments described herein, arrays can be formatted in a manner to ensure that the detection antibody spots are dissolved upon contact with a blood sample. For example, twelve separate capture regions are printed as spots, with four spots each of three different capture agents. Labile regions including Cy5-labeled anti-human antibodies as detection agents are printed around the capture spots.

Soluble PEG can also be included in the labile spots. The soluble PEG can preferentially absorb into the POEGMA brush and block adsorption of the detection antibody into the brush. Accordingly, the detection antibodies, though confined in spots due to the Piezo inkjet printing and the macroscopic drying process, are in fact in a "labile" state in that they can be easily dissolved and released into the droplet of blood upon contact with an aqueous solution. The addition of excess soluble PEG can also stabilize the fluorescently-labeled detection antibody during storage, and can serve as an excipient that helps resolubilize the detection antibody when the test blood droplet is introduced.

Upon contact with a droplet of blood, the labeled detection antibodies will dissolve into solution. In some of the embodiments described herein, the detection antibody can be an anti-human antibody that can bind to, and thereby label, all human antibodies present in the blood sample. Concurrently, the analytes present in the blood, if present, (i.e., patient-generated antibodies against the antigens) can bind to stably printed antigen spots. In other embodiments, the detection antibody can be a specific antibody for an antigen of interest. Upon contact with the blood sample, if the antigen is present in the sample, the detection antibody can bind to the antigen, which in turn can bind to the capture agent antibody.

As positive controls, spots of human IgG can be printed alongside the antigen spots. These will serve to verify activity of the anti-human detection antibody and can also be used to normalize fluorescence intensities across assays to reduce inter-assay variability.

In order to prevent blood clotting, the enzyme heparin can also be printed onto the POEGMA brush in the labile spots. Heparin can be mixed with PEG prior to printing, or can be printed itself in a separate step.

In one embodiment, a finger-stick can be administered to the patient and the resulting droplet of blood applied to the chip surface. The hydrophobic ink printed onto the surface of the chip causes the blood droplet to spread across only the target(s) detection region, where it dissolves to soluble detection agents and heparin (to prevent clotting of blood) printed within the detection region.

As the solubilized, fluorescently labeled detection antibodies are dissolved from their printed spots by the droplet of blood, three serial events occur to generate a positive signal. These events can include the following: (1) binding of the analytes present in blood to the immobilized and non-fluorescent spots of the individual capture agents creates the first half of the sandwich; (2) diffusion of the blood laterally through the polymer brush results in the movement of soluble detection antibodies from their printed spots; (3)

upon entering a complex of capture agent and analyte (first half of sandwich), the fluorescently labeled detection antibodies bind to their respective analyte-capture agent spots, completing the sandwich and resulting in the formation of a fluorescent spot at the position where the unlabeled agent had been printed.

In this embodiment the assay is based on supported data that fluorescently labeled detection antibodies that are printed as "labile spots" are carried by flood flow to adjacent rows of printed, and stably immobilized, capture agents by diffusion of the solution containing the analyte. Hence, visualizing the appearance of fluorescence from the spots printed with the different capture agents provides unambiguous identification of different analytes (positives). Quantitation of the concentration of the different analytes is carried out identically to a conventional fluorescence immunoassay by pre-calibrating the device using a dilution series of the analytes spiked into whole blood.

The assay according to this embodiment addresses each of the critical needs in POC testing as follows: (1) the cost of ID testing will be reduced through miniaturization, multiplexing, one-step, on-site processing, and by testing directly in undiluted whole blood obtained from a finger stick with no preprocessing or microfluidics; (2) in order to simplify the ID screening process, diffusion in two-dimensions brings spatially localized reagents together to create a functional assay and thereby eliminating the need for liquid transfer steps, microfluidic manipulation of sample or reagents, and wash steps; (3) this multiplexed platform is capable of screening for a panel of ID markers with a single drop of blood with no sample preprocessing; (4) the assay will be fast, which will alleviate the difficulties often associated with communicating the outcome of the ID test; and (5) the actual detection scheme of the disclosed design is a sandwich-type fluorescent immunoassay, which offers the highest sensitivity currently available in the field.

An improvement in ID screening of this magnitude has the potential to substantially affect the health of the entire human population. In order to control infectious diseases, one part of the process is regular screening to identify the various pathogens transmitted through air, food, water, or physical contact, and it is believed that developing the proposed screening platform will make regular and comprehensive ID screening far more accessible to a much larger percentage of the population. Finally, the highly adaptable and modular design is useful in deployment as a diagnostic for many other areas of need as well, including monitoring of biomarkers in clinical trials, pandemic screening, biodefense, and large-scale verification of newly discovered biomarkers.

The following non-limiting Examples are intended to be purely illustrative, and show specific experiments that were carried out in accordance with the disclosure.

EXAMPLES

Example 1. POEGMA Brushes can be Grown on Glass and Plastics

Figure 3:
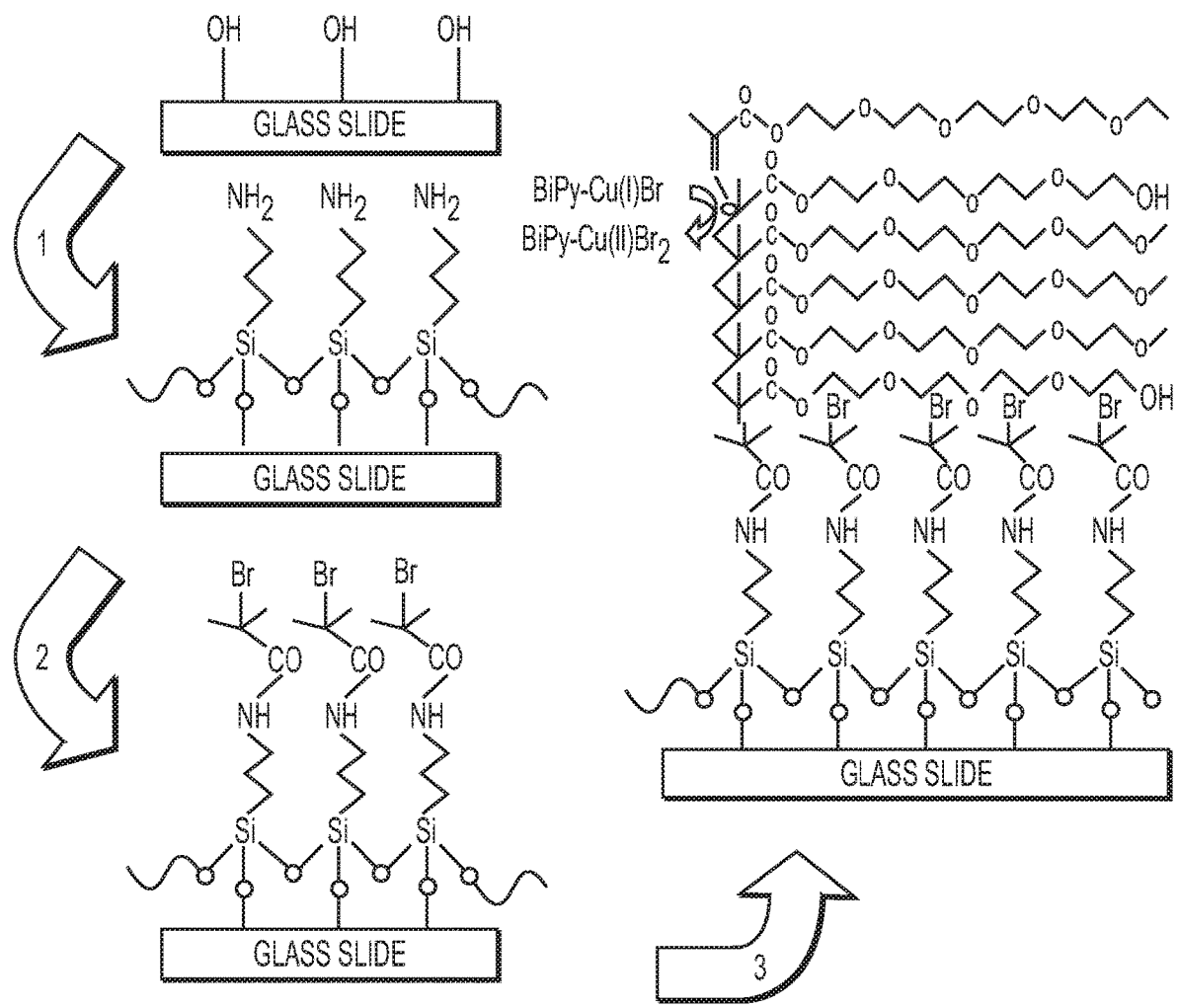
FIG. 3 illustrates synthesis of POEGMA brushes on glass by SI-ATRP. Cleaned glass slides are functionalized with APTES in step 1, and the amine groups in the silane monolayer are used to attach an ATRP initiator in step 2. Slides are then immersed in a solution of OEGMA monomer and catalyst to grow POEGMA brushes on the slide by SI-ATRP.

A protein- and cell-resistant coating of poly(oligoethylene glycol methacrylate) (POEGMA) with high chemical stability was developed. The POEGMA brushes are synthesized by surface initiated atom transfer radical polymerization (SI-ATRP) on glass, as shown in FIG. 3: first, an amine-terminated silane monolayer is formed on the glass surface by aminopropyltriethoxysilane (APTES) (step 1), followed by attachment of the ATRP initiator-bromoisobutyryl bromide—to the amine groups presented by the APTES monolayer (step 2), and subsequent ATRP from a solution that contains CuBr, bipyridine and the OEGMA monomer (step 3). This procedure allows the convenient synthesis of ~100 nm thick brushes that can be useful for printing Ab's and other proteins for immunoassays. Also developed is a complementary set of technologies that enable the growth of POEGMA brushes on a range of transparent thermoplastics that are also suitable as substrate materials for the D4 assay (Data not shown). These results show that a number of complementary approaches can be used to grow POEGMA brushes on materials that provide useful substrates for clinical immunoassays. These protein- and cell-resistant POEGMA brushes can form the basis of the D4 POCT as they prevent binding of cells to the chip and non-specific adsorption of proteins to the surface.

Exemplary coating of glass slides. Slides are treated with 5% (v/v) APTES in ethanol, overnight at room temperature. These slides are then treated with 2% bromoisobutyryl bromide (BIB) in 2% triethyamine (v/v) in dichloromethane then placed in a 100 mL flask under N2. Next, CuBr (143 mg, 1.0 mmol), bipyridine (312 mg, 2.0 mmol), dichloromethane (15 mL), and OEGMA (8 g, 16.7 mmol) were mixed in a 50 mL flask, and the dark red solution was bubbled with N2 gas for 30 min. The polymerization was initiated by adding the mixture to the slide-containing flask and was continued for one hour under nitrogen purge. The slides were removed from the solution to stop the polymerization, rinsed with dichloromethane and methanol, and dried under a stream of N2 gas for 10 minutes at room temperature.

Example 2. Antibodies can be Directly Printed on POEGMA Brushes by a Piezo-Inkjet Printer Capture antibodies (Abc) were printed as ~150 μm diameter spots on a 100 nm thick POEGMA brush at room temperature and humidity using a PerkinElmer Piezorray™ noncontact printer (FIG. 4A) and were allowed to non-covalently absorb into the 100 nm thick polymer brush. A ~100 nm thick POEGMA brush was chosen because it provides excellent resistance to protein adsorption in the hydrated state, but in the dry state acts as an ink reservoir: piezoelectrically printed antibody "ink" is avidly adsorbed into the brush to provide a high enough loading density of the Abc for use in microarray assays. After printing, the slides were dried in a vacuum dessicator at room temperature overnight to further promote the absorption of the Abc into the polymer brush. This step can be necessary as proteins will not adsorb on the polymer brush from solution. The POEGMA coated glass slides could be stored in a closed container and left on the bench-top for up to two months, with no adverse effect on the performance of antibody arrays that were subsequently printed on the polymer brushes. Direct inkjet printing—with no covalent coupling steps—can provide a simple method for fabrication of antibody arrays with minimal processing steps as inkjet printers are low cost and ubiquitous. This can provide a simple and scalable manufacturing technology for the D4 chips that can be easily deployed in a LMIC setting.

Exemplary Spotting of Antibody Microarrays: All capture antibodies and the biotinylated detection antibodies for the following analytes were obtained from R&D Systems: IL-6, human Interleukin-1b (IL-1b), human tumor necrosis factor (TNF-a), human interleukin-8 (IL-8), and OPG. All capture antibodies (0.5 mg/mL in PBS) were spotted using a noncontact PerkinElmer Piezorray onto POEGMA brushes on glass at room temperature and humidity, and allowed to noncovalently absorb into the 100 nm thick polymer brush under vacuum dessication (30 KPa) at room temperature overnight.

Example 3. Antibody Arrays on POEGMA Brushes are Highly Sensitive

Figure 4A:
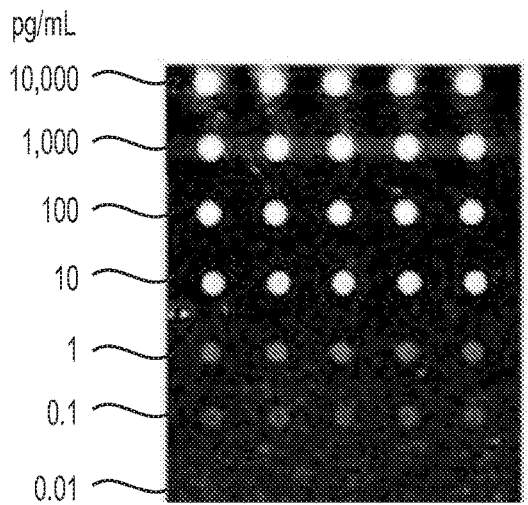
FIG. 4 illustrates (A) Image of a typical IL-6 microarray interrogated from serum. (B) Dose response curves of OPG in buffer and serum on POEGMA brush. (C) Dose response curves of IL-6 in serum on POEGMA brush and nitrocellulose. (D) Dose response curve for an IL-6 microarray interrogated from whole blood. In B-D, the ordinate shows the average background subtracted fluorescence intensity in spots and the X-axis shows analyte concentration in solution. Error bars are one standard deviation.
Figure 4B:
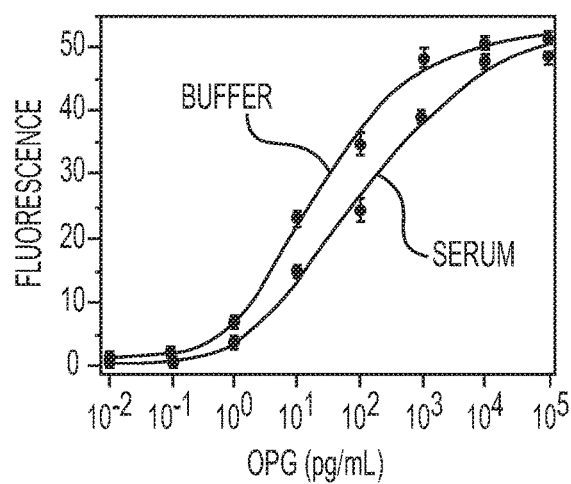
Figure 4C:
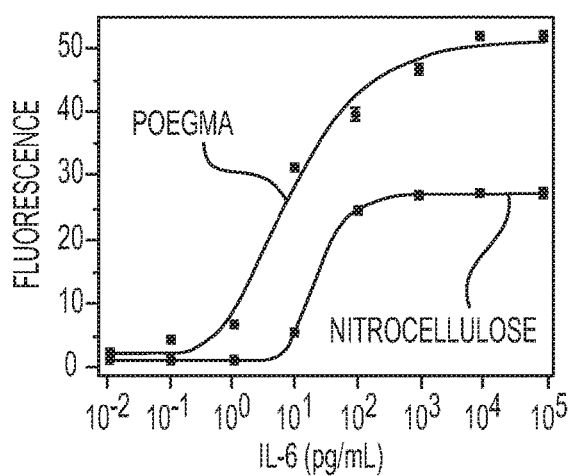
Figure 4D:
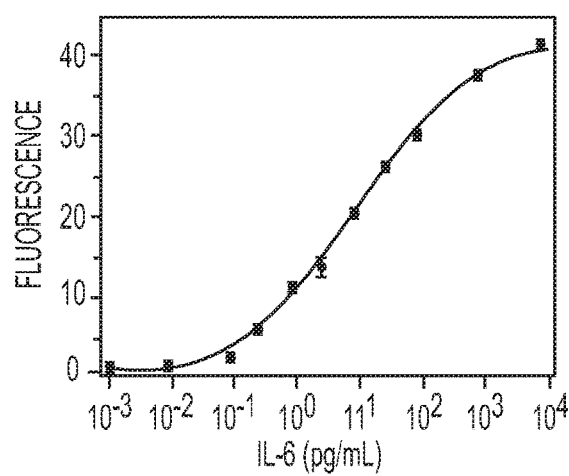

An antibody array specific for IL-1β, IL-6, IL-8, TNF-α and osteoprotegerin (OPG) was directly printed by a Piezorray inkjet printer onto: (1) a 100 nm thick POEGMA brush grown by SI-ATRP on glass, and (2) on unmodified nitrocellulose substrates (positive control). A fluorescence image of microarray spots for an IL-6 assay spotted on POEGMA on glass, shown in FIG. 4A, shows the increase in fluorescence intensity with increasing analyte concentration. Remarkably, spots could be visually discriminated from background even at an IL-6 concentration of 0.1 pg/mL (5 fM). FIG. 4A also shows that the POEGMA matrix retained its ability to resist non-specific protein adsorption throughout array fabrication and the subsequent sandwich immunofluorescence assay, as the fluorescence intensity in the background areas surrounding spots measured prior to the assay showed no increase in intensity upon completion of the procedure; in fact, the only background fluorescence detected on the POEGMA substrates was due to the autofluorescence of the glass slide. This extraordinarily low background signal on POEGMA translates to femtomolar limits of detection (LODs) in serum for all five analytes that were tested, and a dynamic range that spans five orders of magnitude of analyte concentration (FIG. 4B-D).

The OPG dose response curves in buffer and serum for OPG-specific antibodies spotted on POEGMA (FIG. 4B) illustrates another important consequence of the use of a protein resistant substrate, as they show that the LODs are virtually identical in buffer and serum. These results are in contrast to most other fluorescence immunoassays, where the LOD is typically orders of magnitude greater in complex physiological solutions containing high concentrations of extraneous proteins compared to the LOD for the same assay in buffer. Although the absolute signal from the spotted arrays on POEGMA was lower than that obtained from arrays spotted on nitrocellulose (raw data not shown), the background signal obtained from the POEGMA brush (which approached the autofluorescence levels of the glass substrate) was significantly lower than that from nitrocellulose. The fluorescence response of an IL-6 specific antibody array spotted on nitrocellulose and POEGMA as a function of IL-6 concentration in serum are shown in FIG. 4C. The LODs in serum for arrays spotted on POEGMA brushes were 100-fold lower than the same antibody microarrays on nitrocellulose, which clearly demonstrated that despite the lower absolute signal from the antibody arrays spotted on the POEGMA brush versus nitrocellulose, the significantly lower background fluorescence on the POEGMA brush more than compensated for the lower absolute signal from the spots. It was observed that antibodies to IL-6 spotted on a POEGMA brush on glass could detect IL-6 directly from undiluted blood with a LOD of ~15 fM (FIG. 4D).

These results demonstrate that the reduction of non-specific protein adsorption is a powerful method to decrease the LOD by dropping the threshold of noise in the dose-response curve of these assays to concentrations in the femtomolar range. Because these microarrays were physically spotted on POEGMA and did not involve any covalent coupling of the capture antibody to the substrate, they have the potential to greatly simplify fabrication of the assay by eliminating the need for chemical activation and deactivation of the surface. The ability of these microarrays to resist the adsorption of proteins and cells from solution enables the detection of analytes directly from whole blood. These features are critical to the design of the D4 POCT that works in blood with high sensitivity.

Figure 5:
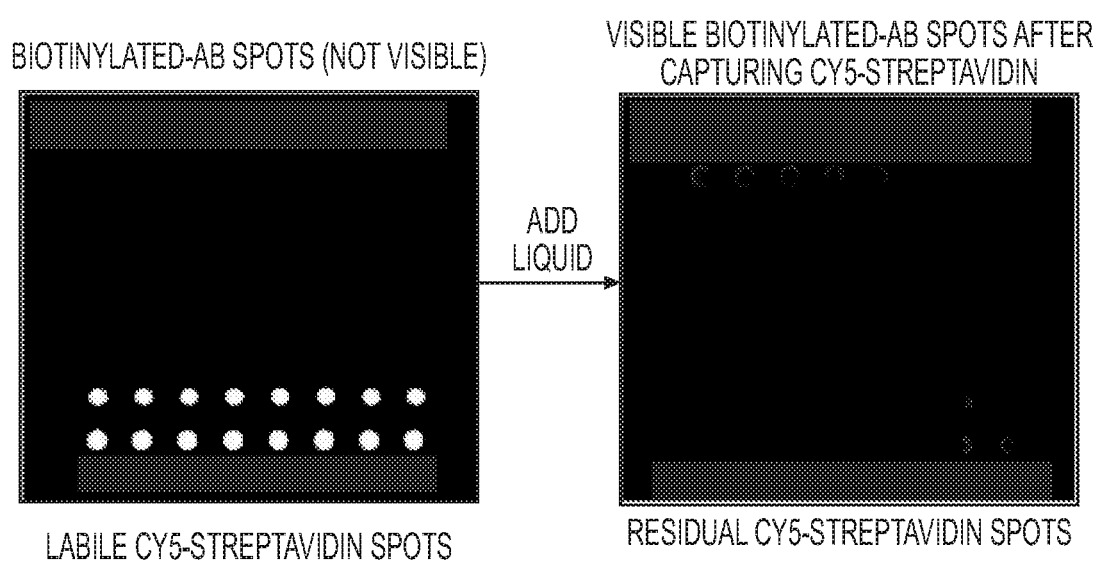
FIG. 5 illustrates proof-of-principle of feasibility of printing stable capture agent spots and labile detection agents spots on same surface. Labile Cy5-streptavidin spots dissolved into solution and bound to stable spots of biotinylated Ab after addition of a drop of buffer to chip.

Example 4. Soluble Microspots of Detection Reagents can be Printed that Dissolve in Contact with Water and Provide the Secondary Reagents Necessary for "On-Chip" Sandwich Detection Labile microspots of fluorescently labeled detection antibodies could be printed on the same surface if mixed with sufficient soluble excipient. Upon contact with a droplet of blood, these secondary reagent spots will dissolve into solution and label target present in the blood sample. Concurrently, the labeled targets contained within the sample will bind to the immobilized, non-labile capture spots. As an initial proof-of-principle experiment to illustrate the feasibility of this approach, five spots of a biotinylated-Ab were printed onto a POEGMA surface to form the "stable" immobile spots of the capture agent (FIG. 5); the stable spots cannot be seen in the top part of the left panel of FIG. 5 because they are not fluorescent. In addition, a solution of streptavidin-Cy5 and soluble PEG was spotted on top of pre-printed spots of soluble PEG to create an 8×2 array of "labile" spots of detection reagents (bottom row, left panel, FIG. 5). After one week of storage, 50 μL of PBS—a volume similar to that obtained from a finger stick of blood—was pipetted on to the surface. As seen in FIG. 5 (right panel), Cy5-streptavidin from the labile spots dissolved into solution and was captured by the five biotinylated-Ab spots to create a detectable signal (top row of right panel, FIG. 5).

The development of "labile" microspots can be a critical development in the design of the D4 POCT as it allows this assay to contain on-chip secondary reagents, which eliminates fluidic sample handling steps. This feature thus greatly simplifies the sandwich assay process by eliminating the numerous wash and liquid transfer steps that were required in its precursor, the Femtoarray™.

Example 5. Proof-of-Concept of D4 POCT in Blood

Figure 6A:
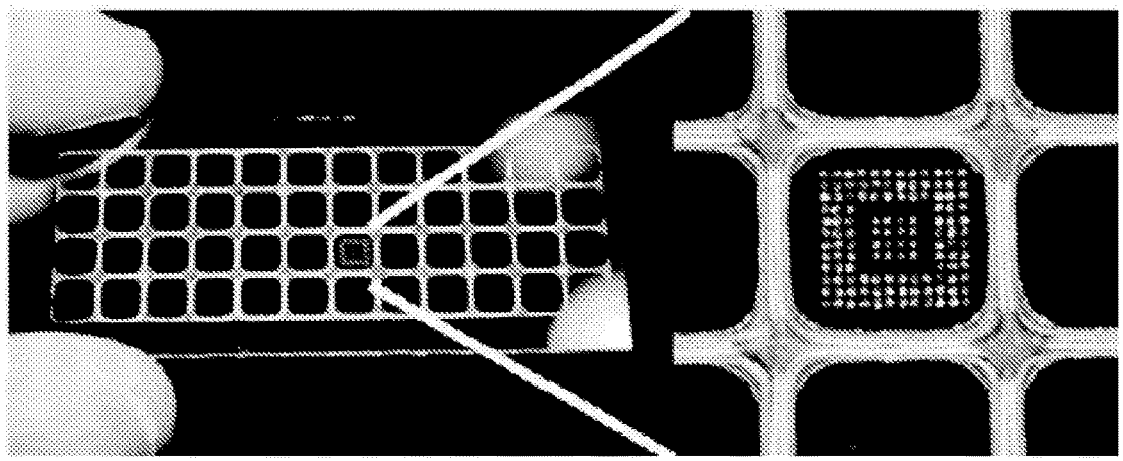
FIG. 6 illustrates glass slide with POEGMA brush that is stamped with grid of wax. (A) Antibody microarray is spotted in the center of a single wax corral. (B) Magnification of inner 4×4 capture antibody array surrounded by microspots containing soluble fluorescent detection reagents. Images in (A) were acquired by a digital camera, while (B) was acquired by a fluorescence microarray slide scanner.
Figure 6B:
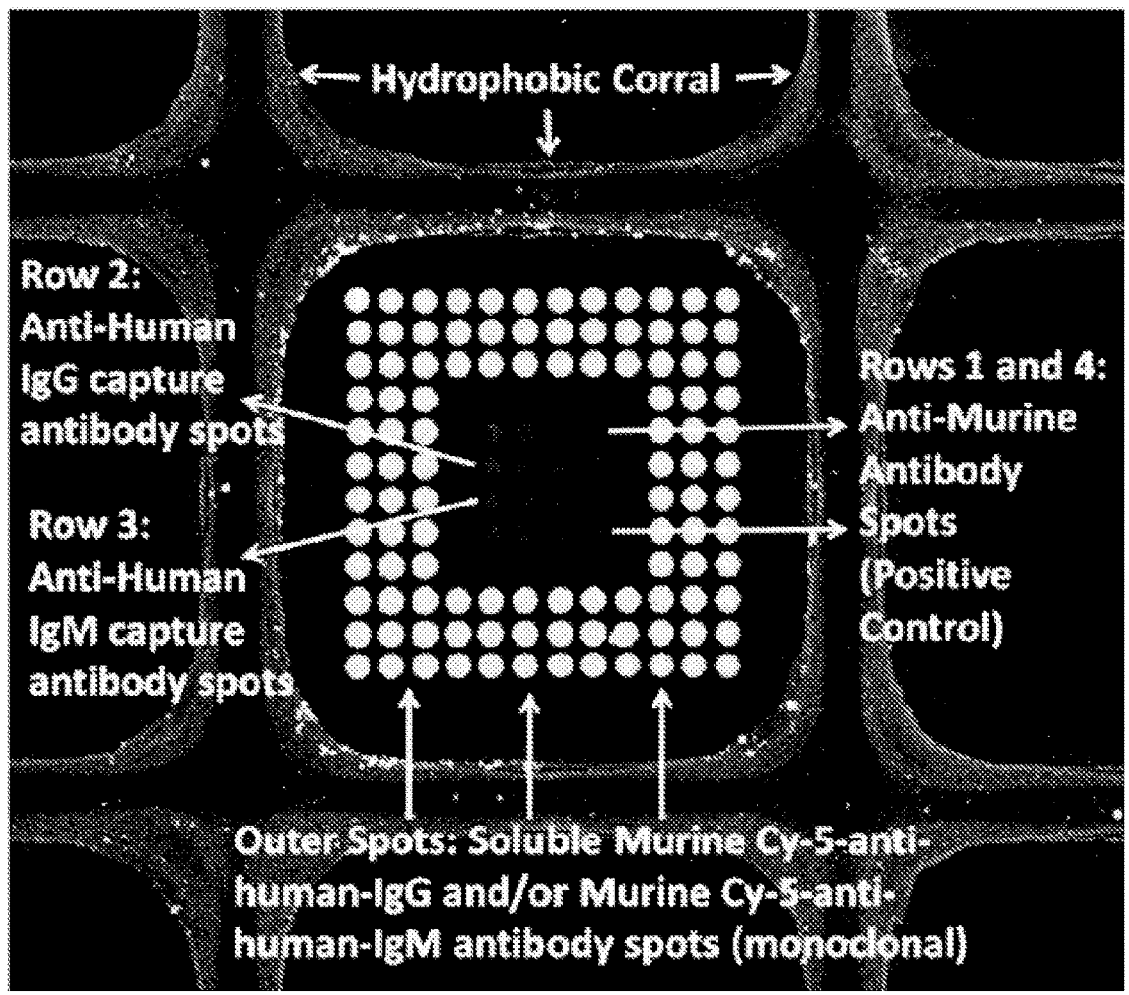

Proof-of-concept of the D4 POCT in blood was shown in detection of human IgG and IgM; these analytes were chosen because healthy donor blood can be used for this purpose. FIG. 6 shows the fabrication of a prototype assay. First, a ~30 nm thick POEGMA brush was grown on a glass slide by SI-ATRP. Then the glass slide was stamped with a grid pattern of wax using a slide imprinter to confine the sample to the active area of the chip (FIG. 6A). The slide imprinter was used to make hydrophobic corrals because it was available to us and is convenient, though it creates an entire grid of corrals. An antibody array was next inkjet printed in the center of a single wax corral; each spot is ~150 μm in diameter. The inner 4×4 array contains spots of capture antibodies (Abc) that comprise the "stable" capture spots—rows 1 and 4 are an anti-murine Abc (positive control); row 2: anti-human IgG Abc; row 3: anti-human IgM Abc. Next, the detection cocktail was printed as 3 outer rings of "labile" spots (FIG. 6B). These spots contain a mixture of murine Cy-5-anti-human-IgG and/or murine Cy-5-anti-human-IgM (detection antibodies with a different epitope against human IgG and IgM than the Abc), heparin, and a 10×-molar excess of PEG5000. The images in FIG. 6A were acquired with a digital camera while FIG. 6B was acquired with a fluorescence microarray slide scanner. Hence, the inner 4×4 antibody array has no intrinsic fluorescence and is only barely visible in FIG. 6B due to the light scattering of salt precipitates formed after the printed Abc solutions dried on the surface. The outer spots are visible because they contain Cy5-labeled Abd at a high enough concentration that they saturate the detector and hence appear white.

Figure 7A:
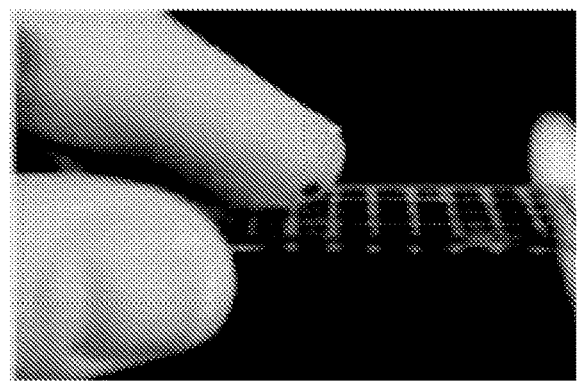
FIG. 7 illustrates an exemplary assay. (A) Dispense blood, (B) incubate for 5 min; and (C) wash with 1 mL from Visine™ bottle.
Figure 7B:
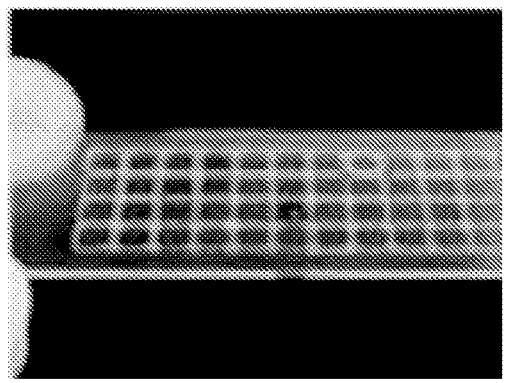
Figure 7C:
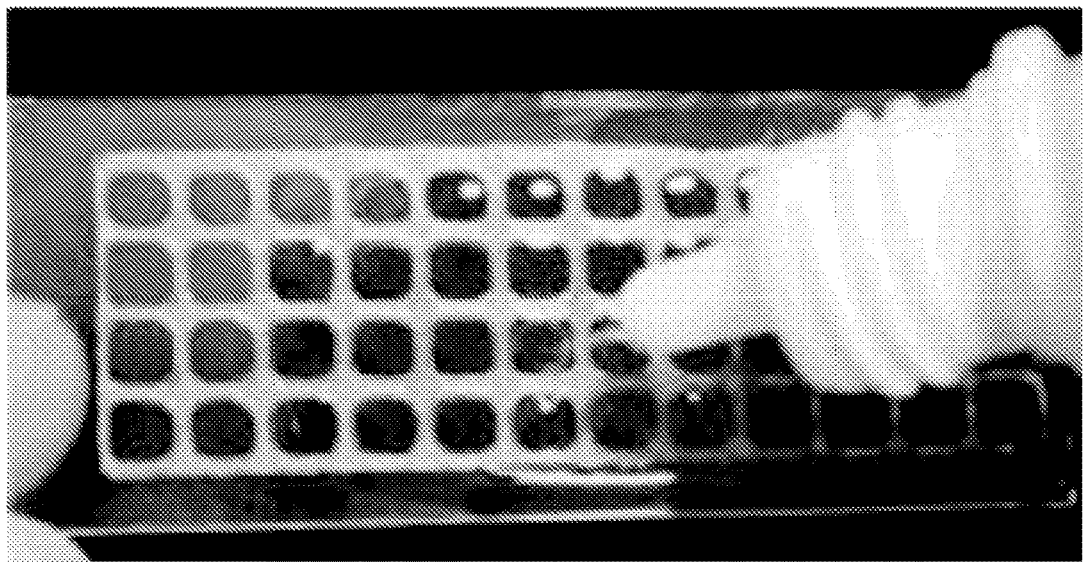
Figure 8C:
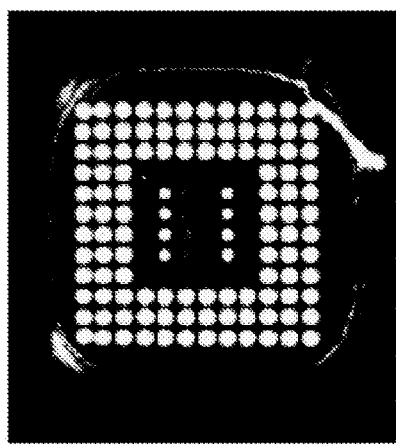
FIG. 8 illustrates results of an exemplary D4 POCT for human IgG and IgM in whole blood. (A) Printed assay prior to liquid exposure. (B)-(D) After 10 µL of human blood for 5 min followed by rinse. (B) Cy5-anti-IgG and Cy5-anti-IgM spotted in the outer rows of 'labile' detection spots. (C) Only Cy5-anti-IgG in labile detection spots. (D) Only Cy5-anti-IgM in labile detection spots. (E) After 10 uL whole chicken blood. (F) After 10 uL PBS.
Figure 8F:
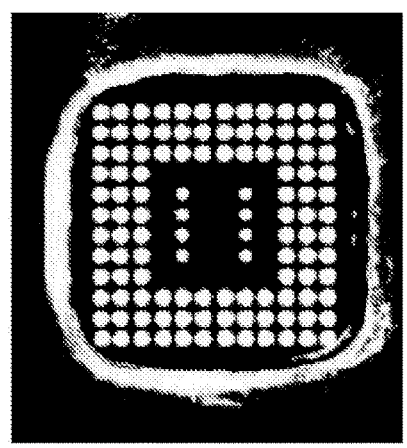
Figure 8B:
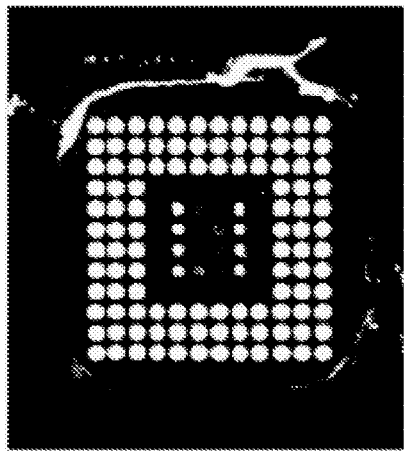
Figure 8E:
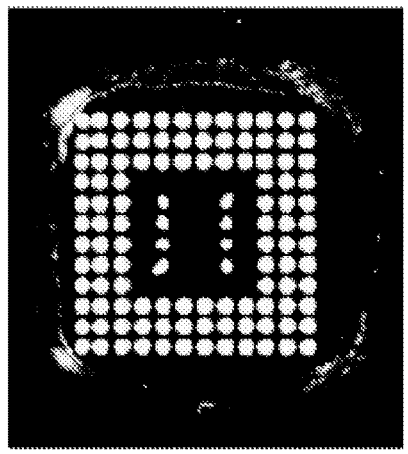
Figure 8A:
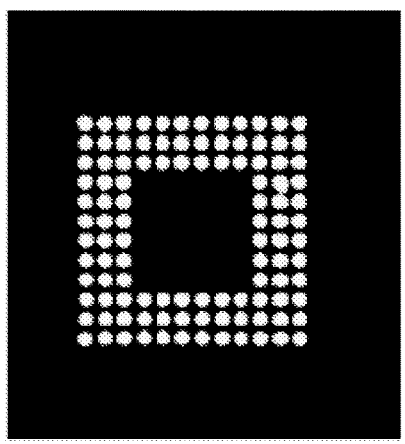
Figure 8D:
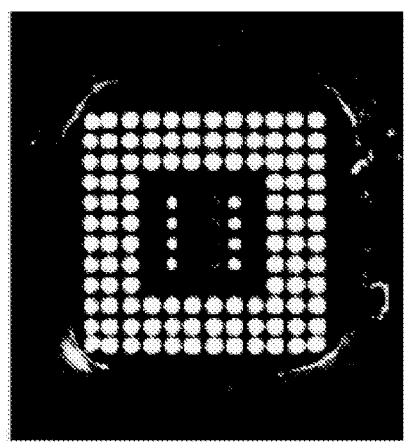

FIG. 7 shows photographs of the initial prototype of the D4 assay. A drop of blood from a finger stick (~5-10 µL) (FIG. 7A) is applied directly to the microarray and contained by the hydrophobic corral (FIG. 7B). After 5 min, the surface is rinsed with ~1 ml from a squeeze bottle, which displaces the loosely bound blood cells and proteins. Interestingly, the blood flows to the margins and binds to the hydrophobic corrals, as seen from the red color around the margins (FIG. 7C), but is completely removed from the non-fouling POEGMA surface.

FIG. 8 shows the output of the D4 POCT. In FIG. 8B, Abd for human IgG and IgM were co-printed as the labile detection spots (with PEG+heparin), so that a complete sandwich is created upon incubation in blood, leading to fluorescent spots appearing in both rows 2 and 3. The red margins in FIG. 8B-F are simply due to scattering from the blood (and excess Abd) bound to the hydrophobic corral after displacement from the POEGMA brush by the rinse step. In whole blood, the concentration of IgG is roughly 5 mg/mL (33 µM) and that of IgM is 1.5 mg/mL (1.6 µM), suggesting easy detection of protein analytes from undiluted blood at this level even in this initial experiment. FIGS. 8E and 8F show negative control experiments in which the chip was incubated with either chicken blood (E) or PBS (F) so that only the positive control rows 1 and 4 generate signal, while rows 2 and 3 show no fluorescence. FIGS. 8C and 8D are two other controls; in FIG. 8C, only the Cy5-anti-IgG Abd was printed in the labile spots, so that row 2 lights up but row 3 does not, while in panel 4D, only the Cy5-anti-IgM Abd was printed in the labile spots, so that row 3 lights up, while row 2 does not. Note that the Cy5-Abd were printed at high concentrations in the outer circumference of labile spots, and are only partially dissolved upon contact with blood, so that their residual fluorescence still saturates the detector.

Figure 9:
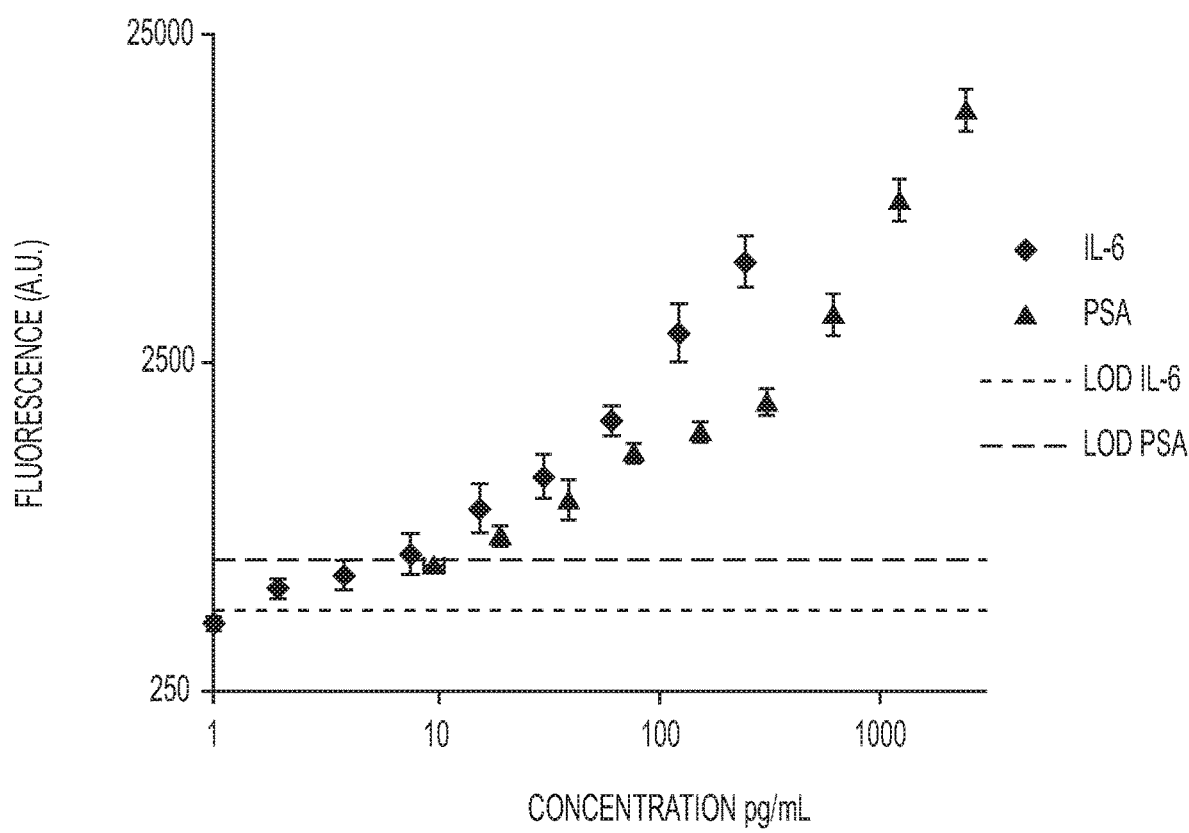
FIG. 9 illustrates results of multiplexed D4 POCT for human PSA and IL-6 spiked into chicken whole blood. LOD is blank+3SD.

Because IgG and IgM have micromolar concentration in blood, tested next was the sensitivity of the assay by a multiplexed assay for human PSA and IL-6. Dose response curves in FIG. 9 were produced by analyzing whole chicken blood spiked with human IL-6 and/or PSA—ten microliters of blood at each concentration was added to the chip and incubated for 20 minutes, followed by a 1 mL rinse. The limits of detection (blank+3SD) for this multiplexed D4 POCT are 15 pg/mL for PSA and 2 pg/mL for IL-6. In contrast, an optimized ELISA with these same antibody pairs that requires 100 µL of serum and 5 hours to complete yields detection limits of 30 pg/mL for PSA and 0.7 pg/mL for IL-6. Additional incubation time past 20 minutes improves the LOD of the IL-6 assay, which is capable of detecting 0.3 pg/mL with a 4 h incubation.

These preliminary results show the power of the D4 POCT to provide multiplexed, ELISA-like or better sensitivity from just 10 µL of whole blood in 20 minutes.

Example 6. Antibody Arrays on POEGMA are Highly Robust

Figure 10:
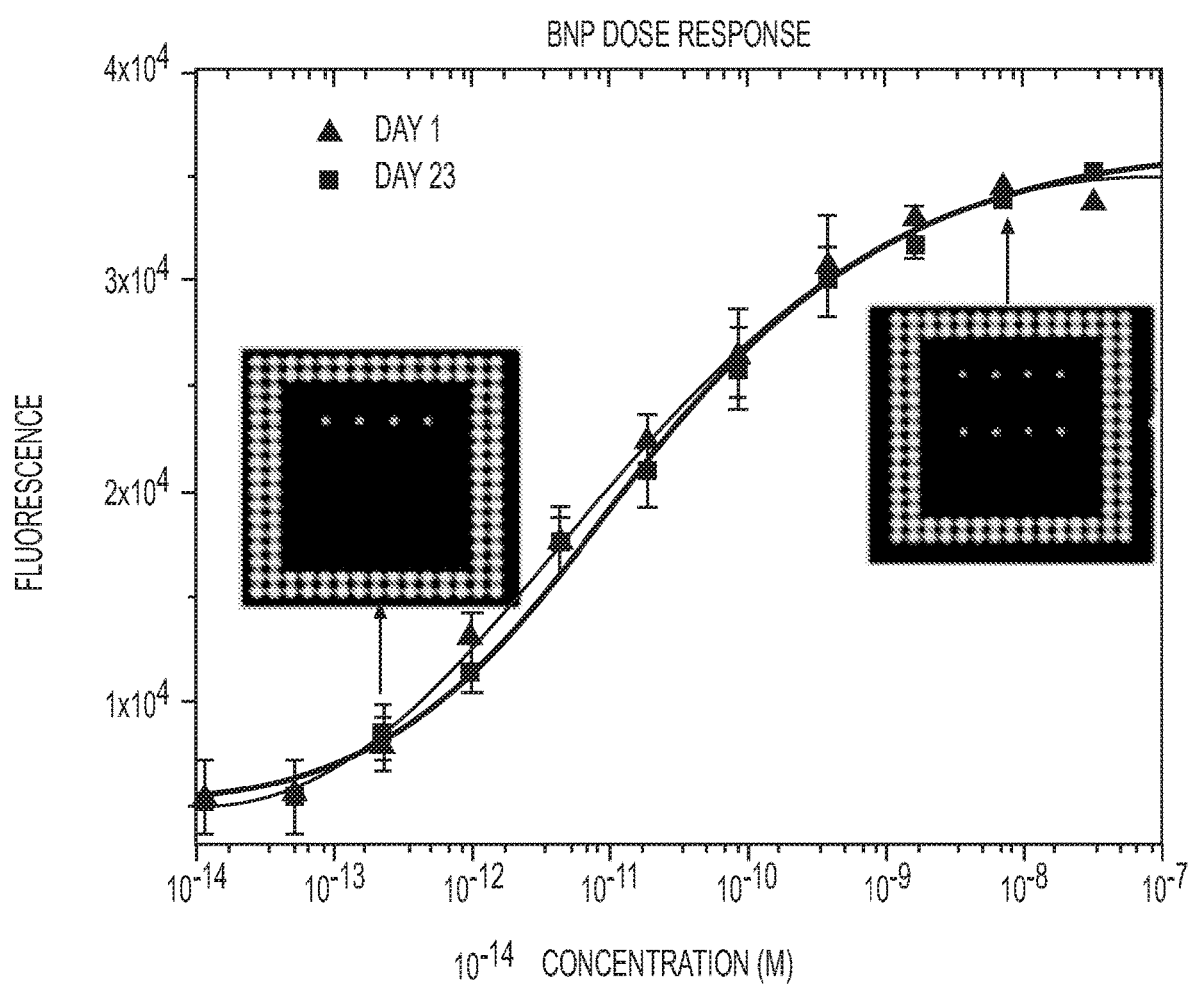
FIG. 10 illustrates dose-response curve for a BNP D4 POCT after 1 day (triangles) and 23 days (squares) of RT storage after printing. Top row: + control, bottom row: BNP.

To investigate the storage stability of microarrays printed on POEGMA, measured was the dose-response of a D4 POCT for detection of brain naturietic peptide (BNP), after 1 day and after 23 days of storage at room temperature (FIG. 10). Dose response curves yielded a LOD of 8 pg/ml. Importantly, there was no difference in the LOD or dynamic range of the assay after ambient storage for 3 weeks. These results are also consistent with previous observations of other investigators that PEG can stabilize proteins under ambient conditions. The long shelf-life under ambient conditions is an important attribute for point-of-care devices—these printed diagnostic devices will not need to be stored in buffer at 4° C., allowing for transport, storage and use at room temperature.

Example 7. Optimization of the D4 POCT

Figure 11B:
FIG. 11 illustrates Example of a second generation D4 chip (A). The antibody microarray is printed on the bottom coverslip of the in the center of the channel. Illustration of how blood is loaded into the central channel and is retained within the channel by capillary action (B-D).
Figure 11D:
Figure 11A:
Figure 11C:
Figure 12A:
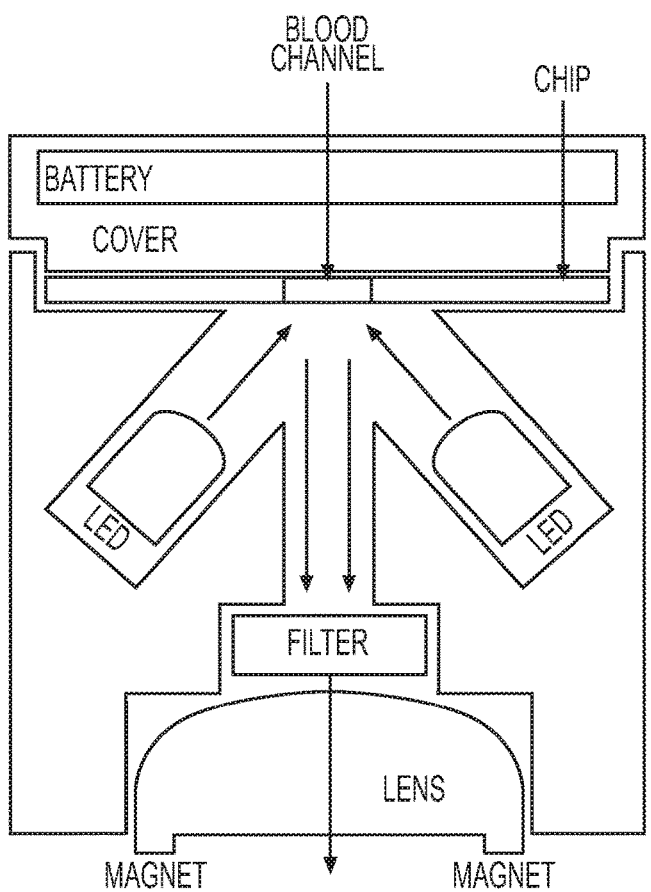
FIG. 12 illustrates (A) Cutout schematic of the design of the D4 optical detector. The magnetic ring that attaches to the smart phone is on the bottom in (A). Cutout shows the backside optical excitation and readout of fluorescence emission. (B) magnetic coupling and optical alignment of the detector to smart phone. (C) Digital picture of a fluorescent test antibody array. (D) Visual examination of the signal.
Figure 12B:
Figure 12C:
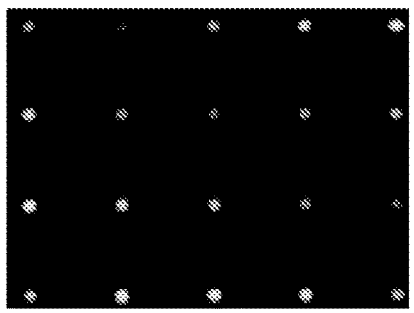
Figure 12D:

The second generation D4 chip consists of a coverslip wherein the central region is printed with the capture spots, surrounded by labile spots of the detection reagents, similar to the first generation chip. Adhesive is applied and a second coverslip is used to cover the printed spots of capture and detection antibodies such that the spots are now contained within a central channel exposed on both ends, with the analytical core of the D4 assay contained in the center of the channel (FIG. 11A). The channel width can be controlled by the area of the chip that is covered with adhesive and the amount of adhesive that is applied controls the height of the channel. This allows us to create channels with volumes ranging from 5-50 µL of blood, consistent with the volumes that can be obtained from a finger stick. The channel dimensions were carefully selected to also provide enough capillary force so that when a drop of blood is held up to one of the two ends of the channel, it is wicked into the channel by capillary action (FIG. 11B-C). Furthermore, the interfacial tension of the blood also keeps it contained within the chip (FIG. 11D). This self-loading and self-sealing design completely contains the blood within the chip.

Example 8. Design of a Cell Phone Compatible Optical Detector with Visual Backup The optical detector was designed with these requirements in mind:
(1) The detector should small and lightweight, so that it can be easily carried in a user's pocket, thereby unchaining the patient from the detector. This is in stark contrast to the design of current POCTs (e.g., iSTAT and Biosite) that are significantly larger, and are more suitable for caregivers than a patient.
(2) The optical detector should be low cost and easy to manufacture at high volumes using widely accessible and low cost manufacturing technology
(3) The detector should be compatible with a range of smart phones.
(4) The optics should not require any alignment or adjustment
(5) The detector should be able to quantify the fluorescence signal in the presence of blood.
(6) The detector should have visual backup to allow readout of qualitative results, if a smart phone is not available.

The design of the detector is shown in FIG. 12. The casing of the detector was fabricated on a Stratasys 3-D printer in ABS thermoplastic as two separate pieces: a lid and body. The lid contains an insert for the battery and has threads to allow it to be screwed into the body of the detector. The body has 4 cavities into which LEDs can be inserted and provide illumination at a 45° angle, and a frame into which the band-pass filter can be inserted. Assembly of the detector is simple: after fabrication of the two printed pieces, the bandpass filter is inserted into its holder, and four LEDs are inserted into their prefabricated cavities and wired to allow contact with the lid when it is screwed on to the detector. Assembly is complete after a 10× magnification lens is added, a battery is inserted into the lid, and the lid is screwed into the body of the detector. Finally a concentric magnetic ring is glued into the rim of the lens of the detector.

Use of the detector is equally simple. The lid is unscrewed revealing a slot for the blood-loaded chip to be placed, such that the coverslip with the printed antibodies is on the bottom (away from the lid). With the chip placed in this configuration, the fluorescent spots in the D4 array are illuminated from below by the LEDs. Only the emitted fluorescence passes through the band pass filter placed between the chip and the lens of the detector. The spots are magnified 10× by the lens and an image of the array is digitally captured by the smart phone camera. The detector and smart phone optics have a built-in magnetic self-alignment: a concentric magnetic ring is glued both on the lens of the detector and around the lens of the smart phone, which magnetically aligns the optics of the two devices.

Example 9. Detection and Diagnosis of Cancer

The primary barriers to testing multiple analytes for cancer detection in a POC setting are: (1) cost; (2) response time; and (3) blood collection and sample handling. The design of the D4 POCT addresses these issues with a suite of enabling technologies that form the core of the D4 POCT, as follows: first, cost of testing and response time will be reduced through miniaturization, multiplexing, and by testing directly in undiluted whole blood obtained from a finger stick (e.g., ~10 µL) with no preprocessing or microfluidics. Miniaturization of the assay will reduce consumption of reagents (and hence cost), and minimize diffusion distances (and hence time), while multiplexing (testing multiple analytes simultaneously) will save on both cost and time. Directly testing from whole blood in a single integrated assay will allow one-step, on-site processing of samples. Second, in order to create a simple and self-contained POC assay, exploited was on-chip diffusion to bring spatially separated reagents together to create a functional assay and thereby eliminate the need for liquid transfer steps and microfluidic manipulation of sample or reagents. Third, the assay is fast because it is integrated and performed directly in whole blood in a miniaturized, multiplexed format and with no wash steps, with a projected read-out time of e.g., <20 minutes. Fourth, this multiplexed platform will be capable of quantifying a panel of biomarkers with a single drop of blood, with no sample preprocessing. In contrast, most current POC diagnostics are single analyte assays. Fifth, the D4 assay can be utilized for any protein microarray for which antibody pairs are available, and is hence, broadly applicable to all heterogeneous immunoassays.

Example 10. Design of Next Generation of D4 Chips

Exemplary modifications to the current D4 chip, which may enhance its analytical robustness and performance, are described in the following paragraphs.

A D4 chip having self-calibrating properties will be designed and validated. Accordingly, a dilution series of analyte will be printed on the chip as a row of positive control capture spots. The spot intensity of the positive control will provide a dose-response curve that will serve as an internal calibration for each chip. Signal generation at these control spots will signify a viable assay by verifying activity and diffusion of the detection reagents. In addition, by varying the concentration of target within these control spots, there will be a signal gradient across the spots that can be used to normalize fluorescence intensities and reduce inter-assay variability. This control gradient can also be compared to signal generated at the capture antibody spots, which will aid in quantification of target levels and reduce sampling variables such as volume of blood added to the chip, blood viscosity, incubation temperature and time to measurement. In essence, the spot intensity gradient of the positive control spots will provide a reference signal, similar to a dose-response curve, that will serve as an internal calibration for each chip.

Figure 13:
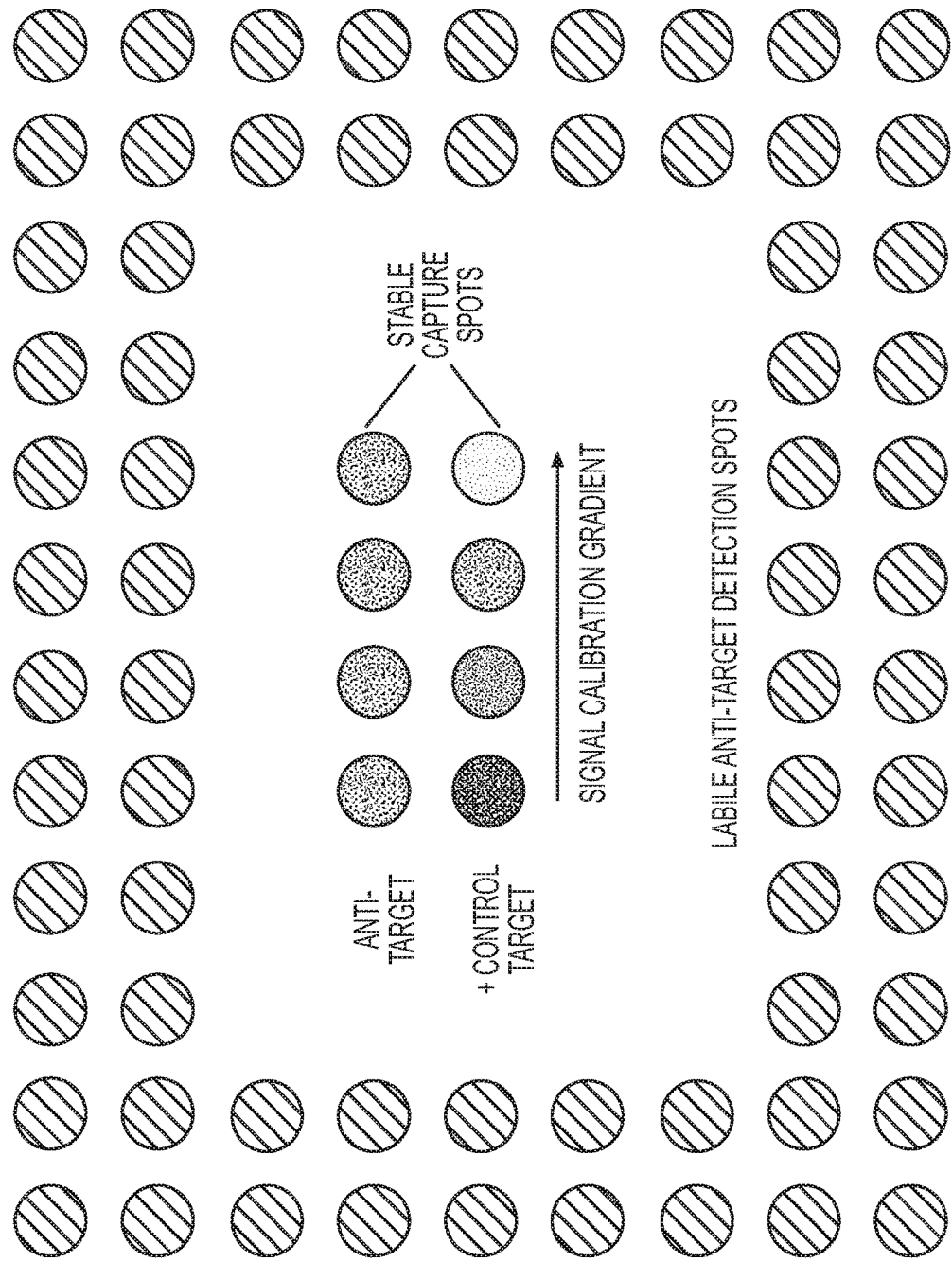
FIG. 13 illustrates an exemplary format of D4 microarray for Human alpha-Fetoprotein (AFP). The signal gradient produced by varying AFP concentration within the +control spots serves as an internal calibration standard.

A microarray for the detection of a target will be printed within the central channel of the chips as shown in FIG. 13. AFP will be used as a sample target. This microarray will contain "stable" microspots of anti-AFP capture antibodies and "labile" microspots of labeled anti-AFP detection antibodies. In addition, "stable" microspots of AFP will serve as a positive control and calibration standard.

To ensure that the labile spots of printed detection antibody (Abd) are dissolved upon contact with blood, soluble PEG will be added to the print solutions. The soluble PEG will preferentially adsorb into the POEGMA brush and block the adsorption and immobilization of the Abd. Although confined in spots simply due to inkjet printing and the macroscopic drying process, these Abd will remain in a "labile" state and can be easily dissolved and released upon contact with an aqueous solution, as shown in the preliminary studies. The addition of excess soluble PEG to the Abd is critical, as it stabilizes the detection reagents during storage, and importantly serves as an excipient that helps resolubilize the Abd when the test blood droplet is introduced. Upon contact with a droplet of blood, these labeled antibodies will dissolve into solution and bind to, and thereby label, all target present in the blood sample.

As a positive control, spots of AFP will be printed alongside the capture antibody spots. These will serve to verify activity and diffusion of the detection reagents, and signal generation at these control spots will signify a viable assay. In addition, by varying the concentration of AFP within these control spots, there will be a signal gradient across the spots that can be used to normalize fluorescence intensities and reduce inter-assay variability. This control gradient can also be compared to signal generated at the experimental anti-AFP capture spots, which will aid in quantification of experimental AFP levels and should help reduce sampling variables such as volume of blood added to the chip, blood viscosity, incubation temperature and time to measurement.

In order to prevent blood clotting, labile heparin spots will also be printed. This study will investigate the effect of heparin, PEG, and Abd concentration, as well as PEG molecular weight, on the dissolution of the labile spots, the retention of Abd activity, and the anti-clotting capabilities of the spotted heparin. Arrays with varying concentrations of the detection spot components will be spotted as shown in FIG. 13 and stored under ambient lab conditions for 1 day, 1 week, and 1 month. After removal from storage, 10 µL of blood will be added to each chip and incubated until clotting occurs. Residual fluorescence of the detection spots will be used to quantify the effects of additives on the solubility of these spots, while the fluorescence of the positive control spots of AFP will be used to determine retention of Abd activity. The concentration of AFP within the positive control spots will be systematically varied in order to determine the optimal concentration gradient necessary to fully span the dynamic range of the detector and bracket the physiological range of AFP concentration in the blood. The amount of time required for blood to clot within the central channel will be used to determine the effect of heparin and the time-course study will provide a measure of the shelf-life of these chips.

An example of a finalized formulation for printing soluble spots, including concentration and molecular weight of PEG additives, would be printing in a 1% solution of PEG with a 10,000 MW. Determination of amount of printed heparin needed to prevent clotting of blood sample in channel, an example is 1 ng of heparin printed on each chip is required to prevent blood clotting. Necessary concentration of AFP in positive control spots to produce a signal gradient useful for assay calibration, an example would be spots printed from the following concentrations of AFP: 1 ug/mL, 10 ng/mL, 100 pg/mL and 1 pg/mL.

Example 11. Development of D4 Assay Capable of Detecting AFP Directly in Whole blood. Further exemplary modifications will lead to the development of a quantitative POC assay for AFP that will incorporate the concept of detection reagents printed as "labile spots." The figures-of-merit (FOM) of this assay will be used to benchmark the changes to the assay format described further examples below.

Quantitative D4 Assay: Detection agent printing conditions, as determined by the experiments described in example 11, will be used to print arrays to detect AFP (as shown in FIG. 13). Dose-response curves covering concentrations from 0 g/mL to 1 pg/mL will be generated using AFP-spiked buffer, followed by dose-response curves using AFP-negative chicken blood (chosen because it will not contain any human AFP, but will still accurately reflect the complexity of using whole blood) spiked with the analyte. The dose-response data from 20 separate dose-response dilutions will be fit with a five-parameter logistic (5-PL) curve. Parameter estimation will be performed by a large-scale trust-region reflexive Newton algorithm using MATLAB. The assay will be evaluated in terms of its limit-of-blank (LOB), limit-of-detection (LOD), linear calibration range (LCR), upper and lower limits of quantification (LOQ) and coefficient-of-variance (COV). Twenty zero standard replicates will be used to determine the LOB, which will equal meanblank+1.645(SDblank). LOD will be based on both the measured LOB and 20 test replicates of a low analyte concentration known to produce a signal close to the LOB, and will be calculated as LOB+1.645(SDlow concentration sample). The LCR will be determined from the 5-PL fit, and defined as the region of the calibration curve within which the slope remains linear and the correlation coefficient of the line is no less than 0.995. The upper and lower bounds of this linear region will define the upper and lower LOQ. COV will be determined by testing three samples of known concentration (representing low, middle, and high values within the LCR) in twenty separate assays, with a COV determined for each concentration.

Benchmarking against a commercially available test: A commercially available ELISA kit for AFP will be used to benchmark the utility of the finalized assay. Samples will be analyzed in parallel in order to directly compare the figures of merit between the commercial ELISA and D4 POCT results. This will lead to the development of a quantitative D4 assay for detection of AFP from whole blood with a validated dose-response curve that provides the LOD, LOQ, DR, COV, and inter- and intra-assay precision. The FOM of the D4 POCT will be similar to or better than the commercially available ELISA kit.

An exemplary quantitative D4 assay for AFP would be capable of providing ELISA like or better sensitivity in 20 minutes and have a LOD of 5 pg/mL and other FOM equivalent to a clinical ELISA.

Example 12. Design of a Chip to Maximize Sensitivity

A chip with maximized sensitivity will be designed by placing the capture spots closer to the blood entry point while the labile spots are downstream to ensure that all antigen is captured by the capture spots. FOM of this design will be compared to the previous generation D4 chip evaluated in example 12.

In traditional lateral flow immunoassays (LFA), the analyte solution dissolves soluble detection reagents prior to reaching test lines of capture antibodies. This is necessary because the flow stream in an LFA is in one direction only, and therefore the detection reagents can be dissolved in the analyte solution prior to reaching the capture antibodies. This design allows detection antibodies to bind antigen prior to antigen-capture antibody binding, and therefore the potential exists for antigen-detection antibody binding to block antigen-capture antibody binding. Using a carefully matched pair of monoclonal antibodies minimizes this issue, but can significantly increase cost.

Figure 14A:
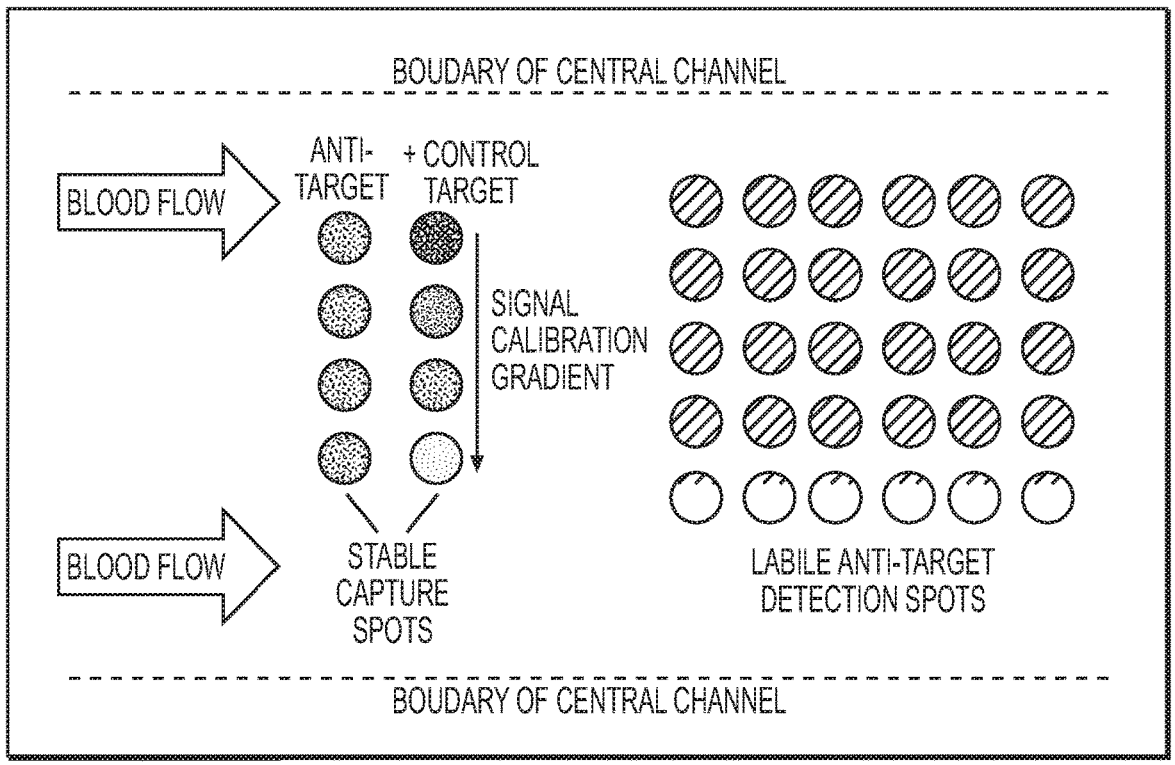
FIG. 14 illustrates a test array format. Two separate arrays are printed, one for anti-AFP capture spots and AFP calibrator and one for soluble anti-AFP detection spots. The order in which these two arrays are exposed to analyte solution are alternated—blood initially contacts capture spots first in panel A, and detection spots first in panel B.
Figure 14B:
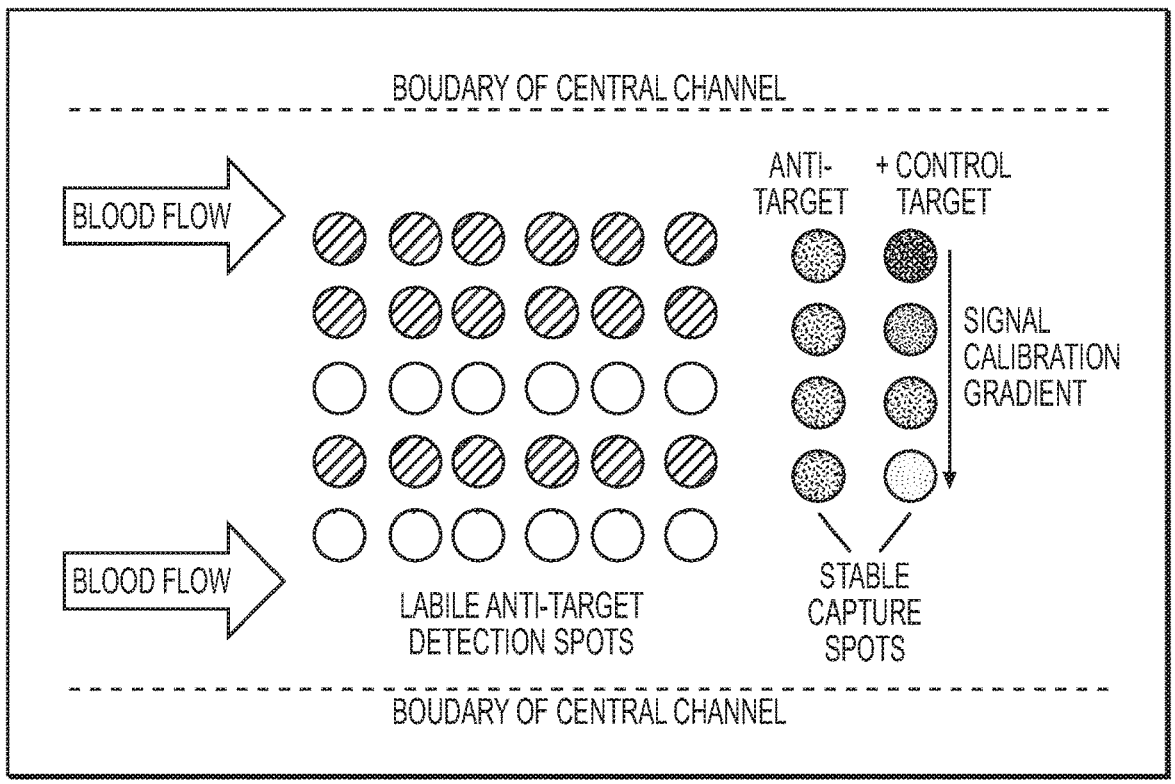

The diffusion based design of the proposed format does not require the upstream placement of detection antibodies. Without being bound by any theory, it is thought that the chip sensitivity will be increased if the analyte solution reaches capture spots prior to detection spots and should allow antigen to initially bind to capture spots without any interference from detection antibodies, as the detection antibodies will only arrive at the capture spots by diffusion that occurs after the capture spots have been exposed to the analyte solution. An example of this arrangement is shown in FIG. 14 which involves alternating the position of two separate arrays within the central channel of the chip: 1) An array composed of anti-target capture spots (yellow) and target calibration spots (blue), and 2) An array of soluble anti-target detection spots (red).

These studies will lead to the determination of how the order in which blood contacts the capture and detection spots affects assay sensitivity, for example, placing capture spots upstream from detection spots may improve the assay sensitivity from 5 pg/mL to 0.5 pg/mL

Example 13. Effect of Diffusion Distance in the D4 Assay

Figure 15:
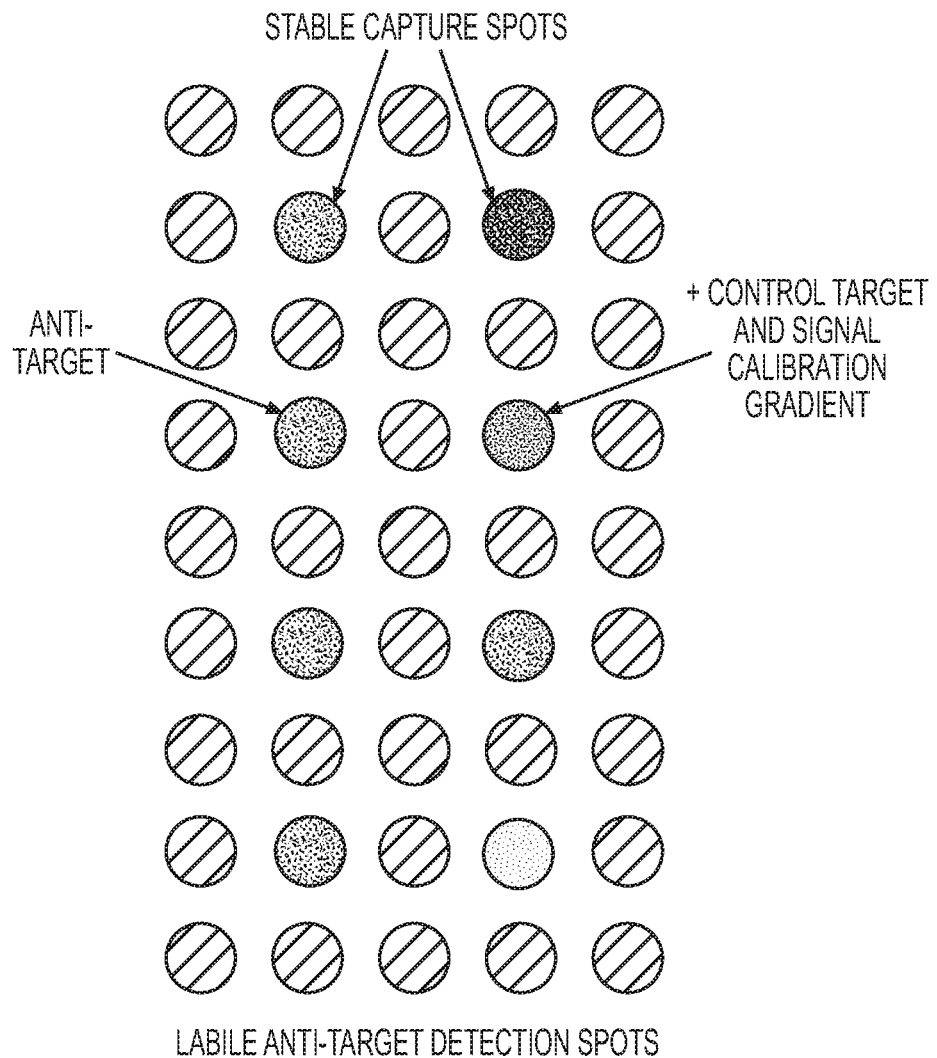
FIG. 15 illustrates that each stable capture spot can be surrounded by labile detection spots in order to reduce diffusion distance of detection antibodies.

Further testing of diffusion distance in the D4 assay will be conducted. An assay format as shown in FIG. 15 will be configured wherein each capture spot will be surrounded by multiple soluble detection reagent spots in close proximity. Without being bound by any theory, it is thought that assay reaction time will be decreased by the multiple soluble detection regent spots proximally located and this geometry will be capable of providing higher local concentrations of dissolved detection reagents around each capture spot and thereby reduce the amount of detection reagent that can be printed on-chip.

This geometry provides shorter diffusion distances and therefore potentially faster labeling of captured antigen than the standard geometry used in the preliminary studies in which the capture spots are surrounded by concentric rings of labeled detection antibody. The array in FIG. 15 will be further exposed to a dose range of antigen and the assay FOM will be determined as described in example 12 and compared to the standard D4 assay shown in the preliminary studies. Assuming FOM are equivalent to or better than the standard D4 assay, a time course video of the assay will be used to assess the degree to which the assay can be shortened while still retaining the performance metrics of the standard D4 assay.

While a shortened assay would be advantageous, it is also useful to determine how this geometry can potentially decrease assay cost by reducing the amount of detection antibody printed on the chip. In this case, local concentrations of detection antibody around each capture spot should be higher during detection spot dissolution. Without being bound by any theory, this higher local concentration due to spot proximity should allow decreased amounts of printed detection antibody to produce the same local concentration around each capture spot as is achieved with the larger amounts of detection antibody that are printed in the first generation D4 format. By systematically decreasing the amount of detection reagent printed in each detection spot, the minimum amount of detection reagent necessary to produce FOM equivalent to the standard D4 assay will be determined.

In addition to the possible advantages discussed above, this geometry should provide each capture spot with a more uniform exposure to detection antibody during detection spot dissolution, as each capture spot is located the same distance from the nearest detection spots. This geometry will be incorporated into the final design described in example 15 below, if a useful reduction in assay time, detection antibody requirements, and/or assay variability is observed.

These exemplary studies will lead to the determination of how diffusion distance affects assay time and the amount of detection antibody printed on chip. For example, the proposed geometry may reduce the time needed to achieve 5 pg/mL sensitivity from 20 minutes to 15 minutes. Another example would be that the proposed geometry makes it possible to reduce total detection antibody printed on chip from 200 picograms to 50 picograms.

Example 14. Integration of Chip Design

All features and potential printing geometry changes examined in examples 11-14 will be taken into account and combined into a single assay format, and the final, optimized chip will be tested for its FOM using analyte spiked chicken blood. Limit-of-blank (LOB), limit-of-detection (LOD), linear calibration range (LCR), upper and lower limits of quantification (LOQ) and coefficient-of-variance (COV) will be determined as described in example 12 and compared against the results from a commercially available plate based ELISA test kit for AFP.

Exemplary D4 assays for AFP detection described herein will have improved sensitivity, shortened assay time, or reduced detection antibody requirements that still maintain ELISA like or better sensitivity.

Example 15. Development of AFP-L3 Assay

Design features identified during AFP assay development in examples 10-14 will be used to produce an equivalent D4 assay for AFP-L3 isoform. Assay FOM will be determined as described in example 12, and a side-by-side comparison with a commercially available plate-based ELISA test kit will be used to benchmark the AFP-L3 assay.

Exemplary D4 assays for AFP-L3 detection described herein will be capable of providing ELISA like or better sensitivity in 20 minutes. For example, the assays will have a LOD of 5 pg/mL and other FOM equivalent to a clinical ELISA.

Example 16. Duplex D4 Assay for AFP and AFP-L3

Figure 16:
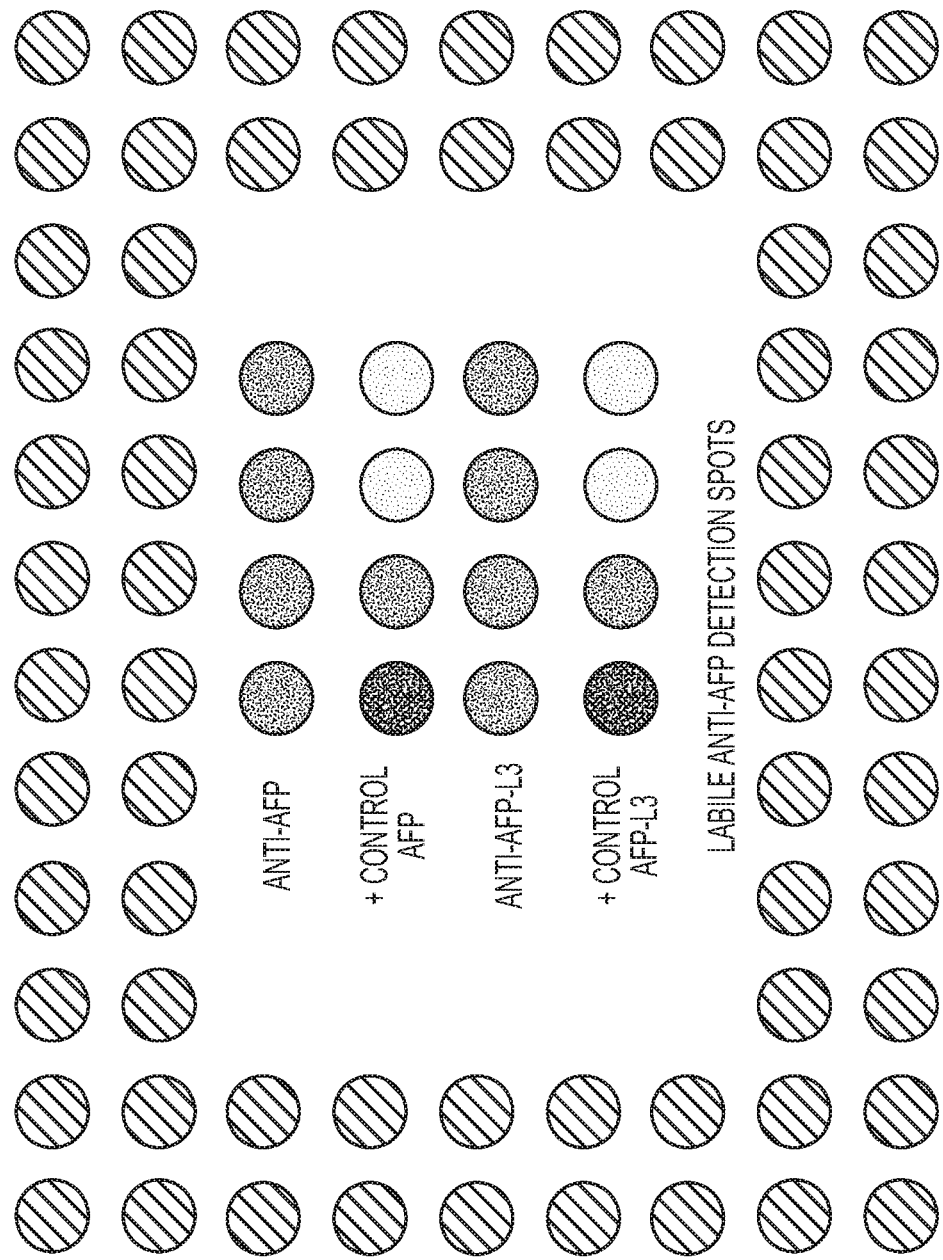
FIG. 16 illustrates an exemplary duplex D4 array for AFP and AFP-L3 with positive control calibration standards.
Figure 17:
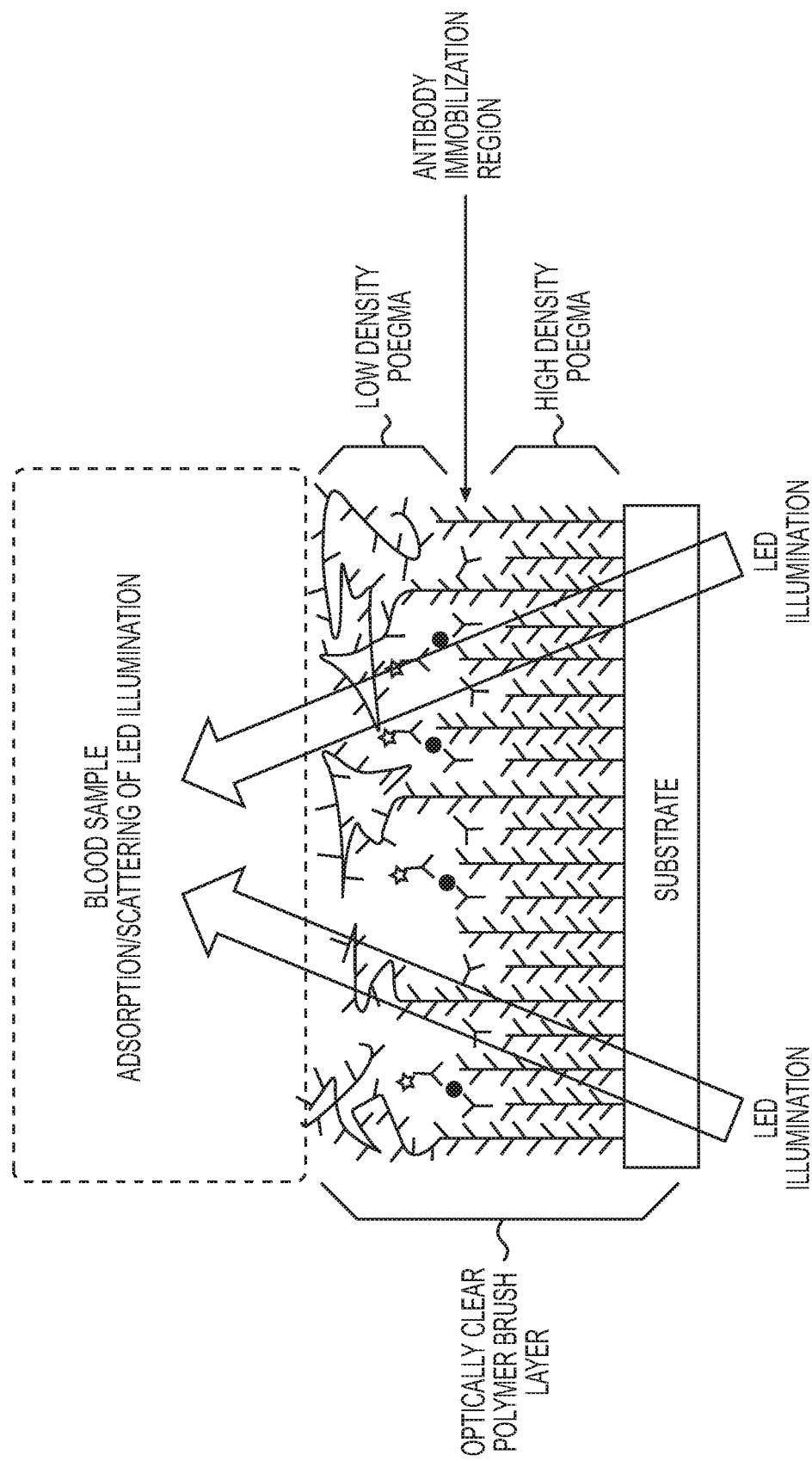
FIG. 17 illustrates an exemplary D4 POCT biointerface.
Figure 18:
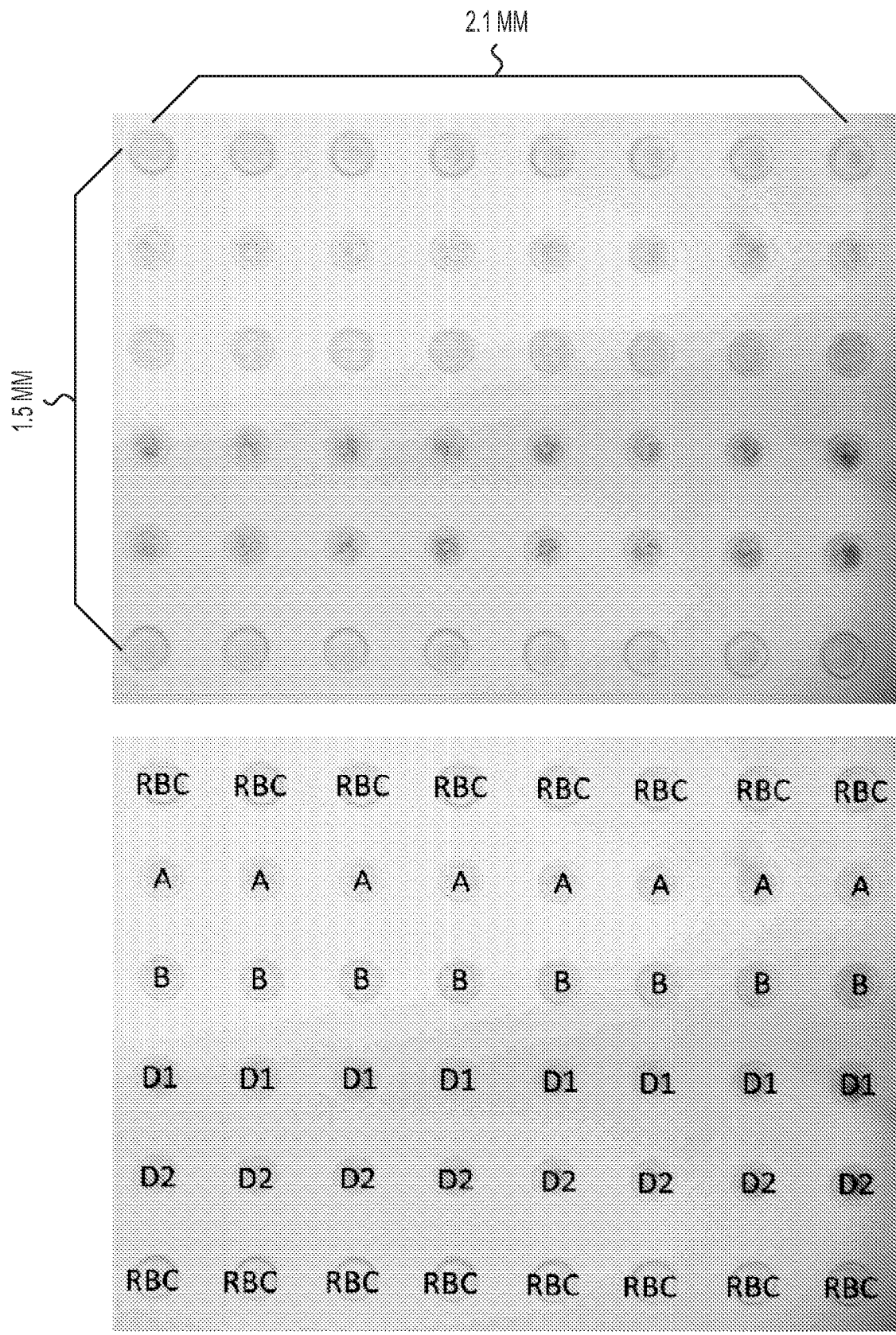
FIG. 18 illustrates a POEGMA antibody Array Format 1. All antibodies printed as received, spot diameter approximately 125 micron. Image of actual array printed within wax corral is shown on the top, with antibody location overlay shown on the bottom. Antibody Locations in Array: RBC=33F1 Anti-Human Red Blood Cell; A=GAMA120 Anti-A; B=GAMA110 Anti-B; D1=F8D8 Anti-D; D2=GAMA401 Anti-D.
Figure 19:
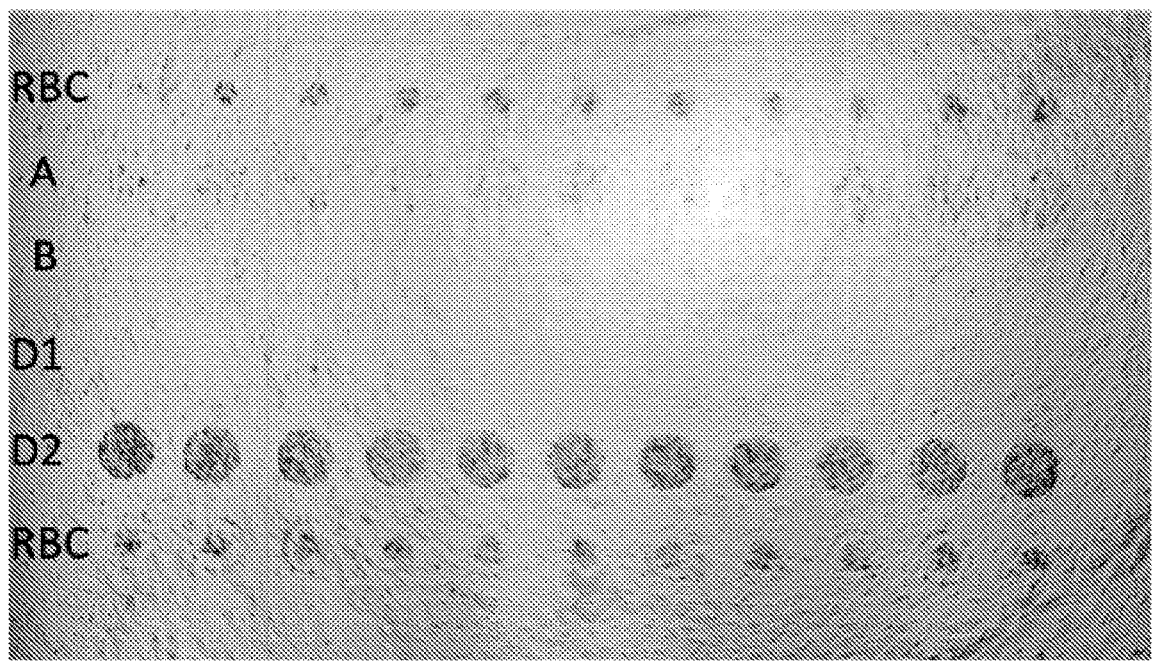
FIG. 19 illustrates some results of a POEGMA antibody array exposed to A+ Blood: images of array prior to washing (top) and after washing and aspiration (bottom). Prior to washing, spots are visible, but obscured by gravity settled cells and cells in solution.
Figure 19:
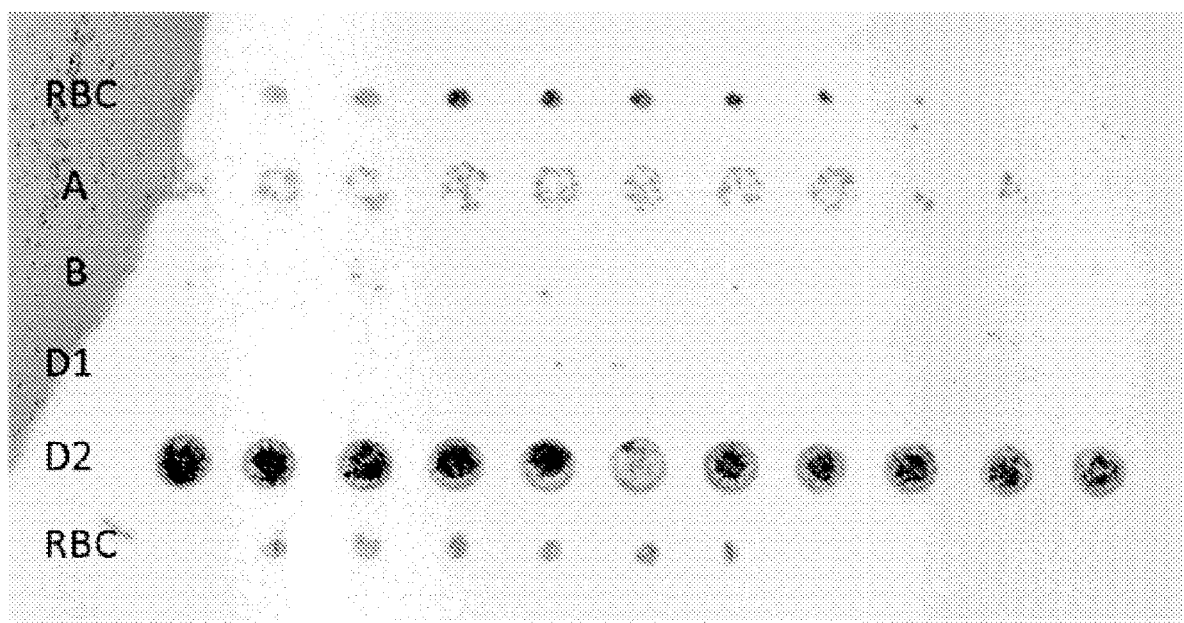
Figure 20:
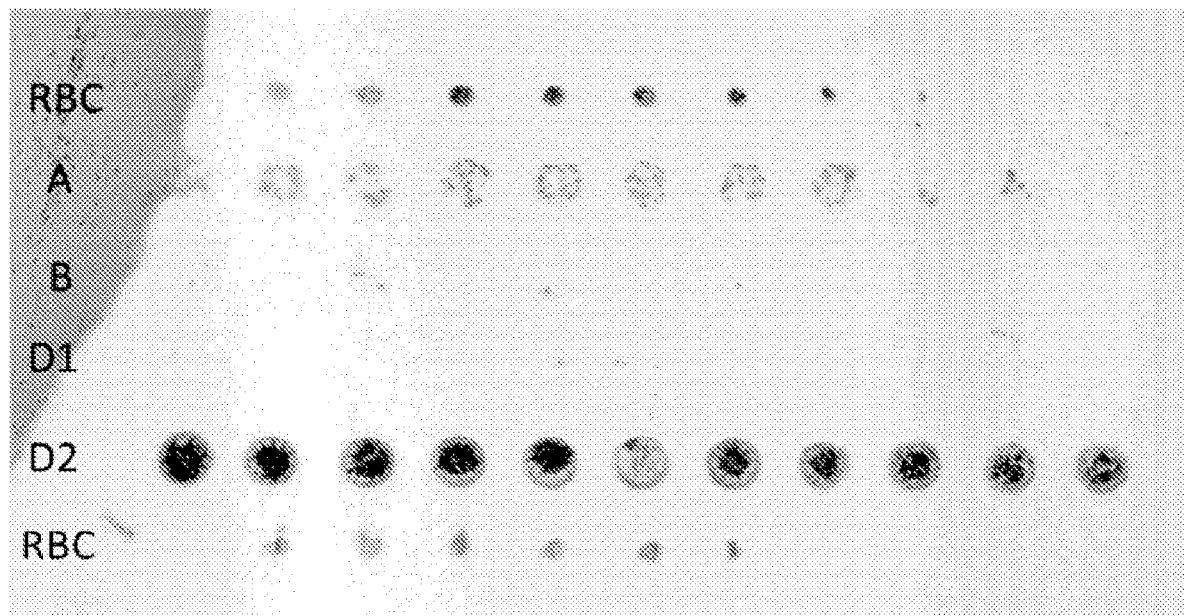
FIG. 20 illustrates results of a POEGMA antibody array exposed to A+ Blood: images of array after washing and aspiration (top) and select spot morphology (bottom). As expected for A+blood, binding occurs to anti-RBC rows 1 and 6, anti-A row 2, and anti-D2 row 5.
Figure 20:
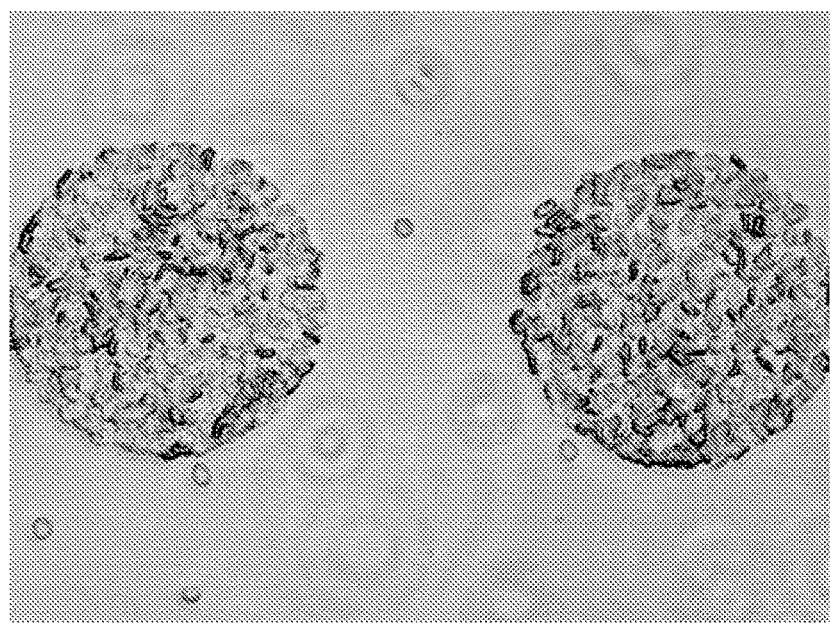
Figure 21:
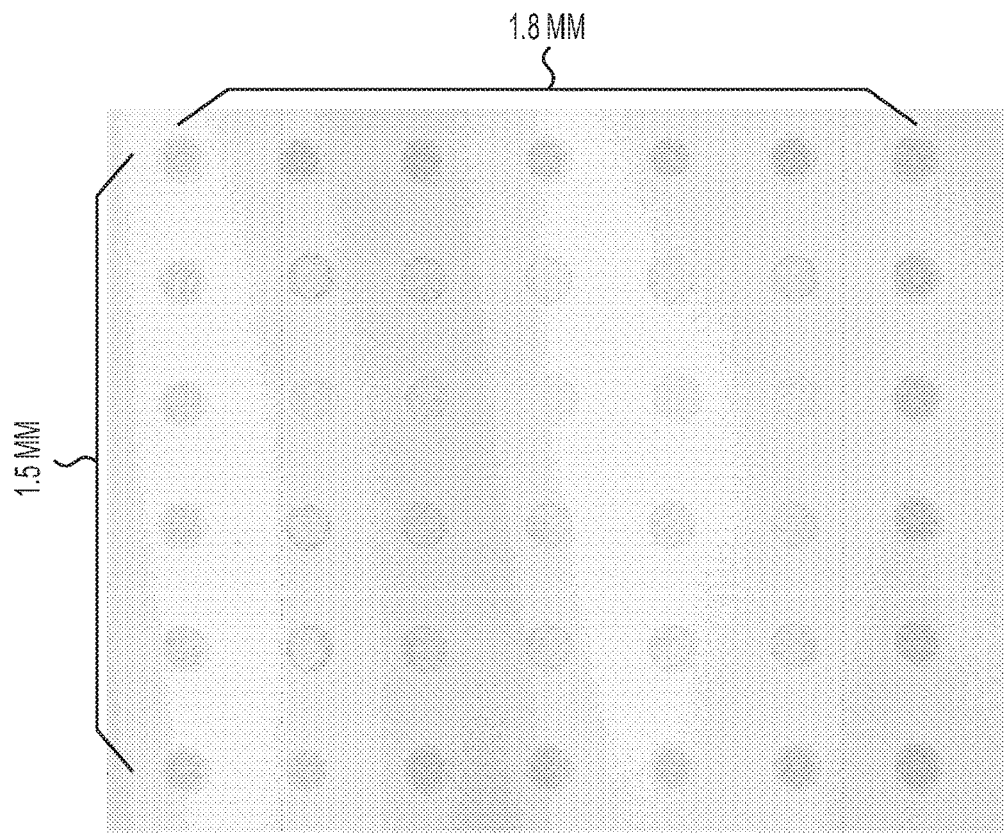
FIG. 21 illustrates a POEGMA antibody array printed with buffer additives. All antibodies diluted 1:1 with a print buffer. Spots are approximately 110 microns in diameter. Image of actual array printed within wax corral is shown on the top, with antibody location overlay on the bottom. Antibody Locations in Array: RBC=33F1 Anti-Human Red Blood Cell; A=GAMA120 Anti-A; B=GAMA110 Anti-B; D1=F8D8 Anti-D; D2=GAMA401 Anti-D.
Figure 22:
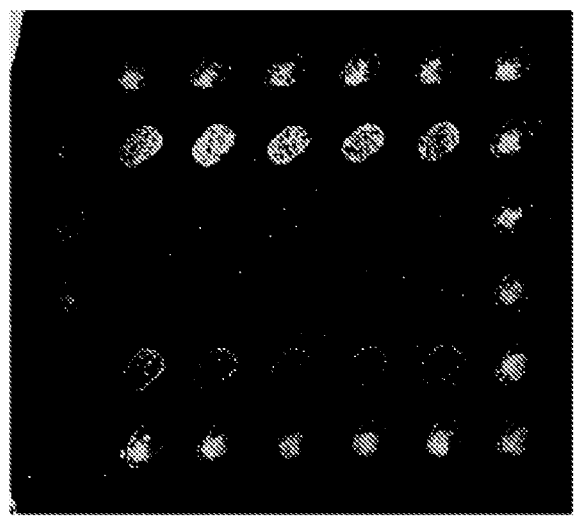
FIG. 22 illustrates results of a POEGMA antibody array for detection of blood group antigens. Exposed to A+ Blood (top); Exposed to B+ Blood (middle); Exposed to O+ Blood (bottom)'. The results show that the array is specific for A, B, O blood types.
Figure 22:
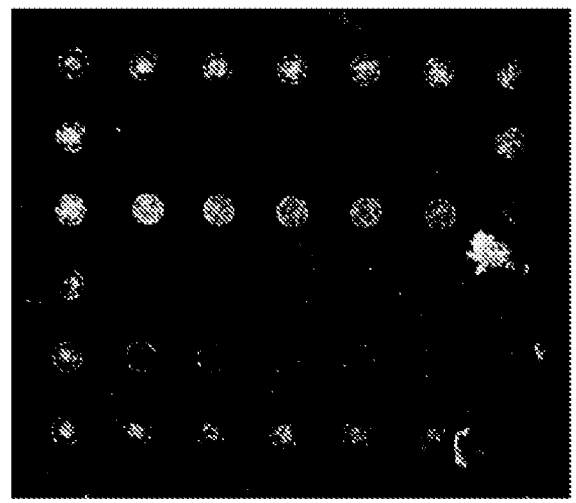
Figure 22:
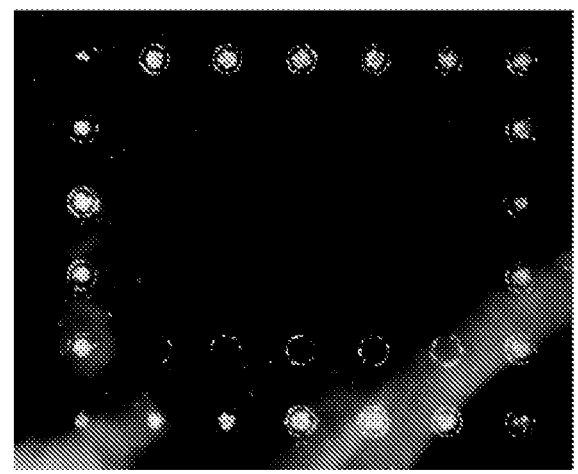
Figure 23:
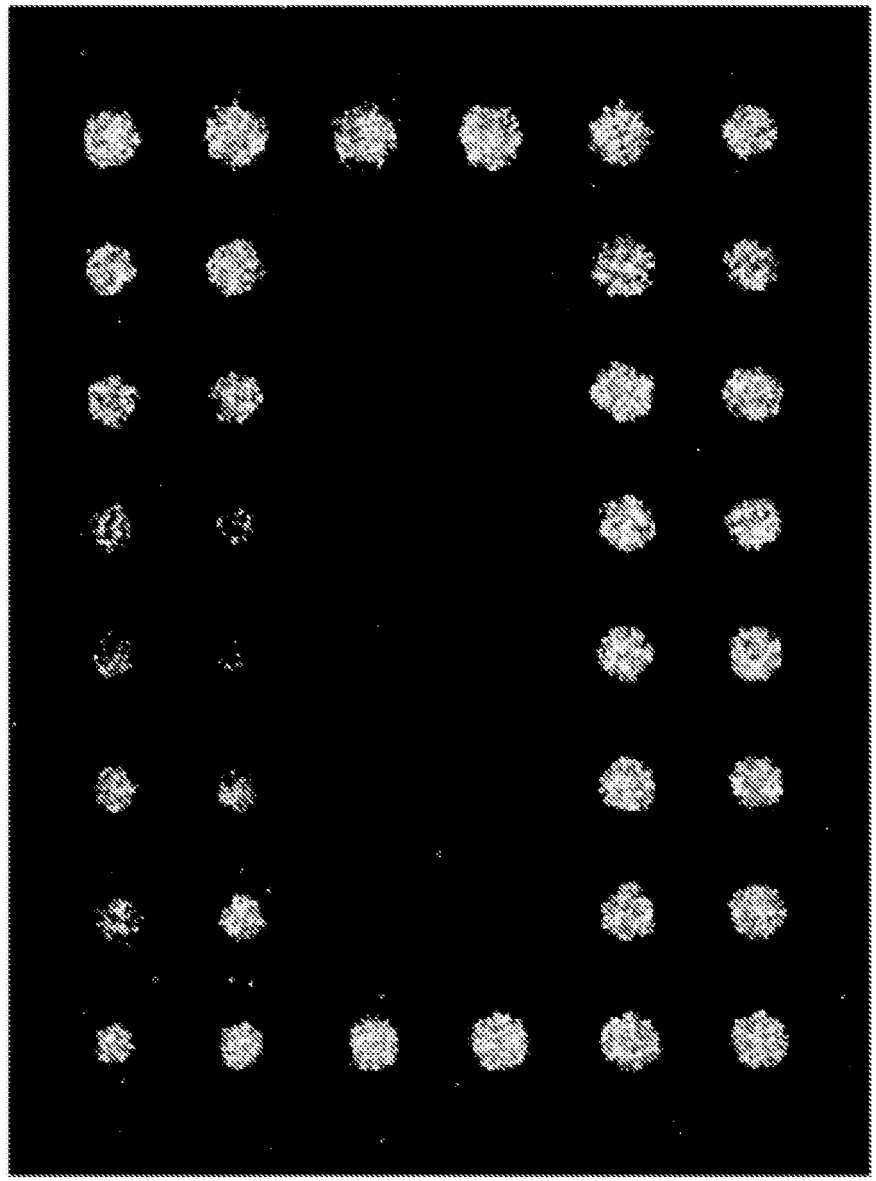
FIG. 23 illustrates results of a POEGMA antibody for detection of blood group antigens when exposed to A+ Blood.
Figure 24:
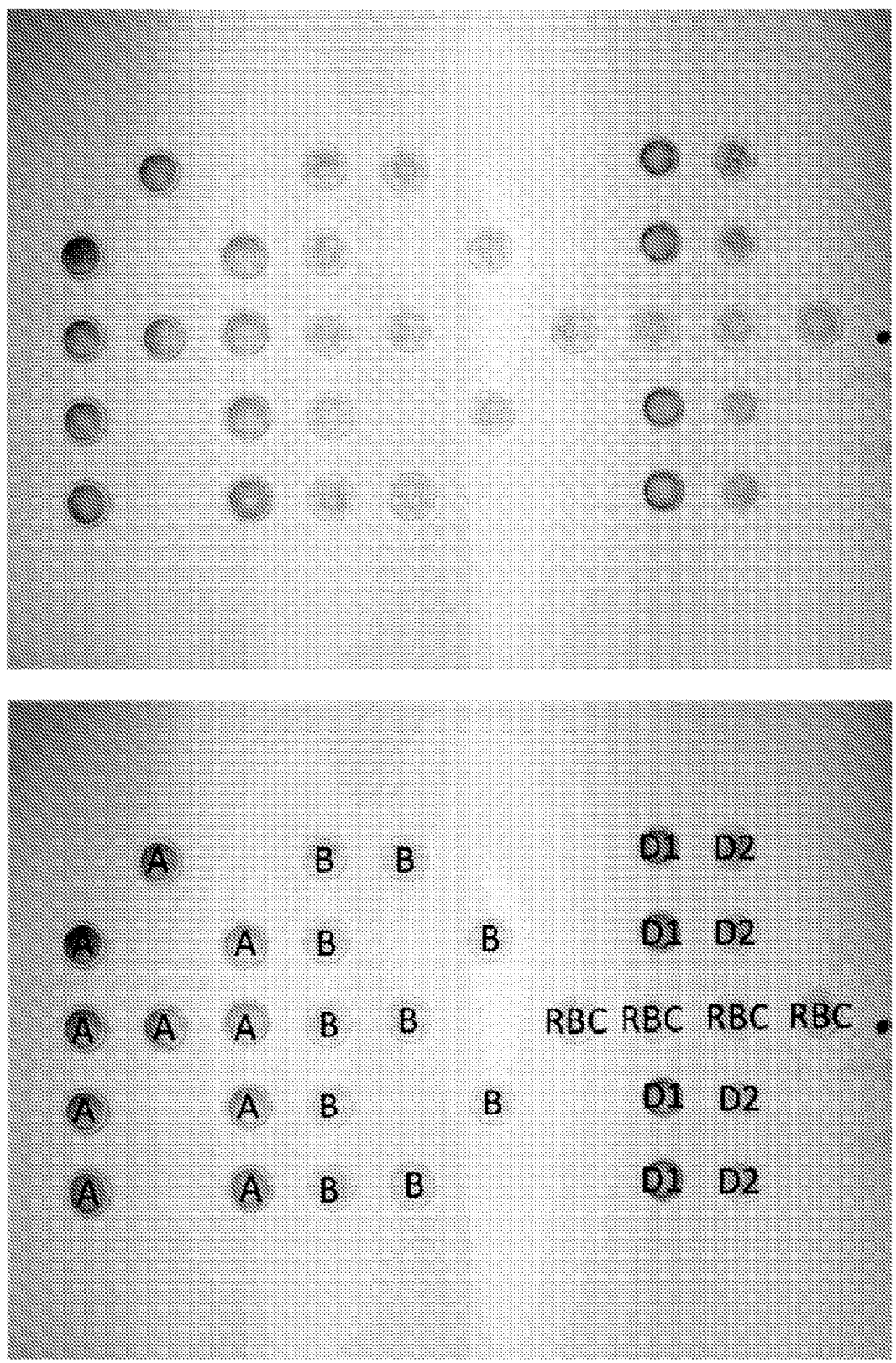
FIG. 24 illustrates a POEGMA antibody array for detection of blood group antigens by visual readout. Array displays blood type as A, B, or AB, with a positive or negative sign. O is indicated by absence of A or B. Antibody Locations in Array: RBC=33F1 Anti-Human Red Blood Cell; A=GAMA120 Anti-A; B=GAMA110 Anti-B; D1=F8D8 Anti-D; D2=GAMA401 Anti-D.

Optimized printing conditions and geometries, as determined by the experiments described in examples 10-15 will be used to print arrays designed to detect both AFP and AFP-L3 (the duplex array is represented in the original D4 assay format in FIG. 16, although a new geometry can have been chosen at this point). Dose-response curves covering concentrations from 0 g/mL to 1 µg/mL will be generated using analyte-spiked buffer, followed by dose-response curves using analyte-negative chicken blood spiked with analyte. Each analyte will be tested in the duplex array individually and the FOM will be compared to those determined in example 15 and example 16. In multiplexed immunoassays, the potential exists for unforeseen cross-reactivity between unmatched capture and detection antibodies or their targets. Exposing arrays to single marker-spiked blood will reveal any potential cross-reactivity, and subsequent rounds of antibody selection will be used if necessary. The assay will be evaluated in terms of its LOB, LOD, LCR, LOQ and COV, as described in example 12.

Exemplary duplexed D4 assays for the detection of both AFP and AFP-L3 described herein will be quantitative and maintain the FOM of the single analyte tests evaluated in examples 15 and 16.

Example 17. Optimization of Detector Design

Several aspects of the detector will be optimized, including cost, wavelength, spectral width and power output of LEDs, as well as the angle of the LED illumination. A number of optical filter options also exist, and these will be evaluated with the primary goal of keeping overall cost as low as possible. Testing will occur by imaging a D4 chip containing a standardized array of fluorescently labeled protein with each detector variation, and the lowest cost components capable of delivering sufficiently high signal intensity to the cell phone camera will be chosen.

Exemplary detectors described herein will be composed of the least expensive components that still provide sufficient imaging of test arrays. An example would be a detector that is comprised of components totaling $10 and produces an average intensity of 1,000 counts/pixel/second when imaging a test array.

Example 18. Writing a Mobile Phone Application to Quantify Spot Intensities

Two options exist for image analysis: 1) transmit image to a central server for analysis, and 2) perform analysis on phone. The option to perform image analysis on the phone is suitable for LMIC applications where a data signal cannot be readily available. For example, the JavaCV image processing library can be adapted to meet the needs here. During app development, images generated by examples 10-17 will be used to benchmark the on-phone analysis against the previously obtained results from image analysis software bundled with commercial microarray scanners.

An exemplary application described herein will comprise a JavaCV based image analysis tool that is capable of identifying test spots based on their position and producing an average pixel intensity/spot measurement. For example, the application should also be able to refer to a reference dose response curve and scale test spot intensity according to the on-chip calibration standard.

Example 19. Benchmarking of the Entire System

Upon completion of the optimized detector and application, the new FOM will be generated and compared to those obtained for the duplex assay in example 16. An integrated POCT that provides assay results on a smart phone within 20 minutes with performance metrics that are comparable to or better than an ELISA carried out in a central laboratory will be developed.

An exemplary system is would be an integrated POCT that provides assay results on a smart phone within 20 minutes with performance metrics that are comparable to or better than an ELISA carried out in a central laboratory.

Example 20. Clinical Testing of the Developed POCT: Testing with Simulated Blood Samples The integrated D4 assay will be optimized by assays that will be carried out over 4-log scale of concentration in analyte spiked chicken blood in the range of 0 g/ml to 1 µg/ml. The studies described below will be carried out by clinical technicians, and not by the developers of the D4 POCT. This is an important distinction because the experiments described in examples 1-20 will be performed by personnel who are deeply involved in the development of the D4 assay. Because the assay will ultimately be carried out by personnel—typically clinical technicians in a LMIC setting and potentially even by users—who have had no prior exposure to the assay format, it is important in the transition from the lab to field use to hand over the assay to individuals not intimately involved in assay development to verify that the FOM determined in the lab are matched in a setting closer to the LMIC site.

Table 1. summarizes validation criteria for each type. Because the results of the D4 assay will be fundamentally quantitative (a digital readout of fluorescence intensity), precision will be evaluated for these results to inform statistical inference. All test points will be run in triplicate unless otherwise stated. Assay precision will be evaluated first (Table 1). The number of replicates can be adjusted for subsequent tests based on the observed precision, with an end goal of ensuring that target performance parameters can be resolved with 95% confidence. Quantitative method comparison results for the single analyte AFP and AFP-L3 versus the multiplex AFP+AFP-L3 assay will be a set of linear regressions with the D4 multiplex assay as the test case, and the single analyte assays as the reference case. Slope, intercept and coefficient of variation, with appropriate 95% confidence intervals, will be calculated. As the single analyte D4 assay is uncharacterized, a Bland/Altman analysis will also be performed to avoid assumptions about the data.

TABLE 1

Analytical parameters to be evaluated in single-plex and dual-plex assay development in assay transition to field use.

| Parameter | Detail |
|---|---|
| Method Comparison | Clinical specimens assayed single point, n = 50-100 (~e0 patients). Test vs. simplex. Calculate linear regression with all stats, and perform Bland/Altman analysis (see text for additional notes) |
| Accuracy | Analyte spiked to 3 concentrations (low, mid, high), calculate % agreement |
| Specificity | Analyte spiked to low-positive; other multiplexed analytes and possible interferents spiked to 3 concentrations (low, mid, high), calculate % elevation of analyte due to interferent |
| Detection and Quantification Limits | Assay n ≥ 20 replicates of negative control. Calculate σ. LOD = 3σ, LOQ = 10σ |
| Linearity | Dilute known high sample to n ≥ 5 concentrations over assay range, perform linear regression with all stats |
| Assay Range | Method 1: Use linearity data, find fluorescence signal greater than 3σ of the signal from the next lower concentration in the dilution series<br>Method 2: Use fitted infinite response from 5-PL calibrations, subtract 3σ derived from high precision |
| Precision | Analyte spiked to 3 concentrations (low, mid, high), n ≥ 9 for each, (3 operators, 3 days), calculate % CV, (see text for additional notes) |
| Robustness | Vary (±10%) any key parameters identified during development (e.g., sample volume and/or dilution; incubation times and temperatures, antibody concentrations, etc.) not already investigated as part of development. Evaluate performance changes. |
| Accelerated Stability | Store devices at 40° C., test weekly for 2 months, compare to concurrently tested 4° C. stored devices |

Table 1. Anaytical parameters to be evaluated in single-plex and dual-plex assay development by clinical group at Duke in assay transition to field use.

Once the prototype D4 AFP and the dual AFP+AFP-L3 D4 POCTs have been developed, a full capstone validation will be performed following the pathways outlined in Table 1. Prior to initiating work, a detailed validation plan, including SOPs, data format and forms, details on final statistical analysis, and sufficient replication to ensure statistical power (enabled by the preliminary data gathered to date), is created. Results from this validation will be compared to generally accepted diagnostics criteria, which can include: qualitative sensitivity and specificity ≥95%; quantitative method comparison slope 0.95-1.05, bias ≤5%, R2≥0.90; accuracy 85-115% of nominal; precision (CV) ≤10%; linearity ≥0.90, among other assay specific measures (LOD, LOQ, assay range).

Exemplary results of clinical utility will comprise a validation of the D4 assays described herein by inexperienced users that produces sensitivity and specificity 95%; quantitative method comparison slope 0.95-1.05, bias ≤5%, R2≥0.90; accuracy 85-115% of nominal; precision (CV) ≤10%; linearity ≥0.90, among other assay specific measures (LOD, LOQ, assay range) described in example 21.

Example 21. Testing in Freshly Drawn Human Blood

After testing of the D4 assay, a small scale (~20) trial with freshly drawn patient blood will be carried out at Site 1. The D4 results will be compared with an ELISA for AFP and AFP-L3. Details of the clinical study and experimental protocols are described below.

Design of Clinical Study: This section applies to both the pre-validation clinical studies that will be carried out at Site 1 with a limited number of patient blood samples as well as the larger scale clinical trial of the D4 POCT at the LMIC site: Site 2. The largest difference between the two studies will be cohort size, which is anticipated to be ~20 per arm at Site 1, and ~100 per arm at the LMIC clinical site.

Study population: Approval for the study will be obtained from the institutional ethics review committee at each study site and informed consent will be obtained from all participants including patients with hepatocellular carcinoma (HCC) and healthy controls.

HCC will be defined on the basis of ultrasound, CT, or MRI characteristics and biochemistry (AFP serology and liver function enzymes), and will be confirmed by histopathology, according to the American Association for the Study of Liver Diseases guidelines. Tumor stage will be defined according to the Barcelona Clinic Liver Cancer (BCLC) staging system. Tumors with BCLC stage 0+A are classified as early-stage HCC. Diagnosis of chronic HBV infection includes the presence of HBsAg for the previous 6 months, HBV DNA concentrations higher than 103 copies per mL, and raised concentrations of alanine amino transferase in serum, according to the guidelines of prevention and treatment of chronic HBV infection. The diagnosis of cirrhosis will be based on histopathology of liver biopsy samples, and on clinical, laboratory, and imaging evidence where possible, including nodular liver contour, presence of ascites, portal hypertension, varices, enlargement of the caudate lobe, splenomegaly, and collateral portal-venous anastomoses. Patients with cirrhosis who have raised AFP concentrations will be required to have undergone imaging by multiple methods (ultrasonography, CT, or MRI) and to have no evidence of a hepatic mass for at least 3 months before enrolment. Patients who have a history of other solid tumors will be excluded from the study.

The healthy controls will be eligible blood donors with normal liver biochemistry, no history of liver disease, no viral hepatitis, and no malignant disease. The groups are matched in the two cohorts for age and sex as far as possible.

Statistical analysis: In the test stage, a group of HCC patients and a group of healthy control subjects will be recruited. The AFP levels will be summarized by mean, median and standard error in the two groups separately. The null hypothesis will be tested that the median of AFP levels in the two groups are equal versus the alternative hypothesis that they are unequal using the Mann-Whitney test. For the diagnostic test, a subject is classified as "positive" if the AFP level is above a certain cut-off point and otherwise the subject is classified as "negative" for the test. Different cut-off points yield different operating characteristics of the test. Specifically, the sensitivity of the test is the proportion of HCC subjects who are correctly classified as "positive" in the test. The specificity is the proportion of non-HCC subjects who are correctly classified as "negative". In addition, the positive predictive value is the proportion of subjects who are true positives among those who are classified as positives in the test; and the negative predictive value is the proportion of subjects who are true negatives among those who are classified as negatives. The receiver operator characteristic (ROC) curve is obtained by plotting the proportion of true positives versus the proportion of false positives at various cut-off points for the test. The area under the ROC curve (AUC) will be used to evaluate the diagnostic value of the test. Under the null hypothesis that the test has no diagnostic value, the AUC is equal to 0.5, and a higher AUC value (up to 1) indicates higher diagnostic value. With a significance level 0.05, the numbers of subjects in each of the two groups (cases and controls) needed to achieve 80% power to reject the null are about 130, 60, 30, and 20, if the true AUC is 0.6, 0.65, 0.7, and 0.75, respectively. A receiver operator characteristic curve will also be used to seek an optimum cut-off value for diagnosis by maximizing the sum of sensitivity and specificity. The sensitivity, specificity, positive predictive value and negative predictive value of the test with the optimum cut-off will be calculated with their 95% confidence intervals.

Statistical analyses will be done with R (version 3.0.2) and SAS (version 9.0). Differences between two independent groups will be tested with the Mann-Whitney U test (continuous variables and nonparametric analyses). Receiver operating characteristics (ROC) curves will be constructed to assess sensitivity, specificity, and respective areas under the curves (AUCs). The optimum cutoff value for diagnosis will be investigated by maximizing the sum of sensitivity and specificity. Also, sensitivity and specificity under the optimum cutoff value will be calculated along with their 95% confidence intervals. These quantities and their 95% confidence intervals will be compared with those calculated from the test stage.

The exemplary D4 assays from freshly drawn human blood described herein will provide an estimation of the optimum cutoff values for diagnosis with AFP and AFP-L3 by maximizing the sum of sensitivity and specificity. An example would be a cut off value of 250 ng/mL AFP and 100 ng/mL AFP-L3 that provides 90% sensitivity and 85% specificity.

In addition, the D4 assays described herein will be in an integrated POCT format that provides assay results on a smart phone within 20 minutes with performance metrics that are comparable to or better than an ELISA carried out in a central laboratory. Exemplary commercially available ELISAs for performance evaluation include the R&D systems Human alpha-Fetoprotein Quantikine ELISA Kit (DAFP00), with a LOD of 46 µg/mL and an assay range of 312 µg/mL to 20 ng/mL, with a CV %<10 across the assay range.

Example 22. POEGMA Antibody Array for Red Blood Cell Capture: Initial Results

The initial results are shown in FIGS. 18-24.

For proper morphology, in-house developed print buffer can be used for all antibodies except the GAMA401 Anti-D antibody, which should be printed as received.

Array appears specific for A, B, O blood types.

No D-negative blood was available, so specificity of the GAMA401 Anti-D antibody has not yet been demonstrated.

No signal was produced by the F8D8 Anti-D antibody in any of the three blood samples tested; therefore, spot morphology could not be evaluated.

The results demonstrate production of an array with intuitive read out.

Example 23. Detection of DNA

Surface-Initiated Enzymatic Polymerization (SIEP) was performed on the glass slide spotted with Cy5-labeled oligonucleotide primers by incubating each well on the slide with 10 U of TdT, 100 µM dATP monomer, and 0.5 µM, 1 µM, 2 µM, or 5 µM Cy3-dATP nucleotide or a dye-terminator, Cy3-dideoxynucleotides (Cy3-ddATP) in 100 µL TdT buffer. SIEP was carried out for 1 h at 37° C., after which the slides were washed three times with SSC buffer containing 0.1% Tween 20 to facilitate the removal of any nonspecifically bound reactants.

On-chip Fluorescent Labeling of RNA Hybridization by SIEP. A DNA sequence from the glyceraldehyde 3-phosphate dehydrogenase (GAPDH) gene was selected as a model system to test our assay. The fully complementary 5'-biotinylated 17-mer PNA probe [5'-Ac-GTCCAC-CACCCTGTTGC-lysine-biotin-3', 1 µM] (SEQ ID NO:1) and nonspecific PNA probe derived from the hepatitis B virus (HBV) sequence [5'-Ac-ACCTTGTCATGTACCAT-lysine-biotin-3', 1 µM] (SEQ ID NO:2) were individually mixed with streptavidin (2.5 µM) and then spotted using a noncontact printer (Piezzorray, Perkin-Elmer) on a nonfouling poly(oligo(ethylene glycol) methacrylate) (POEGMA) brush, 16,20 grown on a glass substrate. The slides spotted with the probes were then incubated overnight in a vacuum chamber and rinsed with 1×SSC buffer containing 0.1% Tween 20, before use. A dose-response curve of a hybridized target was generated by incubating the printed probes with a solution of the target RNA that covered a 1 µM-0.1 µM concentration range. Each target solution was heated at 95° C. for 10 min prior to hybridization and then quenched in ice and incubated with the printed probe. The assay was carried out using two targets: (1) a 21-mer synthetic RNA target [5'-rGrCrArArCrArGrGrGrUrGrGrUrGrGrArCrCrUrCrA-3'] (SEQ ID NO:3) that is complementary to the probe and a (2) full length in vitro transcribed GAPDH mRNA (~1.4 kb, details found in SI). Each target was incubated overnight (~16 h) with mild shaking at 42° C. in the hybridization buffer (3×SSC, 0.1% Tween 20, and 4.95 M urea). The synthetic RNA was used as received while the in vitro transcribed GAPDH mRNA was either used as received or fragmented by incubation in the fragmentation reagent at 70° C. for 15 min. For fragmented RNA targets, after rinsing (3×) with the wash buffer (1×SCC, 0.1% Tween-20), the bound-fragmented RNA target was enzymatically dephosphorylated on-chip (0.0625 units/µL phosphatase in 0.125% BSA and 0.1% Tween 20) at 37° C. for 1 h to ensure the availability of the 3'-OH. The 3'-OH of the bound RNA target was then converted to DNA by SIEP, using PaP to incorporate a short oligo-dATP (6 units/µL PaP and 500 µM dATP in 1×PaP buffer) at 37° C. for 2 h, followed by SIEP using TdT to incorporate Cy5-dATP (0.1 units/µL TdT, 100 µM dATP, and 0.5 µM Cy3-dATP in 1×TdT buffer) at 37° C. for 1 h. The slides were then rinsed in 1×SSC buffer with 0.1% Tween 20 for 30 min and scanned immediately on a GenePix scanner. The average signal intensity of the spot (background subtracted) was then plotted as a function of the target RNA concentration.

Figure 26:
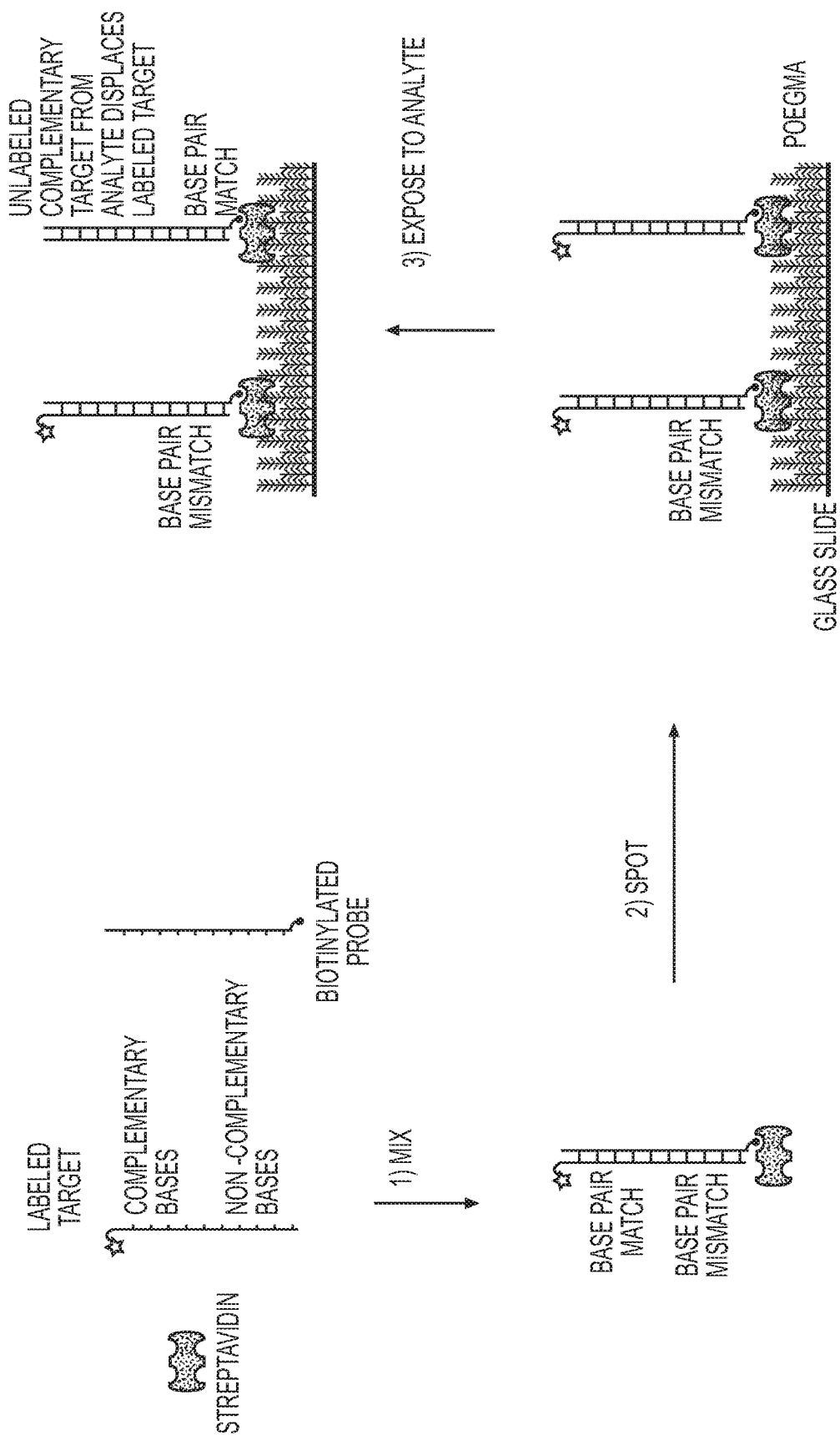
FIG. 26 provides a schematic of a competitive binding assay for single-step detection of microRNA sequences.

Example 24 A Competitive Binding Assay for Single-Step Detection of microRNA Sequences This embodiment is illustrated in FIG. 26. While this embodiment is similar to a competitive immunoassay, the method of delivery of the labeled/competing target is different—in this format, the labeled target is not spiked into the analyte solution, but is instead hybridized directly to the probe prior to spotting. As such, this format relies on microspots of probes that have been hybridized to a labeled target prior to spotting. Designing the sequence of this labeled target to include a number of non-complementary bases will cause a displacement of this pre-hybridized, partially-complementary labeled target by any target present in an analyte solution (target present in the analyte solution does not contain any mismatched bases, and therefore hybridizes with higher affinity to the probe sequence). In this format, a decrease in microspot signal intensity is used to quantify target in the analyte sample. Ideally, this method would avoid an RNA purification step. However, even if RNA purification is required, this method still has the potential to eliminate reverse transcription, labeling, and/or PCR amplification.

The following parameters will be optimized with regard to sensitivity and signal-to-noise ratio. 1. Length of Sequence; 2. Content of Sequence (GC vs AU vs TA); 3. Uniqueness of sequence (does the genome contain examples of other extremely similar sequences) 4. Analyte solution properties (Ionic strength, pH, etc.); 5. Temperature; 6. Location/Content of mismatched bases (beginning/end of probe vs. middle of probe, AC vs AG vs AA, etc.); 7. Length of Probe (how many/which overlapping bases occur between target and probe strands, does the probe contain overhangs before/after complementary portion); 8. Incubation Time. While 1-3 are a function of the targeted sequence and cannot be varied, 4-8 can be used to tailor probe-target binding.

In some embodiments of the invention, soluble spots of a labeled target will be printed alongside probe spots. This technique would more closely resemble traditional DNA array based assays where fold changes in gene expression are measured by labeling a control group with one label (Cy3 for instance), and an experimental group with a separate label (such as Cy5). However, in this embodiment, only the "control" target is labeled, which is added to the analyte solution as the soluble spots of labeled target dissolve. The degree to which this labeled target binds to the probe spots will be inversely related to the concentration of the unlabeled target sequence present in the analyte solution.

Suitable sequences include:

```
miRNA target (mir-155)
                                    (SEQ ID NO: 4)
5'-UUAAUGCUAAUCGUGAUAGGGGU LNA probe
                                    (SEQ ID NO: 5)
5'-CCTATCACGATTAGCATTAA-biotin
``` labeled miRNA targets with partial complementarity (A changed to C, mutation in bold underline)

```
                                    (SEQ ID NO: 6)
5'-UUCAUGCUAAUCGUGAUAGGGGU-Cy5

(SEQ ID NO: 7)
5'-UUCCUGCUAAUCGUGAUAGGGGU-Cy5

(SEQ ID NO: 8)
5'-UUCCUGCUCAUCGUGAUAGGGGU-Cy5

(SEQ ID NO: 9)
5'-UUCCUGCUCCUCGUGAUAGGGGU-Cy5

(SEQ ID NO: 10)
5'-UUCCUGCUCCUCGUGCUAGGGGU-Cy5

(SEQ ID NO: 11)
5'-UUCCUGCUCCUCGUGCUCGGGGU-Cy5
```

Example 25 Targeted Cell Arrays for Enhanced Immunohistochemistry

Immunohistochemistry (IHC) plays a crucial role in the field of pathology, and its importance is destined to increase as companion diagnostics are required for new targeted therapeutics. However, the inherent subjectivity of the assessment of an objective value (the in situ protein concentration) suggests that new technologies are required to achieve the accuracy required for companion diagnostics.

IHC often plays a crucial role in patient care and the determination of course of treatment. An increasing number of drugs are designed to target specific and/or rare cell types, but because of the potential side effects and the high cost of many of these drugs, IHC is often used to predict drug response prior to drug administration. For example, the use of trastuzumab (Herceptin) is only indicated in the treatment of the 20-30% of breast cancers in which the HER2/neu receptor is overexpressed, and prior to the prescription of trastuzumab, breast cancer tumor biopsies must be evaluated by IHC and other methods to determine if HER2 overexpression is in fact present. However, achieving reproducible results by IHC is quite challenging due to a number of sources of variability, which include fixation conditions, specimen pretreatment, reagents, detection methods, washing procedures and interpretation of results. This lack of reproducibility presents a major challenge, and a number of studies have demonstrated the need to improve the quality control measures used in IHC assays. In one study of IHC test results for HER2 overexpression, a 15% discordance rate between initial local testing and follow-up central lab testing was found.

Individual cells will be printed in arrays for analysis. The natural morphology of a tissue sample is largely preserved during traditional IHC, and while in some cases this is both necessary and useful, there are many instances where it merely complicates analysis. For instance, if a tissue biopsy is being examined for overexpression of a particular surface receptor, cells do not have to remain embedded in a tissue sample for analysis. By organizing cells into an array, image acquisition and analysis is greatly simplified, whether being conducted by eye or in an automated format.

Capture agents specific to the targeted cell type will be used to limit the number of extraneous cells. Traditional IHC involves the analysis of whole tissue sections consisting of large numbers of cells, and quite often the majority of these cells are unimportant if the goal is to characterize specific and/or rare cell types. By using surface immobilized capture agents such as antibodies to target specific cell types, it will be possible to select for the specific and/or rare cell types of interest. This technique can be used to limit the number of extraneous cells being analyzed, and thereby reduce analysis time, reagent requirements and the potential for false positives as a result.

Signal-to-noise-ratio and assay interpretation can be significantly improved by eliminating the noise created by non-specific adsorption of labeled detection agents to the substrate background, producing fewer false positives and more sensitive and quantitative results. In addition, wash procedures can be greatly reduced or even eliminated due to the lack of non-specific adsorption, greatly simplifying assay procedures and improving reliability and reproducibility.

One suitable method of preparing arrays according to this aspect of the invention follows. Surface initiated atom transfer radical polymerization will be used to coat glass slides with poly(oligo(ethylene glycol)methacrylate) (POEGMA). We have recently demonstrated the ability of this non-fouling coating to completely eliminate background noise caused by the non-specific adsorption of cells and proteins in assays conducted in complex biological fluids such as blood and cell lysate. Microspot arrays of anti-HER2/neu antibodies will be printed directly onto the POEGMA surface. These microspots will be created using a method of patterning antibodies onto POEGMA surfaces developed in our lab which eliminates the need for chemical activation and deactivation to achieve stable antibody microspots on the non-fouling surface and greatly simplifies the fabrication process. In addition, we have shown that antibodies printed onto POEGMA surfaces using this technique have an exceptionally long shelf life under normal ambient conditions, without the need to refrigerate or store in buffer, which makes storage and transport of these arrays much simpler. Breast tumor samples, which have already received a HER2/neu expression score of 0 to 3+, will be used to evaluate the assay. Tumor samples will be treated with collagenase D, and the anti-HER2/neu arrays on POEGMA will be exposed to the resulting cell suspension. HER2/neu positive cells will be captured by the anti-HER2neu microspots (circular 10 um diameter microspots will be used so that there will be approximately 1 cell per microspot), and subsequent labeling with a second anti-Her2/neu antibody will be used to quantify the Her2/neu expression of each cell. Results will be compared to the previously determined HER2/neu expression values of 0 to 3+.

This embodiment will make IHC tests more reliable, faster, less expensive and more easily applied at the point of care. HER2/neu expression in breast cancer tumor will be assayed using this embodiment of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed:

1. A chip comprising a channel therethrough that draws biological fluid into the chip by capillary action and a non-fouling polymer layer disposed on at least one surface of the channel, wherein the channel is substantially enclosed within the chip, wherein the chip further comprises a capture agent that is directly, non-covalently bound to the non-fouling polymer layer, wherein the non-fouling polymer layer comprises a homopolymer of hydroxy terminated polymerized oligoethylene glycol methyl methacrylate (OEGMA), or a copolymer of methoxy-terminated OEGMA and hydroxy-terminated OEGMA.

2. The chip of claim 1, wherein the non-fouling polymer layer i) after being primed with phosphate buffered saline (PBS) solution having a pH of 7.4 for 10 minutes; ii) then being exposed to a fibronectin solution at a concentration of 1 mg fibronectin per ml for 20 minutes at 25° C.; and iii) then being rinsed for 10 minutes with a PBS solution having a pH of 7.4 for 10 minutes; when evaluated by surface plasmon resonance or alternative method shows a fibronectin absorption of equal to or below 1 ng per $cm^2$.

3. The chip of claim 1, wherein the capture agent retains at least about 50% binding activity for at least about 1 month at a temperature of about 25° C., when the chip is stored such that the non-fouling polymer layer comprises waters of hydration but not bulk water.

4. The chip of claim 1, wherein the chip is capable of analyzing a body fluid to detect an analyte therein.

5. The chip of claim 4, wherein the analyte is or comprises a human A blood type antigen, a human B blood type antigen, a human AB blood type antigen, a human O blood type antigen, a human Rh factor antigen, a glycophorin, a bio-threat agent, an antigen from an infectious agent, a cancer antigen, an antigen associated with cardiovascular disease, an antigen associated with a metabolic disease, or any combination thereof, or an antibody that recognizes any of the above.

6. The chip of claim 1, further comprising a detection agent.

7. A detector comprising:
the chip of claim 1;
a body configured to accept a chip comprising a non-fouling polymer layer;
a lid which, in combination with the body, substantially surrounds the chip when the chip is disposed in the body; and
a light source that is positioned to emit a light of a first wavelength such that the light contacts the non-fouling polymer layer.

8. The detector of claim 7, further comprising a filter that is positioned to filter light emitted from the non-fouling polymer layer.

9. The detector of claim 7, further comprising a lens that is positioned to magnify a light of the second wavelength that passes through the filter.

10. The detector of claim 9, wherein the light source illuminates the non-fouling polymer layer of the chip at an angle allowing excitation of a detection agent contained within the chip.

11. The detector of claim 7, comprising a chip,
wherein the chip comprises a first substrate with a first face,
wherein the first face is substantially flat,
wherein the non-fouling polymer layer is positioned such that the light source and the non-fouling polymer layer are on opposite sides of the first face, and
wherein the light source is configured to illuminate the first substrate and the non-fouling polymer layer at an angle that is less than or equal to 90 degrees as measured from a line that is perpendicular to the first face.

12. A method of making the chip of claim 1, comprising depositing at least one capture agent into a non-fouling polymer layer, wherein the non-fouling polymer is surrounded by the chip.

13. The method of claim 12, further comprising depositing at least one detection agent onto the non-fouling polymer layer.

14. A method of detecting the presence or absence of an analyte, comprising:
a) contacting the chip of claim 1 with a sample; and
b) determining the presence or absence of the analyte,
wherein a detectable signal from the chip indicates the presence of the analyte, or absence of a detectable signal from the chip indicates the absence of the analyte.

15. A system for detecting an analyte, comprising:
the chip of claim 1 comprising a non-fouling polymer layer;
a detector; and
a cell phone.

16. The system of claim 15, wherein the chip comprises a capture agent and a detection agent disposed on the non-fouling polymer layer.

17. The system of claim 15, wherein the capture agent is non-covalently attached to the non-fouling polymer layer.

18. The system of claim 15, wherein the analyte is or comprises a human A blood type antigen, a human B blood type antigen, a human AB blood type antigen, a human O blood type antigen, a human Rh factor antigen, a glycophorin, a bio-threat agent, an antigen from an infectious agent, a cancer antigen, an antigen associated with cardiovascular disease, an antigen associated with a metabolic disease, or any combination thereof, or an antibody that recognizes any of the above.

19. The system of claim 15, wherein the detection agent comprises a flurophore and the detector comprises a light sources that emits a wavelength of light that excites the fluorophore.

20. The chip of claim 1, wherein the non-fouling polymer layer is about 10 to about 150 mm thick.

* * * * *